(12) United States Patent
Cohen et al.

(10) Patent No.: US 7,455,835 B2
(45) Date of Patent: *Nov. 25, 2008

(54) METHODS FOR TREATING IMMUNE SYSTEM DISEASES USING A SOLUBLE CTLA4 MOLECULE

(75) Inventors: Robert Cohen, Newtown, PA (US); Robert James Peach, San Diego, CA (US); David Hagerty, Cardiff by the Sea, CA (US); Suzette Carr, Hopewell, NJ (US); Jean-Claude Becker, Princeton, NJ (US); Peter S. Linsley, Seattle, WA (US); Joseph Roy Naemura, Bellevue, WA (US); Jurgen Bajorath, Bonn (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,195

(22) Filed: Jul. 2, 2001

(65) Prior Publication Data

US 2003/0083246 A1    May 1, 2003

Related U.S. Application Data

(60) Provisional application No. 60/215,913, filed on Jul. 3, 2000.

(51) Int. Cl.
*A61K 38/16* (2006.01)
*C07K 14/00* (2006.01)
*C07K 14/705* (2006.01)

(52) U.S. Cl. ............... 424/134.1; 514/12; 530/350; 530/387.3

(58) Field of Classification Search .......... 424/185.1, 424/192.1; 530/351
See application file for complete search history.

(56) References Cited

U.S. PATENT DOCUMENTS

| | | | |
|---|---|---|---|
| 5,434,131 A | | 7/1995 | Linsley et al. |
| 5,624,823 A * | | 4/1997 | Sachs et al. ............. 435/69.52 |
| 5,637,481 A | | 6/1997 | Ledbetter et al. |
| 5,708,037 A | | 1/1998 | Yagita |
| 5,747,034 A * | | 5/1998 | de Boer et al. ............ 424/137.1 |
| 5,770,197 A | | 6/1998 | Linsley et al. |
| 5,773,253 A | | 6/1998 | Linsley et al. |
| 5,844,095 A | | 12/1998 | Linsley et al. |
| 5,851,795 A | | 12/1998 | Linsley et al. |
| 5,885,579 A | | 3/1999 | Linsley et al. |
| 5,885,796 A | | 3/1999 | Linsley et al. |
| 5,916,560 A | | 6/1999 | Larsen et al. |
| 5,958,403 A | | 9/1999 | Strom et al. |
| 5,968,510 A | | 10/1999 | Linsley et al. |
| 5,977,318 A | | 11/1999 | Linsley et al. |
| 5,993,800 A | | 11/1999 | Linsley et al. |
| 6,040,292 A * | | 3/2000 | Sommer ................. 514/12 |
| 6,090,914 A | | 7/2000 | Linsley et al. |
| 6,132,992 A | | 10/2000 | Ledbetter et al. |
| 6,444,792 B1 | | 9/2002 | Gray et al. |
| 6,689,803 B2 * | | 2/2004 | Hunter ................. 514/365 |
| 6,750,334 B1 * | | 6/2004 | Gray et al. .............. 536/23.4 |
| 7,179,466 B2 * | | 2/2007 | Le et al. ................. 424/145.1 |
| 2002/0039577 A1 * | | 4/2002 | Townsend et al. ........ 424/131.1 |
| 2002/0182211 A1 * | | 12/2002 | Peach et al. ............. 424/143.1 |
| 2003/0083246 A1 * | | 5/2003 | Cohen et al. ............ 514/12 |
| 2005/0214313 A1 * | | 9/2005 | Peach et al. ............. 424/185.1 |

FOREIGN PATENT DOCUMENTS

| | | |
|---|---|---|
| EP | 0 613 944 A2 | 9/1994 |
| EP | 0 682 039 A1 | 11/1995 |
| WO | WO 93/00431 | 1/1993 |
| WO | WO 93/19767 | 10/1993 |
| WO | WO94/01547 | 1/1994 |
| WO | WO 94/28912 | 12/1994 |
| WO | WO 94/29436 | 12/1994 |
| WO | WO95/06481 | 3/1995 |
| WO | WO95/28957 | 11/1995 |
| WO | WO 95/33770 | 12/1995 |
| WO | WO 95/33823 | 12/1995 |
| WO | WO 95/34320 | 12/1995 |
| WO | WO 96/14865 | 5/1996 |
| WO | WO 96/23071 | 8/1996 |
| WO | WO/ 97/28267 | 8/1997 |
| WO | WO 98/31820 | 7/1998 |
| WO | WO 98/33513 | 8/1998 |
| WO | WO 98/56417 | 12/1998 |
| WO | WO 00/23115 | 4/2000 |
| WO | WO 01/54732 A1 | 8/2001 |
| WO | WO 01/90122 A2 | 11/2001 |
| WO | WO 01/92337 | 12/2001 |
| WO | WO 02/02638 A2 | 1/2002 |

OTHER PUBLICATIONS

U.S. Appl. No. 60/214,065.*

(Continued)

Primary Examiner—Ilia Ouspenski
(74) Attorney, Agent, or Firm—Audrey Sher; Nickki L. Parlet

(57) ABSTRACT

The present invention relates to compositions and methods for treating rheumatic disease by administering to a subject, soluble CTLA4 molecules that block endogenous B7 molecules from binding their ligands.

31 Claims, 52 Drawing Sheets

OTHER PUBLICATIONS

Borigini et al., Bailliere's Clinical Rheumatology, 1995, 9: 689-710.*

Battleman, David S. et al., "HSV-1 Vector-Mediated Gene Transfer of the Human Nerve Growth Factor Receptor p75$^{hNGFR}$ Defines High Affinity NGF Binding," *The Journal of Neuroscience*, Mar. 1993, 13(3):941-51. (Exhibit 6).

Broach, James R., "Construction of High Copy Yeast Vectors Using 2-μm Circle Sequences," *Methods in Enzymology*, 1983, 101:307-25. (Exhibit 7).

Byrn, Randal A. et al., "Characterization of In Vitro Inhibition of Human Immunodeficiency Virus By Purified Recombinant CD4," *Journal of Virology*, Oct. 1989, 63(10):4370-5. (Exhibit 8).

Carroll, R. et al., "SZ 401 Construction and Characterization of Replication-Defective HIV-1 Packaging Cell Lines," *Journal of Cell Biochemistry*, 1993, 17E:241. (Exhibit 9).

Clarke, Louise et al., "Selection Procedure for Isolation of Centromere DNAs from *Saccharomyces cerevisiae*," *Methods in Enzymology*, 1983, 101:300-7. (Exhibit 10).

Cohen, Stanley N. et al., "Nonchromosomal Antibiotic Resistance in Bacteria: Genetic Transformation of *Escherichia coli* by R-Factor DNA," *Proc. Nat'l. Acad. Sci, USA*, Aug. 1972, 69(8):2110-4. (Exhibit 11).

Dariavach, Piona et al., "Human Ig Superfamily CTLA-4 Gene: Chromosomal Localization and Identity of Protein Sequence Between Murine and Human CTLA-4 Cytoplasmic Domains," *Eur. J. Immunol.*, 1988, 18:1901-5. (Exhibit 12).

Dash, Bret et al., "Deletion of a Single N-Linked Glycosylation Site From the Transmembrane Envelope Protein of Human Immunodeficiency Virus Type 1 Stops Cleavage and Transport of gp160 Preventing env-mediated Fusion," *Journal of General Virology*, 1994, 75:1389:97. (Exhibit 13).

Davison, Elliott, "Obtaining Infectious Virus From Recombinant Plasmids" in Molecular Virology: A Practical Approach. Chapter 7 (IRL Press, New York, NY, 1993), pp. 184-186. (Exhibit 14).

Falk, Kirsten et al., "Both Human and Mouse Cells Expressing H-2K$^b$ and Ovalbumin Process the Same Peptide, SIINFEKL," *Cellular Immunology*, 1993, 150:447-52. (Exhibit 15).

FDA. CDER Guideline for the Clinical Evaluation of Anti-Inflammatory and Antirheumatic Drugs. Apr. 1998. (Exhibit 16).

FDA. Guidance for Industry: Clinical Development Programs for Drugs, Devices and Biological Products for the Treatment of Rheumatoid Arthritis (RA). Feb. 1999. (Exhibit 17).

Felson, David T. et al., "The American College of Rheumatology Preliminary Core Set of Disease Activity Measures for Rheumatoid Arthritis Clinical Trials," *Arthritis and Rheumatism*, Jun. 1993, 36(6):729-40. (Exhibit 18).

Felson, David T. et al., "American College of Rheumatology Preliminary Definition of Improvement in Rheumatoid Arthritis," *Arthritis and Rheumatism*, Jun. 1995, 38(6):727-35. (Exhibit 19).

Fiers, W. et al., "Complete Nucleotide Sequence of SV40 DNA," *Nature*, May 1978, 273:113-20. (Exhibit 20).

Fries, James F. et al., "The Dimensions of Health Outcomes: The Health Assessment Questionnaire, Disability and Pain Scales," *Journal of Rheumatology*, 1982, 9(5):789-93. (Exhibit 21).

Fujikawa, Kiyomi et al., "Nuclear Localization and Transforming Activity of Human Papillomavirus Type 16 E7-β-Galactosidase Fusion Protein: Characterization of the Nuclear Localization Sequence," *Virology*, 1994, 204:789-93. (Exhibit 22).

Gerard, C. et al., "Production and Characterization of Polyclonal Antibodies Recognizing the Intracytoplasmic Third Loop of the 5-Hydroxytryptamine$_{1A}$ Receptor," *Neuroscience*, 1994, 62(3):721-39. (Exhibit 23).

Goeddel, David V. et al., "Synthesis of Human Fibroblast Interferon by *E. coli*," *Nucleic Acids Research*, 1980, 8(18):4057-74. (Exhibit 24).

Greene, JoAnne L. et al., "Covalent Dimerization of CD28/CTLA-4 and Oligomerization of CD80/CD86 Regulate T Cell Costimulatory Interactions," *The Journal of Biological Chemistry*, Oct. 25, 1996, 271(43):26762-71. (Exhibit 25).

Hansen, John A. et al., "Monoclonal Antibodies Identifying a Novel T-Cell Antigen and Ia Antigens of Human Lymphocytes," *Immunogenetics*, 1980, 10:247-60. (Exhibit 26).

Hartley, R. D. et al., "Toxic Metabolites of *Aspergillus Flavus*," *Nature*, Jun. 15, 1963, 198:1056-8. (Exhibit 27).

Hess, B. et al., "Cooperation of Glycolytic Enzymes," *Advances in Enzyme Regulation*, 1969, 7:149-67. (Exhibit 28).

Hitzeman, Ronald A. et al., "Isolation and Characterization of the Yeast 3-Phosphoglycerokinase Gene (PGK) by an Immunological Screening Technique," *The Journal of Biological Chemistry*, 1980, 255(24):12073-80. (Exhibit 29).

Holland, Michael J. and Janice P. Holland, "Isolation and Identification of Yeast Messenger Ribonucleic Acids Coding for Enolase, Glyceraldehyde-3-phosphate Dehydrogenase, and Phosphoglycerate Kinase," *Biochemistry*, Nov. 1978, 17(23):4900-7. (Exhibit 30).

Ikeda, Toshido et al., "Isolation of a cDNA Encoding the Chicken p50B/p97 (Lyt-10) Transcription Factor," *Gene*, 1994, 138:193-6. (Exhibit 31).

Johnsson, Bo et al., "Immobilization of Proteins to a Carboxymethyldextran-Modified Gold Surface for Biospecific Interaction Analysis in Surface Plasmon Resonance Sensors," *Anal Biochem*, Nov. 1991, 198:268-77. (Exhibit 32).

Jones, Nancy H. et al., "Isolation of Complementary DNA Clones Encoding the Human Lymphocyte Glycoprotein T1/Leu-1," *Nature*, Sep. 1986, 323:346-9. (Exhibit 33).

Karin, Michael and Robert I. Richards, "Human Metallothionein Genes—Primary Structure of the Metallothionein-II Gene and a Related Procesed Gene," *Nature*, Oct. 1982, 299(5886):797-802. (Exhibit 34).

Khilko, Sergei N. et al., "Direct Detection of Major Histocompatibility Complex Class I Binding to Antigenic Peptides Using Surface Plasmon Resonance Peptide Immobilization and Characterization of Binding Specificity," *Journal of Biological Chemistry*, Jul. 1993, 268(21):15425-34. (Exhibit 35).

Kolhekar, Aparna S. et al., "Peptidylglycine α-Hydroxylating Monooxygenase: Active Site Residues, Disulfide Linkages and a Two-Domain Model of the Catalytic Core," *Biochemistry*, 1997, 36:10901-9. (Exhibit 36).

Kriegler, Michael, ed., "Gene Transfer and Expression, Laboratory Manual," 1991, 96-8. (Exhibit 37).

Larsen, Arvi et al., "Radiographic Evaluation of Rheumatoid Arthritis and Related Conditions by Standard Reference Films," *Acta-Radiologica-Diagnosis*, Jul. 1997, 18(4):481-91. (Exhibit 38).

Lasky, Laurence A. et al., "Neutralization of the AIDS Retrovirus by Antibodies to a Recombinant Envelope Glycoprotein," *Science*, 1986, 233(4760):209-12. (Exhibit 39).

Lenschow, Deborah J. et al., "Long-Term Survival of Xenogeneic Pancreatic Islet Grafts Induced by CTLA41g," *Science*, Aug. 1992, 257:789-92. (Exhibit 40).

Linsley, Peter S. et al., "Binding Stoichiometry of the Cytotoxic T Lymphocyte-associated Molecule-4 (CTLA-4) A Disulfide-Linked Homodimer Binds Two CD86 Molecules," *The Journal of Biological Chemistry*, 1995, 270(25):15417-24. (Exhibit 41).

Linsley, Peter S. et al., "Coexpression and Functional Cooperation of CTLA-4 and CD28 on Activated T Lymphocytes," *J. Exp. Med.* Dec. 1992, 176:1595-1604. (Exhibit 42).

Linsley, Peter S. and Jeffrey Ledbetter, "The Role of the CD28 Receptor During T Cell Responses to Antigen," *Annu. Rev. Immunol.*, 1993, 11:191-212. (Exhibit 43).

Linsley, Peter S. et al., "Human B7-1 (CD80) and B7-2 (CD86) Bind with Similar Avidities but Distinct Kinetics to CD28 and CTLA-4 Receptors," *Immunity*, Dec. 1994, 1:793-801. (Exhibit 44).

Linsley, Peter S. et al., "Immunosuppression in Vivo by a Soluble Form of the CTLA-4 T Cell Activation Molecule," *Science*, Aug. 1992, 257:792-5. (Exhibit 45).

Lipsky, Peter E., "Rheumatoid Arthritis," *Harrison's Principles of Internal Medicine 13$^{th}$ Edition*, Isselbacher, et al., eds., 1992, 2:1648-55. (Exhibit 46).

Maini, Ravinder et al., "Infliximab (Chimeric Anti-Tumour Necrosis Factor α Monoclonal Antibody) Versus Placebo in Rheumatoid Arthritis Patients Receiving Concomitant Methotrexate: A Randomised Phase III Trial," *The Lancet*, Dec. 1999, 354:1932-9. (Exhibit 47).

Malik, Najma et al., "Molecular Cloning, Sequence Analysis and Functional Expression of a Novel Growth Regulator, Oncostatin M," *Molecular and Cellular Biology*, Jul. 1989, 9(7):2847-53. (Exhibit 48).

Martin, Paul J. et al., "Preincubation of Donor Bone Marrow Cells with a Combination of Murine Monoclonal Anti-T-Cell Antibodies Without Complement Does Not Prevent Graft-Versus-Host Disease After Allogenic Marrow Transplantation," *Journal of Clinical Immunology*, 1984, 4(1):18-22. (Exhibit 49).

Mathiesen, T. et al., "Prolonged Survival and Vascularization of Xenografted Human Glioblastoma Cells in the Central Nervous System of Cyclosporine A Treated Rats," *Cancer Letters*, 1989, 44:151-6. (Exhibit 50).

Metzler, William J. et al., "Solution Structure of Human CTLA-4 and Delineation of a CD80/CD86 Binding Site Conserved in CD28," *Nature Structural Biology*, Jul. 1997, 4(7):527-31. (Exhibit 51).

Moreland, Larry W. et al., "Etanercept Therapy in Rheumatoid Arthritis A Randomized, Controlled Trial," *Ann. Intern. Med.*, 1999, 130:478-86. (Exhibit 52).

Mueller, Daniel L. et al., "Clonal Expansion Versus Functional Clonal Inactivation: A Costimulatory Signalling Pathway Determines the Outcome of T Cell Antigen Receptor Occupancy," *Ann. Rev. Immunol.*, 1989, 7:445-80. (Exhibit 53).

O'Shannessy, Daniel J. et al., "Determination of Rate and Equilibrium Binding Constants for Macromolecular Interactions Using Surface Plasmon Resonance: Use of Nonlinear Least Squares Analysis Methods," *Analytical Biochemistry*, 1993, 212:457-68. (Exhibit 54).

Oaks, Martin K. et al., "A Native Soluble Form of CTLA-4," *Molecular Immunology*, 2000, 201:144-53. (Exhibit 55).

Peach, Robert J. et al., "Complementarity Determining Region 1 (CDR1)- and CDR3-analogous Regions in CTLA-4 and CD28 Determine the Binding to B7-1," *J. Exp. Med.*, Dec. 1994, 180:2049-58. (Exhibit 56).

Rammensee, Hans-Georg et al., "Peptides Naturally Presented by MHC Class 1 Molecules," *Annu. Rev. Immunol.*, 1993, 11:213-44. (Exhibit 57).

Ruddy S. et al., Kelley's Textbook of Rheumatology, 6th Edition. W. B. Saunders Company 2001; vol. 1:823-833. (Exhibit 58), Chapter 56, Stein, C.M. and Pincus.

Ruddy S. et al., Kelley's Textbook of Rheumatology, 6th Edition. W. B. Saunders Company 2001; vol. 2:1001-1022. (Exhibit 59), Chapter 66, Harris, E.D.

Sharp, John T. et al., "How Many Joints in the Hands and Wrists Should be Included in a Score of Radiologic Abnormalities Used to Assess Rheumatoid Arthritis," *Arthritis and Rheumatism*, Dec. 1985, 28(12):1326-35. (Exhibit 60).

Shimatake, Hiroyuki and Martin Rosenberg, "Purified λ Regulatory Protein cII Positively Activates Promoters for Lysogenic Development," *Nature*, Jul. 1981, 292:128-32. (Exhibit 61).

Smith, Douglas H. et al., "Blocking of HIV-1 Infectivity by a Soluble, Secreted Form of the CD4 Antigen," *Science*, Dec. 1987, 238:1704-7. (Exhibit 62).

Stinchcomb, D. T. et al., "Isolation and Characterisation of a Yeast Chromosomal Replicator," *Nature*, Nov. 1979, 282:39-43. (Exhibit 63).

Tan, Patrick et al., "Induction of Alloantigen-specific Hyporesponsiveness in Human T Lymphocytes by Blocking Interaction of CD28 with its Natural Ligand B7/BBI," *J. Exp. Med.*, Jan. 1993, 177:165-73. (Exhibit 64).

Turka, Laurence A. et al., "T-Cell Activation by the CD28 Ligand B7 is Required for Cardiac Allograft Rejection In Vivo," *Proc. Nat'l. Acad. Sci. USA*, Nov. 1992, 89:11102-5. (Exhibit 65).

Toyama, Reiko and Hiroto Okayama, "Human Chorionic Gonadotropin α and Human Cytomegalovirus Promoters are Extremely Active in the Fission Yeast *Schizosaccharomyces pombe*," *FEBS*, Jul. 1990, 268(1):217-21. (Exhibit 66).

Tschumper, Gary and John Carbon, "Sequence of a Yeast DNA Fragment Containing a Chromosomal Replicator and the TRPI Gene," *Gene*, 1980, 10:157-66. (Exhibit 67).

Urlaub, Gail et al., "Effect of Gamma Rays at the Dihydrofolate Reductase Locus: Deletions and Inversions," *Somatic Cell and Molecular Genetics*, 1986, 12(6):555-66. (Exhibit 68).

Weinblatt, Michael E. et al., "A Trial of Etanercept, A Recombinant Tumor Necrosis Factor Receptor:Fc Fusion Protein, in Patients with Rheumatoid Arthritis Receiving Methotrexate," *The New England Journal of Medicine*, Jan. 28, 1999, 340(4):253-9. (Exhibit 69).

Williams, R. Sanders et al., "Introduction of Foreign Genes into Tissues of Living Mice By DNA-coated Microprojectiles," *Proc. Nat'l. Acad. Sci. USA*, Apr. 1991, 88:2726-30. (Exhibit 70).

Yokochi, Takashi et al., "B Lymphoblast Antigen (BB-1) Expressed on Epstein-Barr Virus-Activated B Cell Blasts, B Lymphoblastoid Cell Lines and Burkitt's Lymphomas," *The Journal of Immunology*, Feb. 1982, 128(2):823-7. (Exhibit 71).

Linsley, et al., 1991, *J.Exp.Med*. "CTLA-4 Is a Second Receptor for the B Cell Activation Antigen B7" 174:561-569. (Exhibit 72).

Gimmi, et al., 1993, *Proc.Natl.Acad.Sci. USA* "Human T-Cell clonal anergy is induced by antigen presentation in the absence of B7 costimulation" 90:6586-6590. (Exhibit 73).

Azuma et al., 1993 *Nature* "B70 antigen is a second ligand for CTLA-4 and CD28" 366:76-79. (Exhibit 74).

Ronchese et al., 1994 *J.Exp.Med* "Mice Transgenic for a Soluble Form of Murine CTLA-4 Show Enhanced Expansion of Antigen-specific CD4 T Cells and Defective Antibody production In Vivo" 179:809-817. (Exhibit 75).

Griggs et al., 1996 *J.Exp.Med* "The Relative Contribution of the CD28 and gp39 Costimulatory pathways in the Clonal Expansion and Pathgenic Acquisition of Self-reactive T Cells" 183:801-810. (Exhibit 76).

Verwilghen et al., 1994 *J-Immunol.* Expression of Functional B& and CTLA4 on Rheumatoid Synovial T Cells 153:1378-1385. (Exhibit 77).

Blazar et al., 1994 *Blood* "In Vivo Blockade of CD28/CDLA4: Interaction With CTLA4-Ig Reduces Lethal Murine Graft-Versus-Host Disease Across the Major Histocompatibility Complex Barrier in Mice" 83:3815-3825. (Exhibit 78).

Finck et al., *Science* "Treatment of Murine lupus with CTLA4Ig" 265:1225-1227. (Exhibit 79).

Perrin et al., 1995 *J-Immunol* "Role of B7:CD28/CTLA4 in the Induction of Chronic Relapsing Experimental Allergic Encephalomyelitis" 154:1481-1490. (Exhibit 80).

Pearson et al., 1994 *Transplantation* "Transplantation Tolerance Induced by CTLA4-Ig" 57:1701-1706. (Exhibit 81).

Baliga et al., 1994 *Transplantation* "CTLA4Ig Prolongs Allograft Survival While Suppressing Cell-Mediated Immunity" 58:1082-1090. (Exhibit 82).

Tepper et al., 1994 *Transplantation Proceedings* "Tolerance Induction by soluble CTLA4 in a Mouse Skin Transplant Model" 26:3151-3154. (Exhibit 83).

Perico et al., 1995 *Kidney International* "Toward novel antirejection strategies: In vivo immunosuppressive properties of CTLA4Ig" 47:241-246. (Exhibit 84).

Finck et al., 1994 *Arthritis and Rheumatism* "Effects of CTLA4Ig in murine lupus" 37:S222. (Exhibit 85).

Nishikawa et al., 1994 *Eur J. Immunol.* "Effect of CTLA-4 chimeric protein on rat autoimmune anti-glomerular basement membrane glomerulonephritis" 24:1249-1254. (Exhibit 86).

Wallace et al., 1994 *Transplantation* "CTLA4ig treatment ameliorates the lethality of murine graft-versus-host disease across major histocompatibility complex barriers" 58:602-610. (Exhibit 87).

Damle et al., *J. Immunol.* "Costimulation of T Lymphocytes with integrin Ligands intercellular Adhesion Molecule-1 or Vascular Cell Adhesion Molecule-1 Induces Functional Expression of CTLA-4, a Second Receptor for B7" 152:2686-2697. (Exhibit 88).

Milich, et al., 1994 *J. Immunol* "Soluble CTLA-4 can suppress autoantibody production and elicit long term unresponsiveness in a novel transgenic model," 153:429-435. (Exhibit 89).

Webb, et al., 1996 *Eur J. Immunol* "Prevention and amelioration of collagen-induced arthritis by blockade of the CD28 co-stimulatory pathway: requirement for both B7-1 and B7-2," 26:2320-2328. (Exhibit 90).

Van Oosterhout, et al., 1997 *Am.J.Respir.Cell Mol.Biol*. "Murine CTLA4-IgG Treatment Inhibits Airway Eosinophilia and Hyper-responsiveness and Attenuates IgE Upregulation in a Murine Model of allergic Asthma," 17:386-392. (Exhibit 91).

Abrams et al., 1999 *J-Clin-Invest* CTLA4Ig-mediated blockade of T-cell costimuation in patients with psoriasis vulgaris. 103:1243-1252. (Exhibit 92).

Ibrahim, et al., 1996 *Blood* "CTLAIG Inhibits Alloantibody Responses to Repeated Blood Transfusions," 88:4594-4600. (Exhibit 93).

Lenschow, et al., 1995 *J Exp Med* "Differential Effects of anti-B7-1 and Anti-b&-2 Monoclonal Antibody Treatment on the Development of Diabetes in the Nonobese Diabetic Mouse," 181:1145-1155. (Exhibit 94).

Lenschow, et al., 1992 *Science* "Long-Term Survival of Xenogeneic Pancreatic islet Grafts Induced by CTLA4Ig," 257:789-792. (Exhibit 95).

Sayegh., 1999 *J Clin Invest* "Finally, CTLA4Ig graduates to the clinic," 103:1223-1225. (Exhibit 96).

Wolfe, 1995 *Bailliere's Clinical Rheumatology* "The epidemiology of drug treatment failure in rheumatoid arthritis," 9:619-632. (Exhibit 97).

Hochberg, et al., 1990 *Epidemiologic Reviews* "Epidemiology of Rheumatoid Arthritis: Update," 12:247-252. (Exhibit 98).

Spector, 1990 *Epidemiology of Rheumatic Disease* "Rheumatoid Arthritis," 16:513-537. (Exhibit 99).

Liu MF, Kohsaka H Sakurai H, Azuma m Okumura K Saito I, Miyasaka N, 1996, "The presence of costimulatory molecules B7.1 (CD80) and B7.2 (CD86) in rheumatoid arthritis synovium" *Arthritis-Rheum*. Jan.; 39(1): 110-4. (Exhibit 100).

Sfikakis PP, Via CS. 1997 "Expression of CD28, CTLA4, CD80, CD86 molecules in-patients with autoimmune rheumatic diseases: implications for immunotherapy". *Clin-Immunol-Immunopathol*. Jun.; 83(3): 195-8. (Exhibit 101).

Sayegh MH, Akalin E, Hancock WW, Russell ME, Carpenter CB, Linsley PS, Turka LA, 1995.*J. Exp. Med.*"CD28-B7 blockade after alloantisenic challenge in vivo inhibits Th1 cytokines but spares Th2". 181: 1869-1874. (Exhibits 102).

Racusen LC; et. al. 1999. "The Baniff 97 working classification of renal allograft pathology". *Kidney-Int*. 55(2): 713-723. (Exhibit 103).

Parkin D, Jacoby A, McNamme P, 2000. "Treatment of multiple sclerosis with interferon β: an appraisal of cost-effectiveness and quality of life" *J Neurol Neurosurg Psychiatry*; 68: 144-149. (Exhibit 104).

Nortvedt MW, Riise T, Myhr KM, and Nyland HI, 1999. "Quality of life in multiple sclerosis: measuring the disease effects more broadly" Neurology; 53(5): 1098-1103 (Exhibit 105).

Pearson TC, Alexander DZ, Winn KJ, Linsley PS, Lowry RP, Larsen CP, 1994. Transplantation tolerance induced by CTLA4-Ig. *Transplantation*, 57:1701-1706. (Exhibit 106).

Liao HX, Haynes BF, 1995. "Role of adhesion molecules in the pathogensis of rheumatoid arthritis" *Rheum-Dis-Clin-Noth-Am*. Aug.; 21(3): 715-40. (Exhibit 107).

Thomas R, Quinn C. 1996. "Functional differentiation of dendritic cells in rheumatoid arthritis: role of CD86 in the synovium" *J-Immunol*. Apr. 15; 156(8): 3074-86. (Exhibit 109).

Verhoeven-AC; Boers-M; Tugwell-P, 1998. "Combination therapy in rheumatoid arthritis: updated systematic review" *Br-J-Rheumatol*. Jun.;37 (6): 612-619 (Exhibit 110).

Schiff M, 1997. "Emerging treatments for rheumatoid arthritis" *Am-J-Med*. Jan. 27; 102 (1A): 11S-15S (Exhibit 111).

Balsa A, Dixey J, Sansom DM, Maddison PJ, Hall ND, 1996. "Differential expression of the costimulatory molecules B7.1 (CD80) and B7.2 (CD86) in rheumatoid synovial tissue" *Br-J-Rheumatol*. Jan.; 35(1): 33-7 (Exhibit 112).

Ranheim Ea, Kipps Tj, 1994. "Elevated expression of CD80 (B7/BB1) and other accessory molecules on synovial fluid mononuclear cell subsets in rheumatoid arthritis" *Arthritis-Rheum*. Nov.;37 (11): 1637-1647 (Exhibit 113).

Freeman, GJ, Gribben JG, Boussiotis VA, et. al. 1993. "Cloning of B7-2: a CTLA-4 counter receptor that costimulates human T cell proliferation" *Science*, 262: 909-911. (Exhibit 114).

Becker, J.C., Mar. 8, 2001, Abstract and of Presentation of "A multicenter, randomized, double-blind, placebo controlled study to evaluate the safety and preliminary clinical activity of multiple doses of CTLA4Ig and LEA29Y administration intravenously to subjects with rheumatoid arthritis," presented at American College of Rheumatology Conference: "2001 Innovative Therapies in Autoimmune Diseases," San Francisco, California (Exhibit 115).

Aruffo, S., Mar. 27, 2000, Presentation of "Approaches to Immune Regulation" at BIO 2000 in Boston, Mass. (Exhibit 116).

Abrams, et al., Sep. 4, 2000, *J.Exp.Med*. "Blockade of T Lymphocyte Costimulation with Cytotoxic T Lymphocyte- associated Antigen 4-Immunogloblin (CTLA4Ig) Reverse the Cellular Pathology of Psoriatic plaques, Including the Activation of Keratinocytes, Dendritic Cells, and Endothelial Cells," 192:681-693. (Exhibit 117).

Srinivas, N.R. et al., Dec. 1, 1995, *J.Pharmaceutical Sciences* "Pharmacokinetics and pharmacodynamics of CTLA4Ig (BMA-188667), a Novel Immunosuppressive Agent, in Monkeys following Multiple Doses," 85:1-4. (Exhibit 118).

Gandhi, et al., Nov. 18, 1998, Abstract and Presentation of *PharmSci Supplement* "Physical and Chemical Characterization of BMS-224818, A Recombinant Fusion Protein," in San Francisco, Ca. (Exhibit 119).

Flesher, A.R., Apr. 15, 1999, *Biological Process Sciences* Presentation of "Transgenic Production, A Comparative Study" at Bio 99 in Seattle, Washington. (Exhibit 120).

Greve, K.F., May 9, 1996, *J Chromatography* "Capillary electrophoretic examination of underivatized oligosaccharide mixtures released from immunoglobulin G anitbodies and CTLA4Ig fusion protein," 749:237-245. (Exhibit 121).

Srinivas, N.R., Apr. 8, 1997, *Pharmaceutical Research* "Assessment of Dose Proportionality, Absolute Bioavailability, and Immunogenicity Response of CTLAIg (BMS-188667), a Novel Immunosuppressive Agent, Following Subcutaneous and Intravenous Administration to Rats," 14:911-916. (Exhibit 122).

Weiner, R.S., Nov. 6-10, 1994, Abstract and Presentation of "Validation and PK Application of a Double Antibody Sandwich Enzyme Immunoassay For the Quantitation of Human CTLAIg Fusion Protein (BMS-188667) In Mouse Serum," (Exhibit 123).

Weiner, R.S., Jun. 6, 1996, *J Pharmaceutical and Biomedical Analysis* "A sensitive enzyme immunoassay for the quantitation of human CTLA4Ig fusion protien in mouse serum: pharmacokinetic application to optimizing cell line selection," 15:571-579. (Exhibit 124).

Warner, G.I. et al., Mar. 16-22, 1995, Abstract and Presentation of "Bioactivity of BMS-188667 (CTLAIg) in Cynomolgus Monkeys," in Seattle, Washington. (Exhibit 125).

Weiner, R.S., Mar. 1, 2000, Abstract and Presentation of "Industrial Perspectives of Primary Analytical Tools for Macromolecules- Principles and Applications with Examples." (Exhibit 126).

Weiner, R.S., Nov. 1995 Abstract and Presentation of "Validation of an Enzyme Immunoassay For The Quantition of Human CTLAIg Fusion Protein In Human Serum," in Miami, Florida. (Exhibit 127).

Weiner, R.S., Nov. 1995 Abstract and Presentation of "Automation and Validation of An EIA For Quantition of Human CTLAIg In Monkey Serum," in Miami, Florida. (Exhibit 128).

Webb, L.M.C. et al., Jul. 23, 1996 *Eur J Immunol* "Prevention and amelioration of collagen-induced arthritis by blocade of the CE28 co-stimulatory pathway: requirement for both B7-1 and B7-2" 26:2320-2328. (Exhibit 129).

Knoerzer, et al., May 5, 1995, *J Clin. Invest* "Collagen-induced Arthritis in the BB Rat Prevention of Disease by Treatment with CTLA4Ig" 96:987-993. (Exhibit 130).

Pearson et al., Apr. 27, 2000, Abstract of "Prolongation of Renal Allograft Survival with Blockade of the CD28 Pathway Using A Novel Mutant CTLA4-IG Fusion Protein In Non-Human Primates," in *Transplantation*, 69(8):#44, p. S123, Chicago, Il. (Exhibit 131).

Larsen, et al., May 13-17, 2000, A Presentation of "Prolongation of Renal Allograft Survival With Blockade of the CD28 Pathway Using A Novel Mutant CTLA4-Ig Protein In Nonhuman Primates" at the American Society of Transplantation Meeting in Chicago, Il. (Exhibit 132).

Larsen, Aug. 27-Sep. 1, 2000, A Presentation of "Manipulation of Costimulatory Pathways: Targeting CD80 and CD86" at the XVII congress of the Transplantation Society in Rome, Italy. (Exhibit 133).

Larsen, Mar. 3-4, 2000, A Presentation of "Manipulation of Costimulatory blockade: progress toward clinical application" at Canadian Society of Transplantation Annual Scientific meeting in Mont Tremblant, Quebec, Canada. (Exhibit 134).

Larsen, Jan. 13-17, 2000, A Presentation of "Costimulation blockade: Progress toward clinical application" at the American Society of Transplantation Meeting in Las Croabas, Puerto Rico. (Exhibit 135).

Hathcock, et al., Aug. 30, 1993 *Science* "Identification of an Alternative CTLA-4 Ligand Costimulatory for t Cell Activation," 262:905-911. (Exhibit 136).

Sfikakis, et al., Nov. 29, 1994 *Arthritis & Rheumatism* "CD28 Expression On T Cell Subsets in Vivo And CD28-Mediated T Cell Response In Vitro In Patients With Rheumatoid Arthritis," 38:649-654. (Exhibit 137).

Lakkis, Fadi G., et al., "Blocking the CD28-B7 T Cell Costimulation Pathway Induces Long Term Cardiac Allograft Acceptance in the Absence of IL-4[1]," *The Journal of Immunology*, 1997, 158:2443-2448. (Exhibit 140).

Pearson, Thomas C., et al., "Analysis of the B7 Costimulatory Pathway in Alllograft Rejection[1]," *Transplantation*, 1997, 63:1463-1469. (Exhibit 141).

Pearson, Thomas C., et al., "Transplantation Tolerance Induced by CTLA4-Ig[1]," *Transplantation*, 1994, 57:1701-1706. (Exhibit 142).

Alexander, Diane Z., "Analysis of a Functional Role for Chimerism in CTLA4-Ig Plus Bone Marrow-Treated Cardiac Allograft Recipients," *Transplantation*, 1994, 91:416-418. (Exhibit 143).

Larsen, Christian P., et al., "CD40-gp39 Interactions Play a Critical Role During Allofraft Rejection" *Transplantation*, 1996, 61:4-9. (Exhibit 144).

Pearson, Thomas C., et al., "CTLA4-Ig Plus Bone Marrow Induces Long-Term Allograft Survival and Donor-Specific Unresonsiveness in the Murine Model", *Transplantation*, 1996, 61:997-1004. (Exhibit 145).

Weber, C.J., et al., "CTLA4-Ig Prolongs Survival of Microencapsulted Rabbit Islet Xenografts in Spontaneously Diabetic Nod Mice," *Transplantation Proceedings*, 1996, 28:821-823. (Exhibit 146).

Alexander, D.Z., et al., "Analysis of effector mechanisms in murine cardiac allograft rejection," *Transplantation Immunology*, 1996, 4:46-48. (Exhibit 147).

Larsen, Christian P., et al., "Long-Term acceptance of skin and cardiac allografts after blocking CD40 and CD28 pathways," *Nature*, 1996, 381:434-438. (Exhibit 148).

Elwood, Eric T., et al., "Microchimerism and rejection in clinical transplantation," *The Lancet*, 1997, 349:1358-1360. (Exhibit 149).

Larsen, Christian P., and Thomas C. Pearson., "The CD40 pathway in allograft rejection, acceptance, and tolerance," *Transplantation*, 1997,9:641-647. (Exhibit 150).

Konieczny, Bogumila T.., et al., "IFN-γ Critical for Long-Term Allograft Survival Induced by Blocking the CD28 and CD40 Ligand T Cell Constimulation Pathways[1]," *The Journal of Immunology*, 1998,160:2059-2064. (Exhibit 151).

Elwood, Eric T., et al., "Prolonged Acceptance of Concordant and Discordant Xenografts With Combined CD40 and CD28 Pathway Blockade1" Transplantation, 1998,65:1422-1428. (Exhibit 152).

Niimi, Masanori, et al., "The Role of the CD40 Pathway in Alloantigen-Induced Hyporesoniveness in Vivo1," The Journal of Immunology, 1998,161:5331-5337. (Exhibit 153).

Whitmire, Jason K., et al., "CD40-CD40 Ligand Costimulation Is Required for Generating Antiviral CD4 T Cell Reponses But is Dispensable for T Cell Responses1," The Journal of Immunology, 1999,163:3194-3201. (Exhibit 154).

Bingaman, Adam W., et al., "Vigorous Allograft Rejection in the Absence of Danger1," Journal of Immunology, 2000,164:3056-3071. (Exhibit 155).

Bingaman, Adam W., et al., "Transplantation of the Bone Marrow Microenvironment Leads to Hematoppietic Chimerism Without Cytoreductive Conditioning," Transplantation, 2000, 69:2491-2496. (Exhibit 156).

Durham, Megan M., et al., "Cutting Edge: Administration of Anti-CD40 Ligand and Donor Bone Marrow Leads to Hemapoietic Chimerism and Donor-Specific Tolerance Without Cytoreductive Conditioning[1]," *Cutting Edge*, 2000,165:1-4. (Exhibit 157).

Williams, Matthew A., et al., "Genetic Characterization of Strain Differences in the Ability to Mediate CD40/CD28-Independent Rejection of Skin Allografts[1]," *The Journal of Immunology*, 2000, 165: 6549-6857. (Exhibit 158).

Bingaman, Adam W., et al., "The role of CD40L in T cell-dependent nitric oxide production by murine macrophages," *Transplant Immunology*, 2000, 8:195-202. (Exhibit 159).

Adams, Andrew B., et al., "Costimulation Blockade, Busulfan, and Bone Marrow Promote Titratable Macrochimerism, Induce Transplantation Tolerance, and Correct Genetic Hemoglobinopathies with Minimal Myelosuppression[1]," *The Journal of Immunology*, 2001, 167:1103-1111. (Exhibit 160).

Meng, L., "Blockade of the CD40 Pathway Fails to Prevent CD8 T Cell-Mediated Intestinal Allograft Rejection," *Transplantation Proceedings*, 2001, 33:418-420. (Exhibit 161).

Guo, Zhong., et al., "CD8 T Cell-Mediated Rejection of Intestinal Allografts is Resistant to Inhibition of the CD40/CD154 Costimulatory Pathway," *Transplantation*, 2001, 71:1351-1354. (Exhibit 162).

Ha, Jongwon, et al., "Aggressive skin allograft rejection in CD28-/- mice independent of the CD40/CD40L costimulatory pathway," *Transplant Immunology*,2001, 9:13-17. (Exhibit 163).

Bingaman, Adam W., et al., "Analysis of the CD40 and CD28 Pathways on Alloimmune Responses by CD4+ T Cells in Vivo[1]," *Transplantation*, 2001, 72:1286-1292. (Exhibit 164).

Adams, Andrew B., et al., "Calcineurin Inhibitor- Free CD28 Blockade-Based Protocol Protects Allogeneic Islets in Nonhuman Primates," *Diabetes*, 2002, 51:265-270. (Exhibit 165).

Whelchel, JD., et al. "Evolving Strategies in immunosuppressive Therapy: The Emory Experience," *Clinical Transplants*, 1996, 20:249-255 (Exhibit 166).

Ritichie, SC., et al., "Regulation of Immunostimulatory function and B7 molecule expression on murine dendritic cells," *Journal of Cellular Biochemistry*, 1995,21A:C1-215(Exhibit 167).

Alexander, DZ., et al., "Analysis of the mechanisms of CTLA4-Ig plus bone marrow induced transplantation tolerance," *Journal of Cellular Biochemistry*, 1995, 21A:C1-301 (Exhibit 168).

Alexander, DZ., et al., "CTLA4-Ig induced transplantation tolerance: analysis of donor cell chimerism," Surgical Forum, 1994, 45:402-403 (Exhibit 169).

Pearson, TC., et al., "CTLA4-Ig plus bone marrow induces transplantation tolerance in the murine model," Journal of Cellular Biochemistry, 1995, 21A:C1-327 (Exhibit 170).

Lakkis, FG., et al., "CTLA4Ig induces long-term cardiac allograft survival in the absence of interleukin-4," Journal of the American Society of Nephrology, 1996, 7:A3204 (Exhibit 171).

Morton, Philip A. et al., "Differential Effects of CTLA-4 Substitutions on the Binding of Human CD80 (B7-1) and CD86 (B7-2)," *Journal of Immunology*, 1996, 156:1047-1054 (Exhibit 189).

Sun, Hong et al., "Prevention of Chronic Rejection in Mouse Aortic Allografts by Combined Treatment with CTLA4-Ig and Anti-CD40 Ligand Monoclonal Antibody," *Transplantation*, 1997, 64:1838-56. (Exhibit 191).

Souza, D. et al., "Synergistic Inhibition of Established Collagen Induced Arthritis (CIA) Through Dual Inhibition of ICAM-1 and CD40L Pathways," *Arthritis and Rheumatism*, 1999, 42:S60 (Exhibit 192).

Blazar, Bruce R. et al., "Coblockade of the LFA1:ICAM and CD28/CTLA4:B7 Pathways Is A Highly Effective Means of Preventing Acute Lethal Graft-Versus-Host Disease Induced by Fully Major Histocompatibility Complex-Disparate Donor Grafts," *Blood*, 1995, 85:2607-18. (Exhibit 193).

Alegre, Maria-Luisa et al., "Immunomodulation of Transplant Rejection Using Monoclonal Antibodies and Soluble Receptors," Digestive Diseases and Sciences, 1995, 40:58-64. (Exhibit 196).

Murakami, Masaaki et al., "Identification and characterization of an alternative cytotoxic T lymphocyte-associated protein 4 binding molecule on B cells," *Proceedings of the National Academy of Sciences USA*, 1996, 93:7838-7842 (Exhibit 197).

Peach, Robert J. et al., "Both Extracellular Immunoglobin-like Domains of CD80 Contain Residues Critical for Binding T Cell Surface Receptros CTLA-4 and CD28," *Journal of Biological Chemistry*, 1995, 270:21181-21187. (Exhibit 198).

Fargeas, Christine et al., "Identification of Residues in the V Domain of CD80 (B7-1) Implicated in Functional Interactions with CD28 and CTLA4," *Journal of Experimental Medicine*, 1995, 182:667-675. (Exhibit 199).

Steurer, Wolfgang et al., "Ex Vivo Coating of Islet Cell Allografts with Murin CTLA4/Fc Promotes Graft Tolerance," *Journal of Immunology*, 1995, 155:1165-1174. (Exhibit 200).

Guo, Yong et al., "Mutational Analysis and an Alternatively Spliced Product of B7 Defines Its CD28/CTLA4-binding Site on Immunoglobulin C-like Domain," *Journal of Experimental Medicine*, 1995, 181:1345-1355. (Exhibit 201).

Peach, Robert J. and Peter S. Linsley, "CTLA4Ig: A Novel Immunoglobulin Chimera with Immunosuppressive Properties," *Methods*, 1995, 8:116-123. (Exhibit 202).

Rattis, Frédérique-Marie et al., "Expression and function of B7-1 (CD80) and B7-2 (CD86) on human epidermal Langerhans cells," *European Journal of Immunology*, 1996, 26:449-453. (Exhibit 203).

Najafian, Nader and Mohamed H. Sayegh, "CTLA4-Ig: a novel immunosuppressive agent," *Exp. Opin. Invest. Drugs*, 2000, 9:2147-2157 (Exhibit 206).

Schwartz, R., "Costimulation of T Lymphocytes: The Role of CD28, CTLA-4, and B7/BB1 in Interleukin-2 Production and Immunotherapy," *Cell*, 1992, 71:1085-1088. (Exhibit 215).

Bluestone, Jeffrey A., "New Perspectives of CD28-B7-Mediated T Cell Costimulation," *Immunity*, 1995, 2:555-9 (Exhibit 221).

Bluestone, J. A. et al., "Costimulation and its role in organ transplantation," *Clin. Transplantation*, 1996, 10:104-9 (Exhibit 222).

Chen, Fang-An et al., "Human Antibody Response in Human Peripheral Blood Leukocyte/Severe Combined Immunodeficient Chimeric Model is Dependent on B and T Cell Costimulation via CD40/CD40 Ligand," *Journal of Immunology*, 1995, 155:2833-40 (Exhibit 223).

Durie, Fiona H. et al., "Prevention of Collagen-Induced Arthritis with an Antibody to gp39, the Ligand for CD40," *Science*, 1993, 261:1328-30 (Exhibit 224).

Durie, Fiona H. et al., "Antibody to the Ligand of CD40, gp39, Blocks the Occurence of the Acute and Chronic Forms of Graft-vs-Host Disease," *Journal of Clinical Investigation*, 1994, 94:1333-8 (Exhibit 225).

Griggs, Nathan et al., "Contribution of CD28/CTLA4/B7 and gp39/CD40 Costimulation Pathways in Clonal Expansion and Functional Acquisition of Self Reactive T Cells," *Journal of Cellular Biochemistry*, 1995, Supplement, p. 141, Abstract C2-427 (Exhibit 226).

Jenkins, Marc K. et al., "CD28 Delivers a Costimulatory Signal Involved in Antigen-Specific IL-2 Production by Human T Cells," *Journal of Immunology*, 1991, 147:2461-6 (Exhibit 227).

Lenschow, Deborah J. et al., "Inhibition of Transplant Rejection Following Treatment with Anti-B7-2 and Anti-B7-1 Antibodies," *Transplantation*, 1995, 60:1171-8 (Exhibit 228).

Rossini, Aldo A. et al., "Induction of Immunological Tolerance to Islet Allografts," *Cell Transplantation*, 1996, 5:49-52 (Exhibit 229).

Roy, Meenakshi et al., "Studies on the interdependence of gp39 and B7 expression and function during antigen-specific immune response," *European Journal of Immunology*, 1995, 25:596-603 (Exhibit 230).

Schaub, M. et al., "Synergistic effect of CD40L/CD40 and CD28/B7 Blockade in murine EAE," *Journal of Allergy and Clinical Immunology*, 1997, 99:S206, Abstract 834 (Exhibit 231).

Tang, Aimin et al., "Suppression of Murine Allergic Contact Dermatitis by CTLA4Ig: Tolerance Induction of Th2 Responses Requires Additional Blockade of CD40-Ligand," *Journal of Immunology*, 1996, 157:117-25 (Exhibit 232).

Gallon, L. et al., "Differential Effects of B7-1 Blockade in the Rat Experimental Autoimmune Encephalomyelitis Model", The J. of Immunology, vol. 159, pp. 4212-4216 (1997).

Khoury, S. et al., Ex Vivo Treatment of Antigen-Presenting Cells with CTLA4Ig and Encephalitogenic Peptide Prevents Experimental Autoimmune Encephalomyelitis in the Lewis Rat, The J. of Immunology, vol. 157, pp. 3700-3705 (1996).

Lin, H. et al., :CD28 blockade alters cytokine mRNA profiles in cardiac transplantation, Surgery, vol. 122(2) pp. 129-137 (1997).

Wagener, M. et al., "Alloantigen-Driven T Cell Death Mediated by Fas Figand and Tumor Necrosis Factor-[alpha] is not essential for the induction of Allograft Acceptance", Transplantation, vol. 69(11), pp. 2428-2432 (2000).

Croft, M. et al., "Naïve Versus memory CD4 T Cell Response to Antigen", Journal of Immunology, vol. 152, pp. 2675-2685 (1994).

Cush, JJ. Et al., "Cellular basis for rheumatoid inflammation", Clin. Orthop Relat Res., vol. 265, pp. 9-22 (1991).

Dougados, M. et al., "Abatacept provides increasing improvements in clinical measures of disease activity over time: results from the aim trial", Ann Rheum Dis, vol. 66(Suppl II) p. 429 (2007).

Dougados, M. et al., "Efficacy of Abatacept or infliximab treatment in rheumatoid arthritis patients with an inadequate response to methotrexate", Ann Rheum Dis, vol. 66(Suppl II), p. 88 (2007).

Dougados, M. et al., "Abatacept reduces fatigue and pain severity and sleep problems through 2 years in rheumatoid arthritis patients in the aim and attain trails", Ann Rheum Dis, vol. 66(Suppl II), p. 429 (2007).

Hegen, M. et al., "Utility of animal models for identification of potential therapeutics for Rheumatoid Arthritis", Ann Rheum Dis, ARD Online published Nov. 29, 2007.

Isaacs, J., "T Cell immunomodulation-the Holy Grail of therapeutic tolerance", Current opinion in Pharmacology, vol. 7, pp. 418-425 (2007).

Malmstrom, V. et al., "Modulating co-stimulation: a rational strategy in the treatment of rheumatoid arthritis?", Arthritis Res Ther, vol. 7(Suppl 2), p. S15-S20, (2005).

Qin, S. et al., ""Infectious"transplantation tolerance" , Science, vol. 259(5097), pp. 974-977 (1993).

Sibilia, J. et al., "Sustained improvements in disease activity score 28 )DAS28) and patient (PT)-reported outcomes (PRO) with abatacept (ABA) in Rheumatoid arthritis (RA) PTS with an inadequate response to anti-TNF Therapy: the long-term extension (LTE) of the attain trial", Ann Rheum Dis, vol. 65(Suppl II), p. 501 (2006).

Wells, G.A. et al., "Minimal disease activity state for patients with Rheumatoid arthritis treated with abatacept", Ann Rheum Dis, vol. 66(Suppl II), p. 341 (2007).

Keystone, E., "Abandoned therapies and unpublished trials in rheumatoid arthritis", Opin Rheumatol., vol. 15, pp. 253-258 (2003).

\* cited by examiner

Demographic -1-

| | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|
| Gender Male | 6 (19%) | 4 (15%) | 9 (28%) | 10 (31%) | 9 (28%) | 9 (31%) | 7 (23%) | 54 (25%) |
| Female | 26 (81%) | 22 (85%) | 23 (72%) | 22 (69%) | 23 (72%) | 20 (69%) | 24 (77%) | 160 (75%) |
| Race White | 30 (94%) | 23 (88%) | 30 (94%) | 30 (94%) | 29 (91%) | 25 (86%) | 27 (87%) | 194 (91%) |
| Black | 2 (6%) | 0 (0%) | 0 (0%) | 1 (3%) | 1 (3%) | 3 (10%) | 2 (6%) | 9 (4%) |
| Other | 0 (0%) | 3 (12%) | 2 (6%) | 1 (3%) | 2 (6%) | 1 (3%) | 2 (6%) | 11 (5%) |
| Disease Duration < 2 years | 12 (38%) | 5 (19%) | 8 (25%) | 12 (38%) | 10 (31%) | 10 (34%) | 11 (35%) | 68 (32%) |
| 2-5 years | 14 (44%) | 11 (42%) | 18 (56%) | 13 (41%) | 14 (44%) | 14 (48%) | 12 (39%) | 96 (45%) |
| 5-7 years | 6 (19%) | 8 (31%) | 6 (19%) | 6 (19%) | 6 (19%) | 5 (17%) | 7 (23%) | 44 (21%) |
| > 7 years | 0 (0%) | 2 (8%) | 0 (0%) | 1 (3%) | 2 (6%) | 0 (0%) | 1 (3%) | 6 (3%) |
| Duration Disease (years) N | 32 | 26 | 32 | 32 | 32 | 29 | 31 | 214 |
| Mean | 3.2 | 4.2 | 3.3 | 3.4 | 3.7 | 3.1 | 3 | 3.4 |
| Sd | 2 | 2 | 1.7 | 2.1 | 2 | 1.8 | 2.2 | 2 |
| Min | 0.3 | 0.2 | 0.4 | 0 | 0.7 | 0.4 | 0 | 0 |
| Max | 7 | 7.5 | 6.8 | 7.3 | 7.6 | 7 | 7.1 | 7.6 |

FIG. 1A

Demographic -2-

| | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|
| Gender | | | | | | | | |
| Male | 6 (19%) | 4 (15%) | 9 (28%) | 10 (31%) | 9 (28%) | 9 (31%) | 7 (23%) | 54 (25%) |
| Female | 26 (81%) | 22 (85%) | 23 (72%) | 22 (69%) | 23 (72%) | 20 (69%) | 24 (77%) | 160 (75%) |
| Age | | | | | | | | |
| N | 32 | 26 | 32 | 32 | 32 | 29 | 31 | 214 |
| Mean | 48.3 | 46.9 | 46.2 | 51.5 | 49.3 | 50.8 | 45.6 | 48.4 |
| Sd | 11.7 | 12.2 | 13.4 | 11.5 | 8.8 | 10.7 | 10.1 | 11.3 |
| Min | 22 | 25 | 21 | 24 | 27 | 24 | 28 | 21 |
| Max | 66 | 64 | 64 | 66 | 66 | 65 | 64 | 66 |
| Weight (kg) | | | | | | | | |
| N | 32 | 26 | 32 | 32 | 32 | 29 | 31 | 214 |
| Mean | 72.9 | 70.6 | 72.7 | 70 | 69.8 | 68.9 | 71.7 | 71 |
| Sd | 13.5 | 17.4 | 14.4 | 16.7 | 12.8 | 12.1 | 15.8 | 14.6 |
| Min | 46.7 | 45 | 50 | 40.1 | 48 | 47 | 39.2 | 39.2 |
| Max | 98.2 | 101.3 | 99 | 101.3 | 95 | 93.8 | 99 | 101.3 |
| Disease activity (patient) | | | | | | | | |
| N | 32 | 26 | 32 | 32 | 32 | 29 | 31 | 215 |
| Mean | 3.6 | 3.6 | 3.7 | 3.6 | 3.5 | 3.6 | 3.5 | 3.6 |
| Sd | 0.9 | 0.9 | 0.9 | 0.9 | 0.8 | 0.8 | 0.7 | 0.8 |
| Min | 2 | 2 | 2 | 2 | 2 | 2 | 2 | 2 |
| Max | 5 | 5 | 5 | 5 | 5 | 5 | 5 | 5 |

FIG. 1B

Demographic - Disease

| | | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|---|
| Disease activity (physician) | N | 32 | 26 | 32 | 32 | 32 | 29 | 31 | 214 |
| | Mean | 3.6 | 3.5 | 3.5 | 3.7 | 3.4 | 3.4 | 3.5 | 3.5 |
| | Sd | 0.7 | 0.6 | 0.8 | 1 | 0.6 | 0.8 | 0.6 | 0.7 |
| | Min | 2 | 3 | 2 | 2 | 2 | 2 | 3 | 2 |
| | Max | 5 | 5 | 5 | 5 | 5 | 5 | 5 | 5 |
| ESR | N | 32 | 26 | 32 | 32 | 32 | 29 | 30 | 213 |
| | Mean | 43.3 | 35.2 | 41.6 | 36.3 | 29.8 | 40.9 | 39.3 | 38.1 |
| | Sd | 29.4 | 22.5 | 27.4 | 27.9 | 24.2 | 30.2 | 24.6 | 26.8 |
| | Min | 2 | 4 | 4 | 3 | 0 | 6 | 2 | 0 |
| | Max | 116 | 90 | 94 | 98 | 91 | 110 | 102 | 116 |
| Physical function (score) | N | 32 | 26 | 31 | 32 | 32 | 29 | 31 | 213 |
| | Mean | 16.8 | 15.5 | 16.2 | 17.1 | 15.3 | 16.3 | 16.1 | 16.2 |
| | Sd | 5.4 | 4.2 | 5.5 | 5.7 | 3.7 | 4.8 | 3.8 | 4.8 |
| | Min | 8 | 8 | 8 | 8 | 8 | 8 | 9 | 8 |
| | Max | 32 | 23 | 26 | 28 | 24 | 26 | 26 | 32 |
| CRP | N | 30 | 23 | 31 | 31 | 31 | 28 | 31 | 205 |
| | Mean | 56.7 | 26.4 | 48 | 33.6 | 28.1 | 48.1 | 37.5 | 40.1 |
| | Sd | 62.7 | 30.3 | 47.3 | 46 | 39.1 | 64.5 | 35.2 | 48.6 |
| | Min | 2 | 5 | 3 | 3 | 3 | 3 | 3 | 2 |
| | Max | 248 | 115 | 198 | 182 | 200 | 333 | 135 | 333 |

FIG. 1C

Demographic - Disease

|  |  | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|---|
| Tender joints (score) | N | 32 | 26 | 32 | 32 | 32 | 29 | 31 | 214 |
|  | Mean | 32.1 | 32.5 | 32.1 | 29.4 | 25.6 | 30.7 | 30.6 | 30.4 |
|  | Sd | 14.8 | 14.8 | 15 | 14.6 | 12 | 13.3 | 12.9 | 13.9 |
|  | Min | 12 | 14 | 11 | 12 | 12 | 12 | 12 | 11 |
|  | Max | 63 | 64 | 68 | 68 | 61 | 63 | 59 | 68 |
| Swollen joints (score) | N | 32 | 26 | 32 | 32 | 32 | 29 | 31 | 214 |
|  | Mean | 23.9 | 18.6 | 26.9 | 22.7 | 18.3 | 22.6 | 19.9 | 21.9 |
|  | Sd | 10 | 6.3 | 11.4 | 12.7 | 7.6 | 8.5 | 8.9 | 10 |
|  | Min | 10 | 10 | 10 | 10 | 10 | 10 | 10 | 10 |
|  | Max | 51 | 33 | 53 | 58 | 36 | 40 | 44 | 58 |
| Pain (score) | N | 32 | 26 | 32 | 32 | 32 | 29 | 31 | 214 |
|  | Mean | 3.5 | 3.4 | 3.5 | 3.5 | 3.5 | 3.3 | 3.5 | 3.5 |
|  | Sd | 0.9 | 0.6 | 0.6 | 1 | 0.7 | 0.8 | 0.7 | 0.8 |
|  | Min | 2 | 2 | 2 | 1 | 2 | 2 | 3 | 1 |
|  | Max | 5 | 5 | 5 | 5 | 5 | 5 | 5 | 5 |
| AM stiffness (min.) | N | 31 | 26 | 32 | 31 | 32 | 29 | 30 | 211 |
|  | Mean | 156.6 | 211.5 | 145.2 | 149.5 | 160.9 | 160.3 | 147.5 | 160.5 |
|  | Sd | 121.5 | 370.6 | 102.1 | 148.7 | 151.1 | 152.3 | 258.3 | 198.1 |
|  | Min | 30 | 0 | 5 | 35 | 30 | 0 | 15 | 0 |
|  | Max | 600 | 1440 | 420 | 720 | 600 | 720 | 1440 | 1440 |

FIG. 1D

Demographic - Prior treatments -

| | | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|---|
| Etanercept | Yes | 0 (0%) | 0 (0%) | 0 (0%) | 0 (0%) | 0 (0%) | 0 (0%) | 0 (0%) | 0 (0%) |
| | No | 32 (100%) | 26 (100%) | 32 (100%) | 32 (100%) | 32 (100%) | 29 (100%) | 31 (100%) | 214 (100%) |
| Methotrexate | Yes | 23 (72%) | 22 (85%) | 26 (81%) | 24 (75%) | 24 (75%) | 21 (72%) | 28 (90%) | 168 (79%) |
| | No | 9 (28%) | 4 (15%) | 6 (19%) | 8 (25%) | 8 (25%) | 8 (28%) | 3 (10%) | 46 (21%) |
| Other DMARDs | Yes | 28 (86%) | 23 (88%) | 25 (78%) | 26 (81%) | 28 (86%) | 24 (83%) | 25 (81%) | 179 (84%) |
| | No | 4 (13%) | 3 (12%) | 7 (22%) | 6 (19%) | 4 (13%) | 5 (17%) | 6 (19%) | 35 (16%) |
| C-Steroids | Yes | 31 (97%) | 26 (100%) | 29 (91%) | 27 (84%) | 27 (84%) | 28 (97%) | 24 (77%) | 192 (90%) |
| | No | 1 (3%) | 0 (0%) | 3 (9%) | 5 (16%) | 5 (16%) | 1 (3%) | 7 (23%) | 22 (10%) |
| NSAIDs | Yes | 27 (84%) | 20 (77%) | 30 (94%) | 29 (91%) | 26 (81%) | 25 (86%) | 25 (77%) | 181 (85%) |
| | No | 5 (16%) | 6 (23%) | 2 (6%) | 3 (9%) | 6 (19%) | 4 (14%) | 7 (23%) | 33 (15%) |
| Other | Yes | 30 (94%) | 22 (85%) | 29 (91%) | 30 (94%) | 31 (97%) | 29 (100%) | 29 (94%) | 200 (93%) |
| | No | 2 (6%) | 4 (15%) | 3 (9%) | 2 (6%) | 1 (3%) | 0 (0%) | 2 (6%) | 14 (7%) |

FIG. 1E

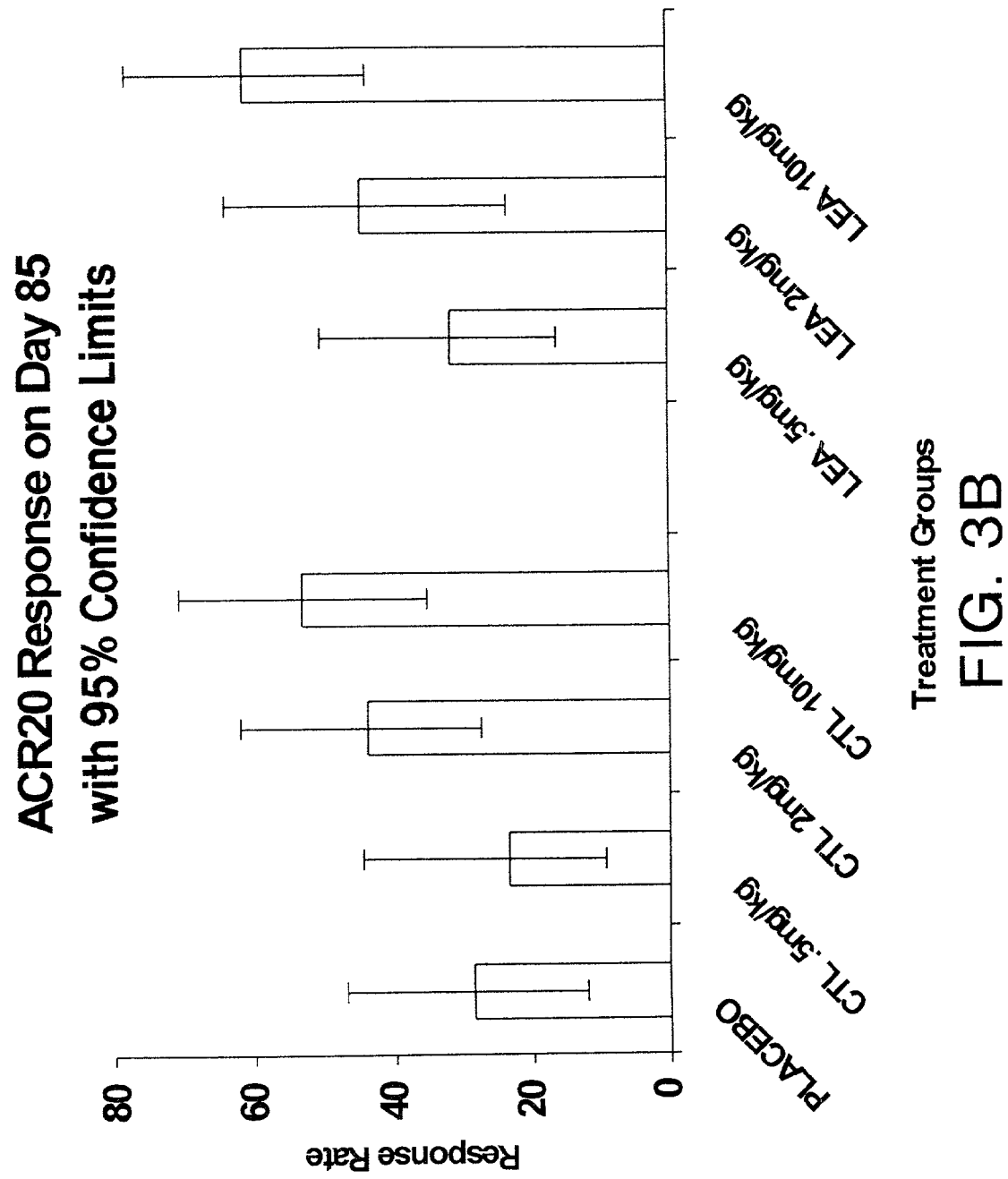

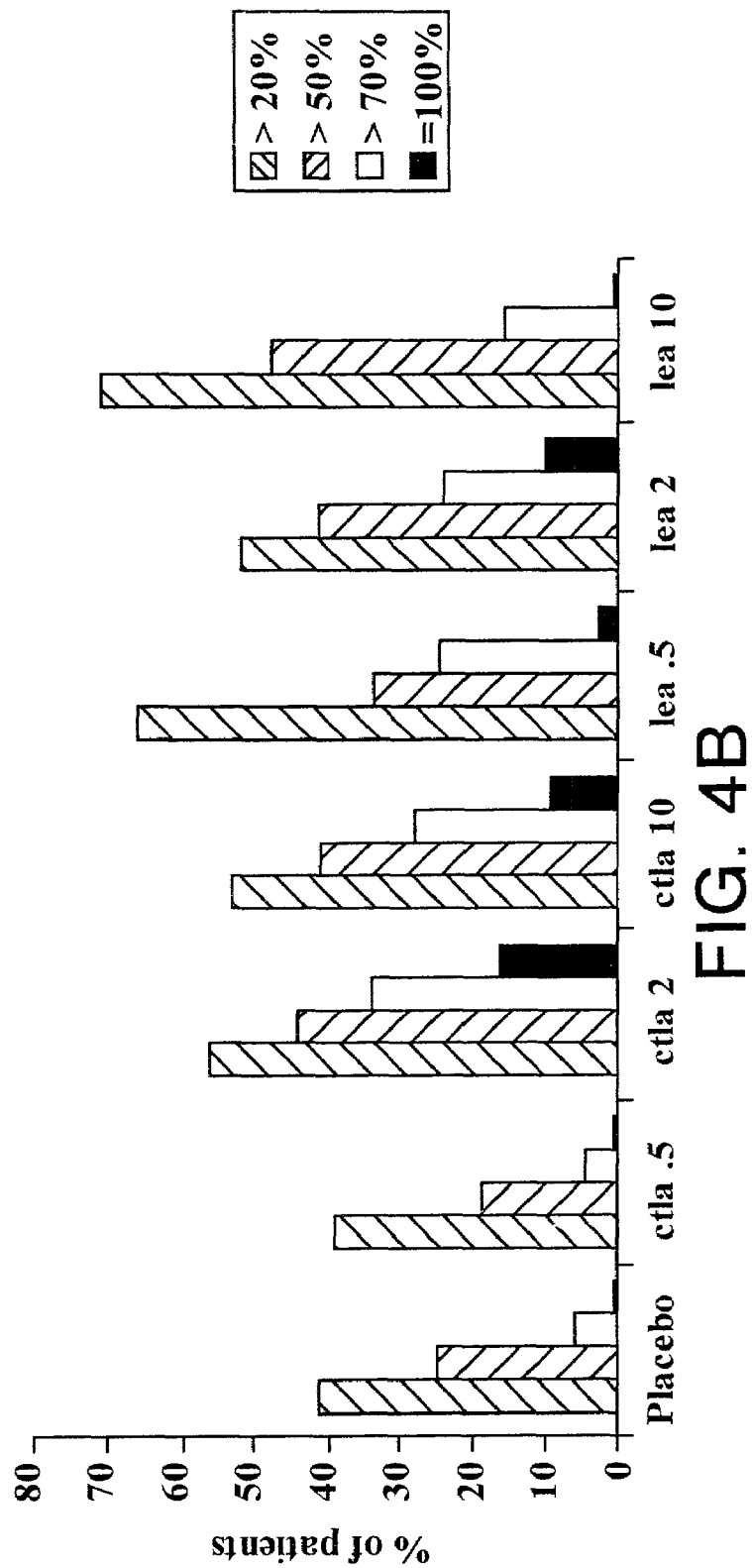

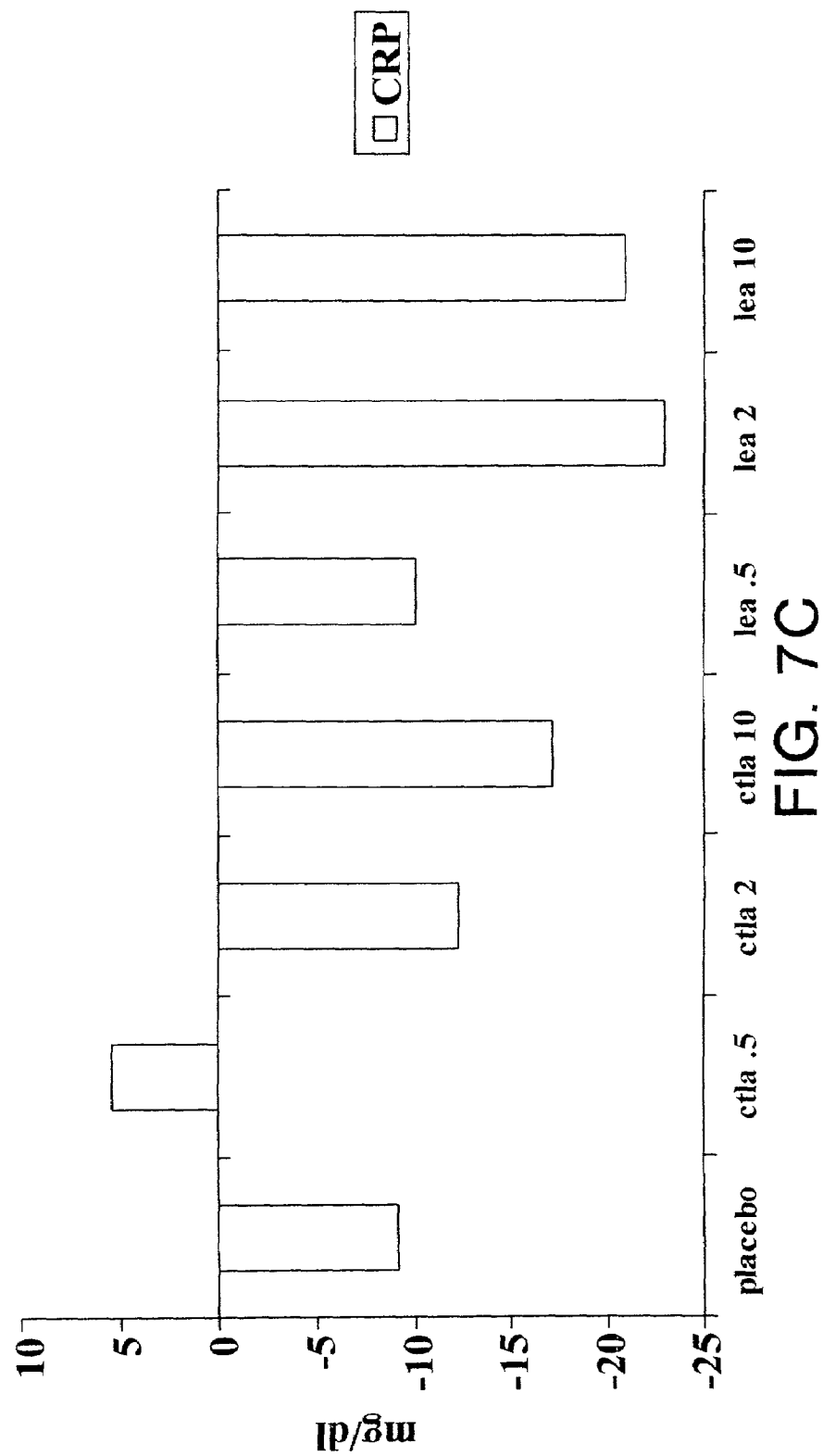

```
ATGGGTGTACTGCTCACACAGAGGACGCTGCTCAGTCTGGTCCTTGCACTCCTGTTTCCA      -19
M~~G~~V~~L~~L~~T~~Q~~R~~T~~L~~L~~S~~L~~V~~L~~A~~L~~L~~F~~P~~       -7

AGCATGGCGAGCATGGCAATGCACGTGGCCCAGCCTGCTGTGGTACTGGCCAGCAGCCGA      +42
S~~M~~A~~S~~M~~A~~M~~H~~V~~A~~Q~~P~~A~~V~~V~~L~~A~~S~~S~~R~~      +14
                +1

GGCATCGCTAGCTTTGTGTGTGAGTATGCATCTCCAGGCAAAGCCACTGAGGTCCGGGTG     +102
G~~I~~A~~S~~F~~V~~C~~E~~Y~~A~~S~~P~~G~~K~~A~~T~~E~~V~~R~~V~~      +34

ACAGTGCTTCGGCAGGCTGACAGCCAGGTGACTGAAGTCTGTGCGGCAACCTACATGATG     +162
T~~V~~L~~R~~Q~~A~~D~~S~~Q~~V~~T~~E~~V~~C~~A~~A~~T~~Y~~M~~M~~      +54

GGGAATGAGTTGACCTTCCTAGATGATTCCATCTGCACGGGCACCTCCAGTGGAAATCAA     +222
G~~N~~E~~L~~T~~F~~L~~D~~D~~S~~I~~C~~T~~G~~T~~S~~S~~G~~N~~Q~~      +74

GTGAACCTCACTATCCAAGGACTGAGGGCCATGGACACGGGACTCTACATCTGCAAGGTG     +282
V~~N~~L~~T~~I~~Q~~G~~L~~R~~A~~M~~D~~T~~G~~L~~Y~~I~~C~~K~~V~~      +94

GAGCTCATGTACCCACCGCCATACTACGAGGGCATAGGCAACGGAACCCAGATTTATGTA     +342
E~~L~~M~~Y~~P~~P~~P~~Y~~Y~~E~~G~~I~~G~~N~~G~~T~~Q~~I~~Y~~V~~     +114

ATTGATCCAGAACCGTGCCCAGATTCTGATCAGGAGCCCAAATCTTCTGACAAAACTCAC     +402
I~~D~~P~~E~~P~~C~~P~~D~~S~~D~~Q~~E~~P~~K~~S~~S~~D~~K~~T~~H~~     +134

ACATCCCCACCGTCCCCAGCACCTGAACTCCTGGGGGGATCGTCAGTCTTCCTCTTCCCC     +462
T~~S~~P~~P~~S~~P~~A~~P~~E~~L~~L~~G~~G~~S~~S~~V~~F~~L~~F~~P~~     +154

CCAAAACCCAAGGACACCCTCATGATCTCCCGGACCCCTGAGGTCACATGCGTGGTGGTG     +522
P~~K~~P~~K~~D~~T~~L~~M~~I~~S~~R~~T~~P~~E~~V~~T~~C~~V~~V~~V~~     +174

GACGTGAGCCACGAAGACCCTGAGGTCAAGTTCAACTGGTACGTGGACGGCGTGGAGGTG     +582
D~~V~~S~~H~~E~~D~~P~~E~~V~~K~~F~~N~~W~~Y~~V~~D~~G~~V~~E~~V~~     +194

CATAATGCCAAGACAAAGCCGCGGGAGGAGCAGTACAACAGCACGTACCGTGTGGTCAGC     +642
H~~N~~A~~K~~T~~K~~P~~R~~E~~E~~Q~~Y~~N~~S~~T~~Y~~R~~V~~V~~S~~     +214

GTCCTCACCGTCCTGCACCAGGACTGGCTGAATGGCAAGGAGTACAAGTGCAAGGTCTCC     +702
V~~L~~T~~V~~L~~H~~Q~~D~~W~~L~~N~~G~~K~~E~~Y~~K~~C~~K~~V~~S~~     +234

AACAAAGCCCTCCCAGCCCCCATCGAGAAAACCATCTCCAAAGCCAAAGGGCAGCCCCGA     +762
N~~K~~A~~L~~P~~A~~P~~I~~E~~K~~T~~I~~S~~K~~A~~K~~G~~Q~~P~~R~~     +254

GAACCACAGGTGTACACCCTGCCCCCATCCCGGGATGAGCTGACCAAGAACCAGGTCAGC     +822
E~~P~~Q~~V~~Y~~T~~L~~P~~P~~S~~R~~D~~E~~L~~T~~K~~N~~Q~~V~~S~~     +274

CTGACCTGCCTGGTCAAAGGCTTCTATCCCAGCGACATCGCCGTGGAGTGGGAGAGCAAT     +882
L~~T~~C~~L~~V~~K~~G~~F~~Y~~P~~S~~D~~I~~A~~V~~E~~W~~E~~S~~N~~     +294

GGGCAGCCGGAGAACAACTACAAGACCACGCCTCCCGTGCTGGACTCCGACGGCTCCTTC     +942
G~~Q~~P~~E~~N~~N~~Y~~K~~T~~T~~P~~P~~V~~L~~D~~S~~D~~G~~S~~F~~     +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~     +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~     +354

CCGGGTAAATGA
P~~G~~K~~*
```

FIG. 18

```
ATGGGTGTACTGCTCACACAGAGGACGCTGCTCAGTCTGGTCCTTGCACTCCTGTTTCCA        -19
M~~G~~V~~L~~L~~T~~Q~~R~~T~~L~~L~~S~~L~~V~~L~~A~~L~~L~~F~~P~~         -7

AGCATGGCGAGCATGGCAATGCACGTGGCCCAGCCTGCTGTGGTACTGGCCAGCAGCCGA        +42
S~~M~~A~~S~~M~~A~~M~~H~~V~~A~~Q~~P~~A~~V~~V~~L~~A~~S~~S~~R~~        +14
    +1

GGCATCGCTAGCTTTGTGTGTGAGTATGCATCTCCAGGCAAATATACTGAGGTCCGGGTG       +102
G~~I~~A~~S~~F~~V~~C~~E~~Y~~A~~S~~P~~G~~K~~Y~~T~~E~~V~~R~~V~~        +34

ACAGTGCTTCGGCAGGCTGACAGCCAGGTGACTGAAGTCTGTGCGGCAACCTACATGATG       +162
T~~V~~L~~R~~Q~~A~~D~~S~~Q~~V~~T~~E~~V~~C~~A~~A~~T~~Y~~M~~M~~        +54

GGGAATGAGTTGACCTTCCTAGATGATTCCATCTGCACGGGCACCTCCAGTGGAAATCAA       +222
G~~N~~E~~L~~T~~F~~L~~D~~D~~S~~I~~C~~T~~G~~T~~S~~S~~G~~N~~Q~~        +74

GTGAACCTCACTATCCAAGGACTGAGGGCCATGGACACGGGACTCTACATCTGCAAGGTG       +282
V~~N~~L~~T~~I~~Q~~G~~L~~R~~A~~M~~D~~T~~G~~L~~Y~~I~~C~~K~~V~~        +94

GAGCTCATGTACCCACCGCCATACTACGAGGGCATAGGCAACGGAACCCAGATTTATGTA       +342
E~~L~~M~~Y~~P~~P~~P~~Y~~Y~~E~~G~~I~~G~~N~~G~~T~~Q~~I~~Y~~V~~       +114

ATTGATCCAGAACCGTGCCCAGATTCTGATCAGGAGCCCCAAATCTTCTGACAAAACTCAC       +402
I~~D~~P~~E~~P~~C~~P~~D~~S~~D~~Q~~E~~P~~K~~S~~S~~D~~K~~T~~H~~       +134

ACATCCCCACCGTCCCCAGCACCTGAACTCCTGGGGGGATCGTCAGTCTTCCTCTTCCCC       +462
T~~S~~P~~P~~S~~P~~A~~P~~E~~L~~L~~G~~G~~S~~S~~V~~F~~L~~F~~P~~       +154

CCAAAACCCAAGGACACCCTCATGATCTCCCGGACCCCTGAGGTCACATGCGTGGTGGTG       +522
P~~K~~P~~K~~D~~T~~L~~M~~I~~S~~R~~T~~P~~E~~V~~T~~C~~V~~V~~V~~       +174

GACGTGAGCCACGAAGACCCTGAGGTCAAGTTCAACTGGTACGTGGACGGCGTGGAGGTG       +582
D~~V~~S~~H~~E~~D~~P~~E~~V~~K~~F~~N~~W~~Y~~V~~D~~G~~V~~E~~V~~       +194

CATAATGCCAAGACAAAGCCGCGGGAGGAGCAGTACAACAGCACGTACCGTGTGGTCAGC       +642
H~~N~~A~~K~~T~~K~~P~~R~~E~~E~~Q~~Y~~N~~S~~T~~Y~~R~~V~~V~~S~~       +214

GTCCTCACCGTCCTGCACCAGGACTGGCTGAATGGCAAGGAGTACAAGTGCAAGGTCTCC       +702
V~~L~~T~~V~~L~~H~~Q~~D~~W~~L~~N~~G~~K~~E~~Y~~K~~C~~K~~V~~S~~       +234

AACAAAGCCCTCCCAGCCCCCATCGAGAAAACCATCTCCAAAGCCAAAGGGCAGCCCCGA       +762
N~~K~~A~~L~~P~~A~~P~~I~~E~~K~~T~~I~~S~~K~~A~~K~~G~~Q~~P~~R~~       +254

GAACCACAGGTGTACACCCTGCCCCCATCCCGGGATGAGCTGACCAAGAACCAGGTCAGC       +822
E~~P~~Q~~V~~Y~~T~~L~~P~~P~~S~~R~~D~~E~~L~~T~~K~~N~~Q~~V~~S~~       +274

CTGACCTGCCTGGTCAAAGGCTTCTATCCCAGCGACATCGCCGTGGAGTGGGAGAGCAAT       +882
L~~T~~C~~L~~V~~K~~G~~F~~Y~~P~~S~~D~~I~~A~~V~~E~~W~~E~~S~~N~~       +294

GGGCAGCCGGAGAACAACTACAAGACCACGCCTCCCGTGCTGGACTCCGACGGCTCCTTC       +942
G~~Q~~P~~E~~N~~N~~Y~~K~~T~~T~~P~~P~~V~~L~~D~~S~~D~~G~~S~~F~~       +314

TTCCTCTACAGCAAGCTCACCGTGGACAAGAGCAGGTGGCAGCAGGGGAACGTCTTCTCA      +1002
F~~L~~Y~~S~~K~~L~~T~~V~~D~~K~~S~~R~~W~~Q~~Q~~G~~N~~V~~F~~S~~       +334

TGCTCCGTGATGCATGAGGCTCTGCACAACCACTACACGCAGAAGAGCCTCTCCCTGTCT      +1062
C~~S~~V~~M~~H~~E~~A~~L~~H~~N~~H~~Y~~T~~Q~~K~~S~~L~~S~~L~~S~~       +354

CCGGGTAAATGA
P~~G~~K~~*
```

FIG. 19

```
ATGGGTGTACTGCTCACACAGAGGACGCTGCTCAGTCTGGTCCTTGCACTCCTGTTTCCA
M   G   V   L   L   T   Q   R   T   L   L   S   L   V   L   A   L   L   F   P

AGCATGGCGAGCATGGCAATGCACGTGGCCCAGCCTGCTGTGGTACTGGCCAGCAGCCGA
S   M   A   S   M   A   M   H   V   A   Q   P   A   V   V   L   A   S   S   R

GGCATCGCTAGCTTTGTGTGTGAGTATGCATCTCCAGGCAAATTGACTGAGGTCCGGGTG
G   I   A   S   F   V   C   E   Y   A   S   P   G   K   L   T   E   V   R   V

ACAGTGCTTCGGCAGGCTGACAGCCAGGTGACTGAAGTCTGTGCGGCAACCTACATGATG
T   V   L   R   Q   A   D   S   Q   V   T   E   V   C   A   A   T   Y   M   M

GGGAATGAGTTGACCTTCCTAGATGATTCCATCTGCACGGGCACCTCCAGTGGAAATCAA
G   N   E   L   T   F   L   D   D   S   I   C   T   G   T   S   S   G   N   Q

GTGAACCTCACTATCCAAGGACTGAGGGCCATGGACACGGGACTCTACATCTGCAAGGTG
V   N   L   T   I   Q   G   L   R   A   M   D   T   G   L   Y   I   C   K   V

GAGCTCATGTACCCACCGCCATACTACGAGGGCATAGGCAACGGAACCCAGATTTATGTA
E   L   M   Y   P   P   P   Y   Y   E   G   I   G   N   G   T   Q   I   Y   V

ATTGATCCAGAACCGTGCCCAGATTCTGATCAGGAGCCCAAATCTTCTGACAAAACTCAC
I   D   P   E   P   C   P   D   S   D   Q   E   P   K   S   S   D   K   T   H

ACATCCCCACCGTCCCCAGCACCTGAACTCCTGGGGGGATCGTCAGTCTTCCTCTTCCCC
T   S   P   P   S   P   A   P   E   L   L   G   G   S   S   V   F   L   F   P

CCAAAACCCAAGGACACCCTCATGATCTCCCGGACCCCTGAGGTCACATGCGTGGTGGTG
P   K   P   K   D   T   L   M   I   S   R   T   P   E   V   T   C   V   V   V

GACGTGAGCCACGAAGACCCTGAGGTCAAGTTCAACTGGTACGTGGACGGCGTGGAGGTG
D   V   S   H   E   D   P   E   V   K   F   N   W   Y   V   D   G   V   E   V

CATAATGCCAAGACAAAGCCGCGGGAGGAGCAGTACAACAGCACGTACCGTGTGGTCAGC
H   N   A   K   T   K   P   R   E   E   Q   Y   N   S   T   Y   R   V   V   S

GTCCTCACCGTCCTGCACCAGGACTGGCTGAATGGCAAGGAGTACAAGTGCAAGGTCTCC
V   L   T   V   L   H   Q   D   W   L   N   G   K   E   Y   K   C   K   V   S

AACAAAGCCCTCCCAGCCCCCATCGAGAAAACCATCTCCAAAGCCAAAGGGCAGCCCCGA
N   K   A   L   P   A   P   I   E   K   T   I   S   K   A   K   G   Q   P   R

GAACCACAGGTGTACACCCTGCCCCCATCCCGGGATGAGCTGACCAAGAACCAGGTCAGC
E   P   Q   V   Y   T   L   P   P   S   R   D   E   L   T   K   N   Q   V   S

CTGACCTGCCTGGTCAAAGGCTTCTATCCCAGCGACATCGCCGTGGAGTGGGAGAGCAAT
L   T   C   L   V   K   G   F   Y   P   S   D   I   A   V   E   W   E   S   N

GGGCAGCCGGAGAACAACTACAAGACCACGCCTCCCGTGCTGGACTCCGACGGCTCCTTC
G   Q   P   E   N   N   Y   K   T   T   P   P   V   L   D   S   D   G   S   F

TTCCTCTACAGCAAGCTCACCGTGGACAAGAGCAGGTGGCAGCAGGGGAACGTCTTCTCA
F   L   Y   S   K   L   T   V   D   K   S   R   W   Q   Q   G   N   V   F   S

TGCTCCGTGATGCATGAGGCTCTGCACAACCACTACACGCAGAAGAGCCTCTCCCTGTCT
C   S   V   M   H   E   A   L   H   N   H   Y   T   Q   K   S   L   S   L   S

CCGGGTAAATGA
P   G   K   *
```

FIG. 20

```
ATGGGTGTACTGCTCACACAGAGGACGCTGCTCAGTCTGGTCCTTGCACTCCTGTTTCCA
 M   G   V   L   L   T   Q   R   T   L   L   S   L   V   L   A   L   L   F   P

AGCATGGCGAGCATGGCAATGCACGTGGCCCAGCCTGCTGTGGTACTGGCCAGCAGCCGA
 S   M   A   S   M   A   M   H   V   A   Q   P   A   V   V   L   A   S   S   R

GGCATCGCTAGCTTTGTGTGTGAGTATGCATCTCCAGGCAAAACTACTGAGGTCCGGGTG
 G   I   A   S   F   V   C   E   Y   A   S   P   G   K   T   T   E   V   R   V

ACAGTGCTTCGGCAGGCTGACAGCCAGGTGACTGAAGTCTGTGCGGCAACCTACATGATG
 T   V   L   R   Q   A   D   S   Q   V   T   E   V   C   A   A   T   Y   M   M

GGGAATGAGTTGACCTTCCTAGATGATTCCATCTGCACGGGCACCTCCAGTGGAAATCAA
 G   N   E   L   T   F   L   D   D   S   I   C   T   G   T   S   S   G   N   Q

GTGAACCTCACTATCCAAGGACTGAGGGCCATGGACACGGGACTCTACATCTGCAAGGTG
 V   N   L   T   I   Q   G   L   R   A   M   D   T   G   L   Y   I   C   K   V

GAGCTCATGTACCCACCGCCATACTACGAGGGCATAGGCAACGGAACCCAGATTTATGTA
 E   L   M   Y   P   P   P   Y   Y   E   G   I   G   N   G   T   Q   I   Y   V

ATTGATCCAGAACCGTGCCCAGATTCTGATCAGGAGCCCAAATCTTCTGACAAAACTCAC
 I   D   P   E   P   C   P   D   S   D   Q   E   P   K   S   S   D   K   T   H

ACATCCCCACCGTCCCCAGCACCTGAACTCCTGGGGGGATCGTCAGTCTTCCTCTTCCCC
 T   S   P   P   S   P   A   P   E   L   L   G   G   S   S   V   F   L   F   P

CCAAAACCCAAGGACACCCTCATGATCTCCCGGACCCCTGAGGTCACATGCGTGGTGGTG
 P   K   P   K   D   T   L   M   I   S   R   T   P   E   V   T   C   V   V   V

GACGTGAGCCACGAAGACCCTGAGGTCAAGTTCAACTGGTACGTGGACGGCGTGGAGGTG
 D   V   S   H   E   D   P   E   V   K   F   N   W   Y   V   D   G   V   E   V

CATAATGCCAAGACAAAGCCGCGGGAGGAGCAGTACAACAGCACGTACCGTGTGGTCAGC
 H   N   A   K   T   K   P   R   E   E   Q   Y   N   S   T   Y   R   V   V   S

GTCCTCACCGTCCTGCACCAGGACTGGCTGAATGGCAAGGAGTACAAGTGCAAGGTCTCC
 V   L   T   V   L   H   Q   D   W   L   N   G   K   E   Y   K   C   K   V   S

AACAAAGCCCTCCCAGCCCCCATCGAGAAAACCATCTCCAAAGCCAAAGGGCAGCCCCGA
 N   K   A   L   P   A   P   I   E   K   T   I   S   K   A   K   G   Q   P   R

GAACCACAGGTGTACACCCTGCCCCCATCCCGGGATGAGCTGACCAAGAACCAGGTCAGC
 E   P   Q   V   Y   T   L   P   P   S   R   D   E   L   T   K   N   Q   V   S

CTGACCTGCCTGGTCAAAGGCTTCTATCCCAGCGACATCGCCGTGGAGTGGGAGAGCAAT
 L   T   C   L   V   K   G   F   Y   P   S   D   I   A   V   E   W   E   S   N

GGGCAGCCGGAGAACAACTACAAGACCACGCCTCCCGTGCTGGACTCCGACGGCTCCTTC
 G   Q   P   E   N   N   Y   K   T   T   P   P   V   L   D   S   D   G   S   F

TTCCTCTACAGCAAGCTCACCGTGGACAAGAGCAGGTGGCAGCAGGGGAACGTCTTCTCA
 F   L   Y   S   K   L   T   V   D   K   S   R   W   Q   Q   G   N   V   F   S

TGCTCCGTGATGCATGAGGCTCTGCACAACCACTACACGCAGAAGAGCCTCTCCCTGTCT
 C   S   V   M   H   E   A   L   H   N   H   Y   T   Q   K   S   L   S   L   S

CCGGGTAAATGA
 P   G   K   *
```

FIG. 21

```
ATGGGTGTACTGCTCACACAGAGGACGCTGCTCAGTCTGGTCCTTGCACTCCTGTTTCCA
M   G   V   L   L   T   Q   R   T   L   L   S   L   V   L   A   L   L   F   P

AGCATGGCGAGCATGGCAATGCACGTGGCCCAGCCTGCTGTGGTACTGGCCAGCAGCCGA
S   M   A   S   M   A   M   H   V   A   Q   P   A   V   V   L   A   S   S   R

GGCATCGCTAGCTTTGTGTGTGAGTATGCATCTCCAGGCAAATGGACTGAGGTCCGGGTG
G   I   A   S   F   V   C   E   Y   A   S   P   G   K   W   T   E   V   R   V

ACAGTGCTTCGGCAGGCTGACAGCCAGGTGACTGAAGTCTGTGCGGCAACCTACATGATG
T   V   L   R   Q   A   D   S   Q   V   T   E   V   C   A   A   T   Y   M   M

GGGAATGAGTTGACCTTCCTAGATGATTCCATCTGCACGGGCACCTCCAGTGGAAATCAA
G   N   E   L   T   F   L   D   D   S   I   C   T   G   T   S   S   G   N   Q

GTGAACCTCACTATCCAAGGACTGAGGGCCATGGACACGGGACTCTACATCTGCAAGGTG
V   N   L   T   I   Q   G   L   R   A   M   D   T   G   L   Y   I   C   K   V

GAGCTCATGTACCCACCGCCATACTACGAGGGCATAGGCAACGGAACCCAGATTTATGTA
E   L   M   Y   P   P   P   Y   Y   E   G   I   G   N   G   T   Q   I   Y   V

ATTGATCCAGAACCGTGCCCAGATTCTGATCAGGAGCCCAAATCTTCTGACAAAACTCAC
I   D   P   E   P   C   P   D   S   D   Q   E   P   K   S   S   D   K   T   H

ACATCCCCACCGTCCCCAGCACCTGAACTCCTGGGGGGATCGTCAGTCTTCCTCTTCCCC
T   S   P   P   S   P   A   P   E   L   L   G   G   S   S   V   F   L   F   P

CCAAAACCCAAGGACACCCTCATGATCTCCCGGACCCCTGAGGTCACATGCGTGGTGGTG
P   K   P   K   D   T   L   M   I   S   R   T   P   E   V   T   C   V   V   V

GACGTGAGCCACGAAGACCCTGAGGTCAAGTTCAACTGGTACGTGGACGGCGTGGAGGTG
D   V   S   H   E   D   P   E   V   K   F   N   W   Y   V   D   G   V   E   V

CATAATGCCAAGACAAAGCCGCGGGAGGAGCAGTACAACAGCACGTACCGTGTGGTCAGC
H   N   A   K   T   K   P   R   E   E   Q   Y   N   S   T   Y   R   V   V   S

GTCCTCACCGTCCTGCACCAGGACTGGCTGAATGGCAAGGAGTACAAGTGCAAGGTCTCC
V   L   T   V   L   H   Q   D   W   L   N   G   K   E   Y   K   C   K   V   S

AACAAAGCCCTCCCAGCCCCCATCGAGAAAACCATCTCCAAAGCCAAAGGGCAGCCCCGA
N   K   A   L   P   A   P   I   E   K   T   I   S   K   A   K   G   Q   P   R

GAACCACAGGTGTACACCCTGCCCCCATCCCGGGATGAGCTGACCAAGAACCAGGTCAGC
E   P   Q   V   Y   T   L   P   P   S   R   D   E   L   T   K   N   Q   V   S

CTGACCTGCCTGGTCAAAGGCTTCTATCCCAGCGACATCGCCGTGGAGTGGGAGAGCAAT
L   T   C   L   V   K   G   F   Y   P   S   D   I   A   V   E   W   E   S   N

GGGCAGCCGGAGAACAACTACAAGACCACGCCTCCCGTGCTGGACTCCGACGGCTCCTTC
G   Q   P   E   N   N   Y   K   T   T   P   P   V   L   D   S   D   G   S   F

TTCCTCTACAGCAAGCTCACCGTGGACAAGAGCAGGTGGCAGCAGGGGAACGTCTTCTCA
F   L   Y   S   K   L   T   V   D   K   S   R   W   Q   Q   G   N   V   F   S

TGCTCCGTGATGCATGAGGCTCTGCACAACCACTACACGCAGAAGAGCCTCTCCCTGTCT
C   S   V   M   H   E   A   L   H   N   H   Y   T   Q   K   S   L   S   L   S

CCGGGTAAATGA
P   G   K   *
```

FIG. 22

ONCOSTATIN M SIGNAL PEPTIDE

```
  M   G   V   L   L   T   Q   R   T   L   L   S   L   V   L
 ATG GGT GTA CTG CTC ACA CAG AGG ACG CTG CTC AGT CTG GTC CTT    45
                                     ←―|  +1

A   L   L   F   P   S   M   A   S   M   A   M   H   V   A
 GCA CTC CTG TTT CCA AGC ATG GCG AGC ATG GCA ATG CAC GTG GCC    90

Q   P   A   V   V   L   A   S   S   R   G   I   A   S   F
 CAG CCT GCT GTG GTA CTG GCC AGC AGC CGA GGC ATC GCC AGC TTT   135

V   C   E   Y   A   S   P   G   K   A   T   E   V   R   V
 GTG TGT GAG TAT GCA TCT CCA GGC AAA GCC ACT GAG GTC CGG GTG   180

T   V   L   R   Q   A   D   S   Q   V   T   E   V   C   A
 ACA GTG CTT CGG CAG GCT GAC AGC CAG GTG ACT GAA GTC TGT GCG   225

A   T   Y   M   M   G   N   E   L   T   F   L   D   D   S
 GCA ACC TAC ATG ATG GGG AAT GAG TTG ACC TTC CTA GAT GAT TCC   270

I   C   T   G   T   S   S   G   N   Q   V   N   L   T   I
 ATC TGC ACG GGC ACC TCC AGT GGA AAT CAA GTG AAC CTC ACT ATC   315

Q   G   L   R   A   M   D   T   G   L   Y   I   C   K   V
 CAA GGA CTG AGG GCC ATG GAC ACG GGA CTC TAC ATC TGC AAG GTG   360
                                                  GLYCOSYLATION SITE

E   L   M   Y   P   P   P   Y   Y   L   G   I   G   N   G
 GAG CTC ATG TAC CCA CCG CCA TAC TAC CTG GGC ATA GGC AAC GGA   405
 ←―|
  T   Q   I   Y   V   I   D   P   E   P   C   P   D   S   D
 ACC CAG ATT TAT GTA ATT GAT CCA GAA CCG TGC CCA GAT TCT GAC   450

F   L   L   W   I   L   A   A   V   S   S   G   L   F   F
 TTC CTC CTC TGG ATC CTT GCA GCA GTT AGT TCG GGG TTG TTT TTT   495

Y   S   F   L   L   T   A   V   S   L   S   K   M   L   K
 TAT AGC TTT CTC CTC ACA GCT GTT TCT TTG AGC AAA ATG CTA AAG   540

K   R   S   P   L   T   T   G   V   Y   V   K   M   P   P
 AAA AGA AGC CCT CTT ACA ACA GGG GTC TAT GTG AAA ATG CCC CCA   585

T   E   P   E   C   E   K   Q   F   Q   P   Y   F   I   P
 ACA GAG CCA GAA TGT GAA AAG CAA TTT CAG CCT TAT TTT ATT CCC   630

I   N
 ATC AAT                                                        636
```

FIG. 23

```
ATGGGTGTACTGCTCACACAGAGGACGCTGCTCAGTCTGGTCCTTGCACTCCTGTTTCCA        -19
M~~G~~V~~L~~L~~T~~Q~~R~~T~~L~~L~~S~~L~~V~~L~~A~~L~~L~~F~~P~~         -7

AGCATGGCGAGCATGGCAATGCACGTGGCCCAGCCTGCTGTGGTACTGGCCAGCAGCCGA        +42
S~~M~~A~~S~~M~~A~~M~~H~~V~~A~~Q~~P~~A~~V~~V~~L~~A~~S~~S~~R~~        +14
             +1

GGCATCGCTAGCTTTGTGTGTGAGTATGCATCTCCAGGCAAAGCCACTGAGGTCCGGGTG       +102
G~~I~~A~~S~~F~~V~~C~~E~~Y~~A~~S~~P~~G~~K~~A~~T~~E~~V~~R~~V~~        +34

ACAGTGCTTCGGCAGGCTGACAGCCAGGTGACTGAAGTCTGTGCGGCAACCTACATGATG       +162
T~~V~~L~~R~~Q~~A~~D~~S~~Q~~V~~T~~E~~V~~C~~A~~A~~T~~Y~~M~~M~~        +54

GGGAATGAGTTGACCTTCCTAGATGATTCCATCTGCACGGGCACCTCCAGTGGAAATCAA       +222
G~~N~~E~~L~~T~~F~~L~~D~~D~~S~~I~~C~~T~~G~~T~~S~~S~~G~~N~~Q~~        +74

GTGAACCTCACTATCCAAGGACTGAGGGCCATGGACACGGGACTCTACATCTGCAAGGTG       +282
V~~N~~L~~T~~I~~Q~~G~~L~~R~~A~~M~~D~~T~~G~~L~~Y~~I~~C~~K~~V~~        +94

GAGCTCATGTACCCACCGCCATACTACCTGGGCATAGGCAACGGAACCCAGATTTATGTA       +342
E~~L~~M~~Y~~P~~P~~P~~Y~~Y~~L~~G~~I~~G~~N~~G~~T~~Q~~I~~Y~~V~~       +114

ATTGATCCAGAACCGTGCCCAGATTCTGATCAGGAGCCCAAATCTTCTGACAAAACTCAC       +402
I~~D~~P~~E~~P~~C~~P~~D~~S~~D~~Q~~E~~P~~K~~S~~S~~D~~K~~T~~H~~       +134

ACATCCCCACCGTCCCCAGCACCTGAACTCCTGGGTGGATCGTCAGTCTTCCTCTTCCCC       +462
T~~S~~P~~P~~S~~P~~A~~P~~E~~L~~L~~G~~G~~S~~S~~V~~F~~L~~F~~P~~       +154

CCAAAACCCAAGGACACCCTCATGATCTCCCGGACCCCTGAGGTCACATGCGTGGTGGTG       +522
P~~K~~P~~K~~D~~T~~L~~M~~I~~S~~R~~T~~P~~E~~V~~T~~C~~V~~V~~V~~       +174

GACGTGAGCCACGAAGACCCTGAGGTCAAGTTCAACTGGTACGTGGACGGCGTGGAGGTG       +582
D~~V~~S~~H~~E~~D~~P~~E~~V~~K~~F~~N~~W~~Y~~V~~D~~G~~V~~E~~V~~       +194

CATAATGCCAAGACAAAGCCGCGGGAGGAGCAGTACAACAGCACGTACCGGGTGGTCAGC       +642
H~~N~~A~~K~~T~~K~~P~~R~~E~~E~~Q~~Y~~N~~S~~T~~Y~~R~~V~~V~~S~~       +214

GTCCTCACCGTCCTGCACCAGGACTGGCTGAATGGCAAGGAGTACAAGTGCAAGGTCTCC       +702
V~~L~~T~~V~~L~~H~~Q~~D~~W~~L~~N~~G~~K~~E~~Y~~K~~C~~K~~V~~S~~       +234

AACAAAGCCCTCCCAGCCCCCATCGAGAAAACCATCTCCAAAGCCAAAGGGCAGCCCCGA       +762
N~~K~~A~~L~~P~~A~~P~~I~~E~~K~~T~~I~~S~~K~~A~~K~~G~~Q~~P~~R~~       +254

GAACCACAGGTGTACACCCTGCCCCCATCCCGGGATGAGCTGACCAAGAACCAGGTCAGC       +822
E~~P~~Q~~V~~Y~~T~~L~~P~~P~~S~~R~~D~~E~~L~~T~~K~~N~~Q~~V~~S~~       +274

CTGACCTGCCTGGTCAAAGGCTTCTATCCCAGCGACATCGCCGTGGAGTGGGAGAGCAAT       +882
L~~T~~C~~L~~V~~K~~G~~F~~Y~~P~~S~~D~~I~~A~~V~~E~~W~~E~~S~~N~~       +294

GGGCAGCCGGAGAACAACTACAAGACCACGCCTCCCGTGCTGGACTCCGACGGCTCCTTC       +942
G~~Q~~P~~E~~N~~N~~Y~~K~~T~~T~~P~~P~~V~~L~~D~~S~~D~~G~~S~~F~~       +314

TTCCTCTACAGCAAGCTCACCGTGGACAAGAGCAGGTGGCAGCAGGGGAACGTCTTCTCA      +1002
F~~L~~Y~~S~~K~~L~~T~~V~~D~~K~~S~~R~~W~~Q~~Q~~G~~N~~V~~F~~S~~       +334

TGCTCCGTGATGCATGAGGCTCTGCACAACCACTACACGCAGAAGAGCCTCTCCCTGTCT      +1062
C~~S~~V~~M~~H~~E~~A~~L~~H~~N~~H~~Y~~T~~Q~~K~~S~~L~~S~~L~~S~~       +354

CCGGGTAAATGA
P~~G~~K~~*
```

FIG. 24

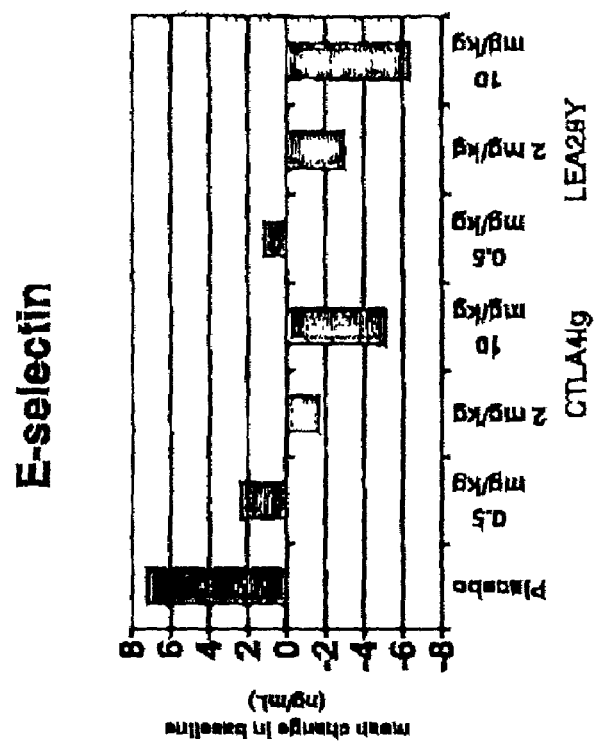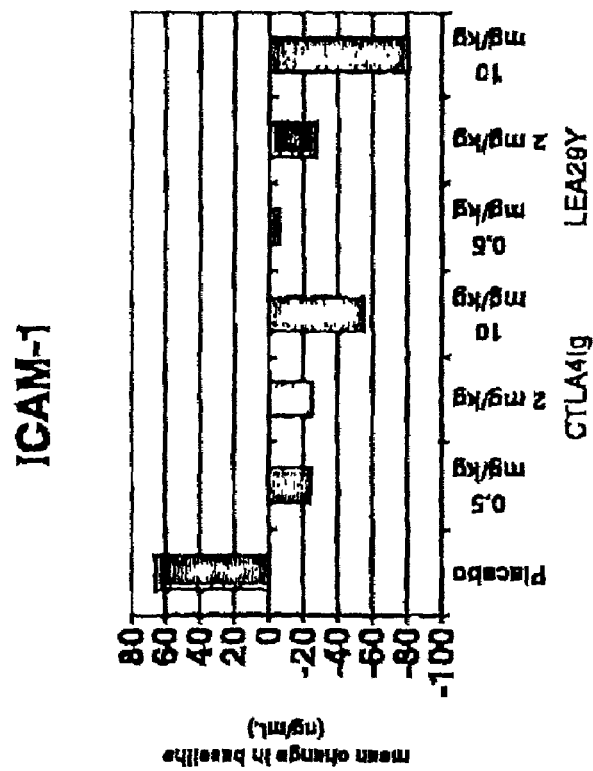
Figure 33

SEQUENCE LISTING

```
<160> NUMBER OF SEQ ID NOS: 20

<210> SEQ ID NO 1
<211> LENGTH: 65
<212> TYPE: DNA
<213> ORGANISM: Homo sapiens

<400> SEQUENCE: 1
ctcagtctgg tccttgcact cctgtttcca agcatggcga gcatggcaat gcacgtggcc      60
cagcc                                                                  65

<210> SEQ ID NO 2
<211> LENGTH: 33
<212> TYPE: DNA
<213> ORGANISM: Homo sapiens

<400> SEQUENCE: 2
tttgggctcc tgatcagaat ctgggcacgg ttg                                    33

<210> SEQ ID NO 3
<211> LENGTH: 72
<212> TYPE: DNA
<213> ORGANISM: Homo sapiens

<400> SEQUENCE: 3
ctagccactg aagcttcacc aatgggtgta ctgctcacac agaggacgct gctcagtctg      60
gtccttgcac tc                                                          72

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Oncostatin
      M CTLA4 (OMCTLA4) Forward Primer

<400> SEQUENCE: 4
```
gaggtgataa agcttcacca atgggtgtac tgctcacaca g        41

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Oncostatin
      M CTLA4 (OMCTLA4) Reverse Primer

<400> SEQUENCE: 5
gtggtgtatt ggtctagatc aatcagaatc tgggcacggt tc        42

<210> SEQ ID NO 6
<211> LENGTH: 1152
<212> TYPE: DNA
<213> ORGANISM: L104EIg

<400> SEQUENCE: 6
atgggtgtac tgctcacaca gaggacgctg ctcagtctgg tccttgcact cctgtttcca        60
agcatggcga gcatggcaat gcacgtggcc cagcctgctg tggtactggc cagcagccga       120
ggcatcgcta gctttgtgtg tgagtatgca tctccaggca aagccactga ggtccgggtg       180
acagtgcttc ggcaggctga cagccaggtg actgaagtct gtgcggcaac ctacatgatg       240
gggaatgagt tgaccttcct agatgattcc atctgcacgg gcacctccag tggaaatcaa       300
gtgaacctca ctatccaagg actgagggcc atggacacgg gactctacat ctgcaaggtg       360
gagctcatgt acccaccgcc atactacgag ggcataggca acggaaccca gatttatgta       420
attgatccag aaccgtgccc agattctgat caggagccca atcttctga caaaactcac        480
acatccccac cgtccccagc acctgaactc ctggggggat cgtcagtctt cctcttcccc       540
ccaaaaccca aggacaccct catgatctcc cggacccctg aggtcacatg cgtggtggtg       600
gacgtgagcc acgaagaccc tgaggtcaag ttcaactggt acgtggacgg cgtggaggtg       660
cataatgcca agacaaagcc gcgggaggag cagtacaaca gcacgtaccg tgtggtcagc       720
gtcctcaccg tcctgcacca ggactggctg aatggcaagg agtacaagtg caaggtctcc       780
aacaaagccc tcccagcccc catcgagaaa accatctcca aagccaaagg cagccccga       840
gaaccacagg tgtacaccct gcccccatcc cgggatgagc tgaccaagaa ccaggtcagc       900
ctgacctgcc tggtcaaagg cttctatccc agcgacatcg ccgtggagtg ggagagcaat       960
gggcagccgg agaacaacta caagaccacg cctcccgtgc tggactccga cggctccttc      1020
ttcctctaca gcaagctcac cgtggacaag agcaggtggc agcagggga acgtcttctca      1080
tgctccgtga tgcatgaggc tctgcacaac cactacacgc agaagagcct ctccctgtct      1140
ccgggtaaat ga                                                          1152

<210> SEQ ID NO 7
<211> LENGTH: 383
<212> TYPE: PRT
<213> ORGANISM: L104EIg

<400> SEQUENCE: 7

Met Gly Val Leu Leu Thr Gln Arg Thr Leu Leu Ser Leu Val Leu Ala
  1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu 35                  40                  45
Tyr Ala Ser Pro Gly Lys Ala Thr Glu Val Arg Val Thr Val Leu Arg
 50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 8
<211> LENGTH: 1152
<212> TYPE: DNA
<213> ORGANISM: L104EA29YIg

<400> SEQUENCE: 8
atgggtgtac tgctcacaca gaggacgctg ctcagtctgg tccttgcact cctgtttcca     60
agcatggcga gcatggcaat gcacgtggcc cagcctgctg tggtactggc cagcagccga    120
ggcatcgcta gctttgtgtg tgagtatgca tctccaggca aatatactga ggtccgggtg    180

```
acagtgcttc ggcaggctga cagccaggtg actgaagtct gtgcggcaac ctacatgatg    240
gggaatgagt tgaccttcct agatgattcc atctgcacgg gcacctccag tggaaatcaa    300
gtgaacctca ctatccaagg actgagggcc atggacacgg gactctacat ctgcaaggtg    360
gagctcatgt acccaccgcc atactacgag ggcataggca acggaaccca gatttatgta    420
attgatccag aaccgtgccc agattctgat caggagccca atcttctga caaaactcac     480 acatcccac cgtccccagc acctgaactc ctgggggat cgtcagtctt cctcttcccc       540
ccaaaaccca aggacaccct catgatctcc cggacccctg aggtcacatg cgtggtggtg    600
gacgtgagcc acgaagaccc tgaggtcaag ttcaactggt acgtggacgg cgtggaggtg    660
cataatgcca agacaaagcc gcgggaggag cagtacaaca gcacgtaccg tgtggtcagc    720
gtcctcaccg tcctgcacca ggactggctg aatggcaagg agtacaagtg caaggtctcc    780
aacaaagccc tcccagcccc catcgagaaa accatctcca aagccaaagg cagccccga    840 gaaccacagg tgtacaccct gcccccatcc cgggatgagc tgaccaagaa ccaggtcagc    900
ctgacctgcc tggtcaaagg cttctatccc agcgacatcg ccgtggagtg ggagagcaat    960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

<210> SEQ ID NO 9
<211> LENGTH: 383
<212> TYPE: PRT
<213> ORGANISM: L104EA29YIg

<400> SEQUENCE: 9

```
Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Tyr Thr Glu Val Arg Val Thr Val Leu Arg
     50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
```

```
                 195                 200                 205
Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 10
<211> LENGTH: 1152
<212> TYPE: DNA
<213> ORGANISM: Artificial Sequence
<220> FEATURE:
<223> OTHER INFORMATION: Description of Artificial Sequence: L104EA29LIg

<400> SEQUENCE: 10
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aattgactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggca atggacacgg gactctacat ctgcaaggtg     360
gagctcatgt acccaccgcc atactacgag ggcataggca cggaaccca gatttatgta     420 attgatccag aaccgtgccc agattctgat caggagccca atcttctga caaaactcac     480 acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca aagccaaagg cagccccga      840 gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
```

```
ttcctctaca gcaagctcac cgtggacaag agcaggtggc agcagggaa cgtcttctca    1080 tgctccgtga tgcatgaggc tctgcacaac cactacacgc agaagagcct ctccctgtct    1140
ccgggtaaat ga                                                        1152
```

<210> SEQ ID NO 11
<211> LENGTH: 383
<212> TYPE: PRT
<213> ORGANISM: Artificial Sequence
<220> FEATURE:
<223> OTHER INFORMATION: Description of Artificial Sequence: L104EA29LIg

<400> SEQUENCE: 11

```
Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Leu Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
           100                 105                 110

Thr Gly Leu Tyr Ile Cys Lys Val Glu Leu Met Tyr Pro Pro Pro Tyr
       115                 120                 125

Tyr Glu Gly Ile Gly Asn Gly Thr Gln Ile Tyr Val Ile Asp Pro Glu
   130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335
```

```
Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
        370                 375                 380

<210> SEQ ID NO 12
<211> LENGTH: 1152
<212> TYPE: DNA
<213> ORGANISM: Artificial Sequence
<220> FEATURE:
<223> OTHER INFORMATION: Description of Artificial Sequence: L104EA29TIg

<400> SEQUENCE: 12
atgggtgtac tgctcacaca gaggacgctg ctcagtctgg tccttgcact cctgtttcca      60
agcatggcga gcatggcaat gcacgtggcc cagcctgctg tggtactggc agcagccga     120
ggcatcgcta gctttgtgtg tgagtatgca tctccaggca aaactactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca cggaaccca gatttatgta     420
attgatccag aaccgtgccc agattctgat caggagccca atcttctga caaaactcac     480
acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca aagccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152

<210> SEQ ID NO 13
<211> LENGTH: 383
<212> TYPE: PRT
<213> ORGANISM: Artificial Sequence
<220> FEATURE:
<223> OTHER INFORMATION: Description of Artificial Sequence: L104EA29TIg

<400> SEQUENCE: 13

Met Gly Val Leu Leu Thr Gln Arg Thr Leu Leu Ser Leu Val Leu Ala
  1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Thr Thr Glu Val Arg Val Thr Val Leu Arg
```

|   |   |   |   |   |   |   |   |   |   |   |   |
|---|---|---|---|---|---|---|---|---|---|---|---|
|   |   |   | 50 |   |   | 55 |   |   | 60 |   |   |
| Gln | Ala | Asp | Ser | Gln | Val | Thr | Glu | Val | Cys | Ala | Ala | Thr | Tyr | Met | Met |
| 65 |   |   |   | 70 |   |   |   | 75 |   |   |   | 80 |

Gly Asn Glu Leu Thr Phe Leu Asp Asp Ser Ile Cys Thr Gly Thr Ser
                  85                    90                    95

Ser Gly Asn Gln Val Asn Leu Thr Ile Gln Gly Leu Arg Ala Met Asp
            100                  105                  110

Thr Gly Leu Tyr Ile Cys Lys Val Glu Leu Met Tyr Pro Pro Pro Tyr
        115                  120                  125

Tyr Glu Gly Ile Gly Asn Gly Thr Gln Ile Tyr Val Ile Asp Pro Glu
130                  135                  140

Pro Cys Pro Asp Ser Asp Gln Glu Pro Lys Ser Ser Asp Lys Thr His
145                  150                  155                  160

Thr Ser Pro Pro Ser Pro Ala Pro Glu Leu Leu Gly Gly Ser Ser Val
        165                  170                  175

Phe Leu Phe Pro Pro Lys Pro Lys Asp Thr Leu Met Ile Ser Arg Thr
          180                  185                  190

Pro Glu Val Thr Cys Val Val Val Asp Val Ser His Glu Asp Pro Glu
        195                  200                  205

Val Lys Phe Asn Trp Tyr Val Asp Gly Val Glu Val His Asn Ala Lys
      210                  215                  220

Thr Lys Pro Arg Glu Glu Gln Tyr Asn Ser Thr Tyr Arg Val Val Ser
225                  230                  235                  240

Val Leu Thr Val Leu His Gln Asp Trp Leu Asn Gly Lys Glu Tyr Lys
          245                  250                  255

Cys Lys Val Ser Asn Lys Ala Leu Pro Ala Pro Ile Glu Lys Thr Ile
            260                  265                  270

Ser Lys Ala Lys Gly Gln Pro Arg Glu Pro Gln Val Tyr Thr Leu Pro
        275                  280                  285

Pro Ser Arg Asp Glu Leu Thr Lys Asn Gln Val Ser Leu Thr Cys Leu
          290                  295                  300

Val Lys Gly Phe Tyr Pro Ser Asp Ile Ala Val Glu Trp Glu Ser Asn
305                  310                  315                  320

Gly Gln Pro Glu Asn Asn Tyr Lys Thr Thr Pro Pro Val Leu Asp Ser
                325                  330                  335

Asp Gly Ser Phe Phe Leu Tyr Ser Lys Leu Thr Val Asp Lys Ser Arg
              340                  345                  350

Trp Gln Gln Gly Asn Val Phe Ser Cys Ser Val Met His Glu Ala Leu
            355                  360                  365

His Asn His Tyr Thr Gln Lys Ser Leu Ser Leu Ser Pro Gly Lys
370                  375                  380

<210> SEQ ID NO 14
<211> LENGTH: 1152
<212> TYPE: DNA
<213> ORGANISM: Artificial Sequence
<220> FEATURE:
<223> OTHER INFORMATION: Description of Artificial Sequence: L104EA29WIg

<400> SEQUENCE: 14

| | | |
|---|---|---|
| atgggtgtac tgctcacaca gaggacgctg ctcagtctgg tccttgcact cctgtttcca | 60 |
| agcatggcga gcatggcaat gcacgtggcc cagcctgctg tggtactggc cagcagccga | 120 |
| ggcatcgcta gctttgtgtg tgagtatgca tctccaggca aatggactga ggtccgggtg | 180 |
| acagtgcttc ggcaggctga cagccaggtg actgaagtct gtgcggcaac ctacatgatg | 240 |

```
gggaatgagt tgaccttcct agatgattcc atctgcacgg gcacctccag tggaaatcaa        300
gtgaacctca ctatccaagg actgagggcc atggacacgg actctacat ctgcaaggtg         360 gagctcatgt acccaccgcc atactacgag ggcataggca acggaaccca gatttatgta         420
attgatccag aaccgtgccc agattctgat caggagccca atcttctga caaaactcac         480 acatccccac cgtccccagc acctgaactc ctggggggat cgtcagtctt cctcttcccc         540
ccaaaaccca aggacaccct catgatctcc cggacccctg aggtcacatg cgtggtggtg         600
gacgtgagcc acgaagaccc tgaggtcaag ttcaactggt acgtggacgg cgtggaggtg         660
cataatgcca agacaaagcc gcgggaggag cagtacaaca gcacgtaccg tgtggtcagc         720
gtcctcaccg tcctgcacca ggactggctg aatggcaagg agtacaagtg caaggtctcc         780
aacaaagccc tcccagcccc catcgagaaa accatctcca aagccaaagg cagccccga          840 gaaccacagg tgtacaccct gcccccatcc cgggatgagc tgaccaagaa ccaggtcagc         900
ctgacctgcc tggtcaaagg cttctatccc agcgacatcg ccgtggagtg ggagagcaat        960
gggcagccgg agaacaacta caagaccacg cctcccgtgc tggactccga cggctccttc       1020
ttcctctaca gcaagctcac cgtggacaag agcaggtggc agcaggggaa cgtcttctca       1080
tgctccgtga tgcatgaggc tctgcacaac cactacacgc agaagagcct ctccctgtct       1140
ccgggtaaat ga                                                           1152
```

<210> SEQ ID NO 15
<211> LENGTH: 383
<212> TYPE: PRT
<213> ORGANISM: Artificial Sequence
<220> FEATURE:
<223> OTHER INFORMATION: Description of Artificial Sequence: L104EA29WIg

<400> SEQUENCE: 15

```
Met Gly Val Leu Leu Thr Gln Arg Thr Leu Leu Ser Leu Val Leu Ala
  1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Trp Thr Glu Val Arg Val Thr Val Leu Arg
     50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190
```

```
Pro Glu Val Thr Cys Val Val Asp Val Ser His Glu Asp Pro Glu
        195                 200                 205

Val Lys Phe Asn Trp Tyr Val Asp Gly Val Glu Val His Asn Ala Lys
        210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
        290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
        370                 375                 380

<210> SEQ ID NO 16
<211> LENGTH: 636
<212> TYPE: DNA
<213> ORGANISM: Homo sapiens

<400> SEQUENCE: 16
atgggtgtac tgctcacaca gaggacgctg ctcagtctgg tccttgcact cctgtttcca    60
agcatggcga gcatggcaat gcacgtggcc cagcctgctg tggtactggc agcagccga   120 ggcatcgcca gctttgtgtg tgagtatgca tctccaggca aagccactga ggtccgggtg   180
acagtgcttc ggcaggctga cagccaggtg actgaagtct gtgcggcaac ctacatgatg   240
gggaatgagt tgaccttcct agatgattcc atctgcacgg gcacctccag tggaaatcaa   300
gtgaacctca ctatccaagg actgagggcc atggacacgg actctacat ctgcaaggtg   360 gagctcatgt acccaccgcc atactacctg ggcataggca cggaaccca gatttatgta   420 attgatccag aaccgtgccc agattctgac ttcctcctct ggatccttgc agcagttagt   480
tcggggttgt ttttttatag ctttctcctc acagctgttt ctttgagcaa aatgctaaag   540
aaaagaagcc ctcttacaac aggggtctat gtgaaaatgc ccccaacaga gccagaatgt   600
gaaaagcaat tcagccctta ttttattccc atcaat                             636

<210> SEQ ID NO 17
<211> LENGTH: 212
<212> TYPE: PRT
<213> ORGANISM: Homo sapiens

<400> SEQUENCE: 17

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30
```

```
Ala Val Val Leu Ala Ser Ser Arg Gly Ile Ala Ser Phe Val Cys Glu
             35                  40                  45

Tyr Ala Ser Pro Gly Lys Ala Thr Glu Val Arg Val Thr Val Leu Arg
 50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
            130                 135                 140

Pro Cys Pro Asp Ser Asp Phe Leu Leu Trp Ile Leu Ala Ala Val Ser
145                 150                 155                 160

Ser Gly Leu Phe Phe Tyr Ser Phe Leu Leu Thr Ala Val Ser Leu Ser
                165                 170                 175

Lys Met Leu Lys Lys Arg Ser Pro Leu Thr Thr Gly Val Tyr Val Lys
            180                 185                 190

Met Pro Pro Thr Glu Pro Glu Cys Glu Lys Gln Phe Gln Pro Tyr Phe
            195                 200                 205

Ile Pro Ile Asn
    210

<210> SEQ ID NO 18
<211> LENGTH: 1152
<212> TYPE: DNA
<213> ORGANISM: CTLA4Ig

<400> SEQUENCE: 18
atgggtgtac tgctcacaca gaggacgctg ctcagtctgg tccttgcact cctgtttcca      60
agcatggcga gcatggcaat gcacgtggcc cagcctgctg tggtactggc agcagccga     120
ggcatcgcta gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggca atggacacgg gactctacat ctgcaaggtg     360
gagctcatgt acccaccgcc atactacctg ggcataggca acggaaccca gatttatgta     420
attgatccag aaccgtgccc agattctgat caggagccca atcttctga caaaactcac     480
acatccccac cgtccccagc acctgaactc ctgggtggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg ggtggtcagc     720
gtcctcaccg tcctgcacca ggactggctg aatggcaagg agtacaagtg caaggtctcc     780
aacaaagccc tcccagcccc catcgagaaa accatctcca agccaaagg cagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
```

```
ttcctctaca gcaagctcac cgtggacaag agcaggtggc agcagggaa cgtcttctca   1080 tgctccgtga tgcatgaggc tctgcacaac cactacacgc agaagagcct ctccctgtct   1140
ccgggtaaat ga                                                       1152
```

<210> SEQ ID NO 19
<211> LENGTH: 383
<212> TYPE: PRT
<213> ORGANISM: CTLA4Ig

<400> SEQUENCE: 19

```
Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Ala Thr Glu Val Arg Val Thr Val Leu Arg
     50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350
```

```
Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:MYPPPY amino
      acid sequence

<400> SEQUENCE: 20

Met Tyr Pro Pro Pro Tyr
 1               5
```

METHODS FOR TREATING IMMUNE SYSTEM DISEASES USING A SOLUBLE CTLA4 MOLECULE

This application claims the priority of U.S. Provisional Patent Application Ser. No. 60/215,913, filed Jul. 3, 2000, the contents of which are hereby incorporated by reference in their entirety.

Throughout this application various publications are referenced. The disclosures of these publications in their entireties are hereby incorporated by reference into this application in order to more fully describe the state of the art to which this invention pertains.

FIELD OF THE INVENTION

The present invention relates generally to the field of rheumatic diseases. In particular, the invention relates to methods and compositions for treating rheumatic diseases, such as rheumatoid arthritis, by administering to a subject an effective amount of soluble CTLA4 mutant molecules.

BACKGROUND OF THE INVENTION

No cure currently exists for rheumatic diseases. Rather, therapeutic agents are used to treat the symptoms. Typically, the therapeutic agents are administered over long periods of time and the therapeutic value is often diminished by adverse side effects.

Rheumatic diseases encompass a group of diseases that affect the musculo-skeletal and connective tissues of the body. These diseases are characterized by chronic inflammation that often leads to permanent tissue damage, deformity, atrophy and disability. Rheumatic diseases affect the joints, bone, soft tissue, or spinal cord (Mathies, H. 1983 *Rheuma*) and are classified as inflammatory rheumatism, degenerative rheumatism, extra-articular rheumatism, or collagen diseases. Some rheumatic diseases are known to be autoimmune diseases caused by a subject's altered immune response.

Rheumatoid arthritis is a progressive rheumatic disease, affecting approximately 2% of the adult population of developed countries (Utsinger, P. D., et al., 1985 *Rheumatoid Arthritis*, p. 140). This disease is characterized by persistent inflammatory synovitis that causes destruction of cartilage and bone erosion, leading to structural deformities in the peripheral joints. The symptoms associated with rheumatoid arthritis include joint swelling, joint tenderness, inflammation, morning stiffness, and pain, especially upon flexing. Subjects having advanced stages of arthritis suffer from structural damage, including joint destruction with bone erosion (in: "Principals of Internal Medicine, Harrison, 13th edition, pages 1648-1655). In addition, patients can present other clinical symptoms of various organic lesions, including lesions of the skin, kidney, heart, lung, central nervous system, and eyes due to vasculitis related to the autoimmune process.

Other symptoms that correlate with rheumatoid arthritis include elevated erythrocyte sedimentation rates, and elevated levels of serum C-reactive protein (CRP) and/or soluble IL-2 receptor (IL-2r). The erythrocyte sedimentation rate is increased in nearly all patients with active rheumatoid arthritis. The level of serum C-reactive protein is also elevated and correlates with disease activity and the likelihood of progressive joint damage. Additionally, the level of soluble IL-2r, a product of activated T-cells, is elevated in blood serum and synovial fluid of patients with active rheumatoid arthritis (see: "Principals of Internal Medicine, Harrison, 13th edition, page 1650).

Rheumatoid arthritis is believed to be a T-cell-mediated autoimmune disease, involving antigen-nonspecific intercellular interactions between T-lymphocytes and antigen-presenting cells. In general, the magnitude of the T-cell response is determined by the co-stimulatory response elicited by the interaction between T-cell surface molecules and their ligands (Mueller, et al., 1989 *Ann. Rev. Immunol.* 7:445-480). Key co-stimulatory signals are provided by the interaction between T-cell surface receptors, CD28 and CTLA4, and their ligands, such as B7-related molecules CD80 (i.e., B7-1) and CD86 (i.e., B7-2), on antigen presenting cells (Linsley, P. and Ledbetter, J. 1993 *Ann. Rev. Immunol.* 11:191-212).

T-cell activation in the absence of co-stimulation results in anergic T-cell response (Schwartz, R. H., 1992 *Cell* 71:1065-1068) wherein the immune system becomes nonresponsive to stimulation.

Since rheumatoid arthritis is thought to be a T-cell-mediated immune system disease, one strategy to develop new agents to treat rheumatoid arthritis is to identify molecules that block co-stimulatory signals between T-lymphocytes and antigen presenting cells, by blocking the interaction between endogenous CD28 or CTLA4 and B7. Potential molecules include soluble CTLA4 molecules that are modified to bind to B7 with higher avidity than wildtype CTLA4 (the sequence of which is shown in FIG. 23) or CD28, thereby blocking the co-stimulatory signals.

Soluble forms of CD28 and CTLA4 have been constructed by fusing variable (V)-like extracellular domains of CD28 and CTLA4 to immunoglobulin (Ig) constant domains resulting in CD28Ig and CTLA4Ig. A nucleotide and amino acid sequence of CTLA4Ig is shown in FIG. 24 with the protein beginning with methionine at position +1 or alanine at position −1 and ending with lysine at position +357. CTLA4Ig binds both CD80-positive and CD86-postive cells more strongly than CD28Ig (Linsley, P., et al., 1994 *Immunity* 1:793-80). Many T-cell-dependent immune responses have been found to be blocked by CTLA4Ig both in vitro and in vivo. (Linsley, P., et al., 1991b, supra; Linsley, P., et al., 1992a *Science* 257:792-795; Linsley, P., et al., 1992b *J. Exp. Med.* 176:1595-1604; Lenschow, D. J., et al. 1992 *Science* 257:789-792; Tan, P., et al., 1992 *J. Exp. Med.* 177:165-173; Turka, L. A., 1992 *Proc. Natl. Acad. Sci. USA* 89:11102-11105).

To alter binding affinity to natural ligands, such as B7, soluble CTLA4Ig fusion molecules were modified by mutation of amino acids in the CTLA4 portion of the molecules. Regions of CTLA4 that, when mutated, alter the binding affinity or avidity for B7 ligands include the complementarity determining region 1 (CDR-1 as described in U.S. Pat. Nos. 6,090,914, 5,773,253, 5,844,095; in copending U.S. patent application Ser. No. 60/214,065; and by Peach et ,1, 1994. J. Exp. Med., 180:2049-2058) and complementarity determining region 3 (CDR-3)-like regions (CDR-3 is the conserved region of the CTLA4 extracellular domain as described in U.S. Pat. Nos. 6,090,914, 5,773,253 and 5,844,095; in copending U.S. patent application Ser. No. 60/214,065; and by Peach, R. J., et al *J Exp Med* 1994 180:2049-2058. The CDR-3-like region encompasses the CDR-3 region and extends, by several amino acids, upstream and/or downstream of the CDR-3 motif). The CDR-3-like region includes a hexapeptide motif MYPPPY (SEQ ID NO:20) that is highly conserved in all CD28 and CTLA4 family members. Alanine scanning mutagenesis through the hexapeptide motif in CTLA4, and at selected residues in CD28Ig, reduced or abolished binding to CD80 (Peach, R. J., et al *J Exp Med* 1994 180:2049-2058).

Further modifications were made to soluble CTLA4Ig molecule. by interchanging homologous regions of CTLA4 and CD2B. These chimeric CTLA4/CD28homologue mutant molecules identified the MYPPPY hexapeptide motif (SEQ ID NO:20) common to CTLA4 and CD28, as well as certain non-conserved amino acid residues in the CDR-1- and CDR-3-like regions of CTLA4, as regions responsible for increasing the binding avidity of CTLA4 with CD80 (Peach, R. J., et al., 1994 J Exp Med 180:2049-2058).

Soluble CTLA4 molecules, such as CTLA4Ig, CTLA4 mutant molecules or chimeric CTLA4/CD28 homologue mutants as described supra, introduce a new group of therapeutic drugs to treat rheumatic diseases.

Present treatments for rheumatic diseases, such as rheumatoid arthritis, include administering nonspecific cytotoxic immunosuppressive drugs, such as methotrexate, cyclophosphamide, azathioprine, cyclosporin A, and tumor necrosis factor-alpha (TNFα) blockers or antagonists. These immunosuppressive drugs suppress the entire immune system of the subject, and long-term use increases the risk of infection. Moreover, these drugs merely slow down the progress of the rheumatoid arthritis, which resumes at an accelerated pace after the therapy is discontinued. Additionally, prolonged therapy with these nonspecific drugs produces toxic side effects, including a tendency towards development of certain malignancies, kidney failure, bone marrow suppression, pulmonary fibrosis, malignancy, diabetes, and liver function disorders. These drugs also gradually cease being effective after about 2-5 years (Kelley's Textbook of Rheumatology, $6^{th}$ Edition, pages 1001-1022).

Alternatively, therapeutic agents that are non-specific immunosuppressive and anti-inflammatory drugs have been used to obtain symptomatic relief. These drugs are dose-dependent and do not protect from disease progression. These drugs include steroid compounds, such as prednisone and methylprednisolone. Steroids also have significant toxic side effects associated with their long-term use. (Kelley's Textbook of Rheumatology, $6^{th}$ Edition, pages 829-833).

Thus, current treatments for rheumatoid arthritis are of limited efficacy, involve significant toxic side effects, and cannot be used continuously for prolonged periods of time.

Accordingly, there exists a need for treatments that are effective and more potent for treating rheumatic diseases, such as rheumatoid arthritis, and avoids the disadvantages of conventional methods and agents, by targeting a pathophysiological mechanism of auto-immunity.

SUMMARY OF THE INVENTION

The present invention provides compositions and methods for treating immune system diseases, by administering to a subject soluble CTLA4 molecules, which bind to B7 molecules on B7-positive cells, thereby inhibiting endogenous B7 molecules from binding CTLA4 and/or CD28 on T-cells. Soluble CTLA4 molecules used in the methods of the invention include CTLA4Ig and soluble CTLA4 mutant molecule L104EA29YIg.

The present invention also provides methods for inhibiting T-cell function but not T-cell depletion in a human by contacting B7-positive cells in the human with a soluble CTLA4. Examples of soluble CTLA4 include CTLA4Ig and soluble CTLA4 mutant molecule such as L104EA29YIg.

The present invention also provides methods for treating (e.g. reducing symptoms) rheumatic diseases, such as rheumatoid arthritis, by administering to a subject diagnosed with rheumatoid arthritis, soluble CTLA4 molecules such as CTLA4Ig and/or soluble CTLA4 mutant molecule L104EA29YIg. The CTLA4 mutant molecule L104EA29YIg e.g. beginning with methionine at position +1 or alanine at position −1 and ending with lysine at position +357 as shown in FIG. 19 is preferred for use in the methods of the invention.

The present invention also provides methods for reducing pathophysiological changes associated with rheumatic disease, such as structural damage, by administering to a subject diagnosed with rheumatoid arthritis, soluble CTLA4 molecules.

The present invention also provides a pharmaceutical composition for treating immune system diseases, such as rheumatic diseases, comprising a pharmaceutically acceptable carrier and a biologically effective agent such as soluble CTLA4 molecules.

Kits comprising pharmaceutical compositions therapeutic for immune system disease are also encompassed by the invention. In one embodiment, a kit comprising one or more of the pharmaceutical compositions of the invention is used to treat an immune system disease e.g. rheumatoid arthritis. For example, the pharmaceutical composition comprises an effective amount of soluble CTLA4 mutant molecules that bind to B7 molecules on B7-positive cells, thereby blocking the B7 molecules from binding CTLA4 and/or CD28 on T-cells. Further, the kit may contain one or more immunosuppressive agents used in conjunction with the pharmaceutical compositions of the invention. Potential immunosuppressive agents include, but are not limited to, corticosteroids, nonsteroidal antiinflammatory drugs (e.g. Cox-2 inhibitors), cyclosporin prednisone, azathioprine, methotrexate, TNFα blockers or antagonists, infliximab, any biological agent targeting an inflammatory cytokine, hydroxychloroquine, sulphasalazopryine, gold salts, etanercept, and anakinra.

The present invention also provides methods for reducing the erythrocyte sedimentation rate that is associated with rheumatoid arthritis.

Additionally, the present invention provides methods for reducing the levels of certain components of blood serum which are associated with rheumatoid arthritis, including C-reactive protein, soluble ICAM-1, soluble E-selectin and/or soluble IL-2r.

BRIEF DESCRIPTION OF THE FIGURES

FIG. 1A: Demographic data of patient cohorts. Demographic data including gender, race, and disease duration as described in Example 3, infra.

FIG. 1B: Demographic data of patient cohorts. Demographic data including gender, age, weight, and disease activity evaluated by the patient and by the physician as described in Example 3, infra.

FIG. 1C: Demographic data of patient cohorts as described in Example 3, infra. Demographic data including disease activity, erythrocyte sedimentation rate (ESR), physical function (disability evaluated by health questionnaire), and C-reactive protein (CRP).

FIG. 1D: Demographic data of patient cohorts as described in Example 3, infra. Demographic data including joint swelling, joint tenderness, morning stiffness, and pain.

FIG. 1E: Demographic data of patient cohorts as described in Example 3, infra. Demographic data including prior treatments.

FIG. 3B: ACR-20 responses at Day 85, including placebo response, as described in Example 3, infra: ACR-20 response with 95% confidence limits.

FIG. 4B: Clinical responses (in percentage improvement) in swollen and tender joint count in percentage of patients at Day 85 as described in Example 3, infra: change in clinical response in percentage improvement.

FIG. 7C: Mean reduction in C-reactive protein (CRP) levels at Day 85 as described in Example 3, infra: mean change from baseline.

FIG. 18: Nucleotide and amino acid sequence of L104EIg (SEQ ID NOs: 6-7) as described in Example 1, infra.

FIG. 19: Nucleotide and amino acid sequence of L104EA29YIg (SEQ ID NOs: 8-9) as described in Example 1, infra.

FIG. 20: Nucleotide and amino acid sequence of L104EA29LIg (SEQ ID NOs: 10-11) as described in Example 1, infra.

FIG. 21: Nucleotide and amino acid sequence of L104EA29TIg (SEQ ID NOs: 12-13) as described in Example 1, infra.

FIG. 22: Nucleotide and amino acid sequence of L104EA29WIg (SEQ ID NOs: 14-15) as described in Example 1, infra.

FIG. 23: Nucleotide and amino acid sequence of CTLA4 receptor (SEQ ID NOs: 16-17).

FIG. 24: Nucleotide and amino acid sequence of CTLA4Ig (SEQ ID NOs: 18-19).

FIG. 26 (right depiction) shows an expanded view of the CDR-1 (S25-R33) region and the MYPPPY region indicating the location and side-chain orientation of the avidity enhancing mutations, L104 and A29.

FIGS. 33: Reduction in soluble ICAM-1 and soluble E-selectin levels mean change from baseline at Day 85 as described in Example 3, infra.

DETAILED DESCRIPTION OF THE INVENTION

Definitions

Figure 2:
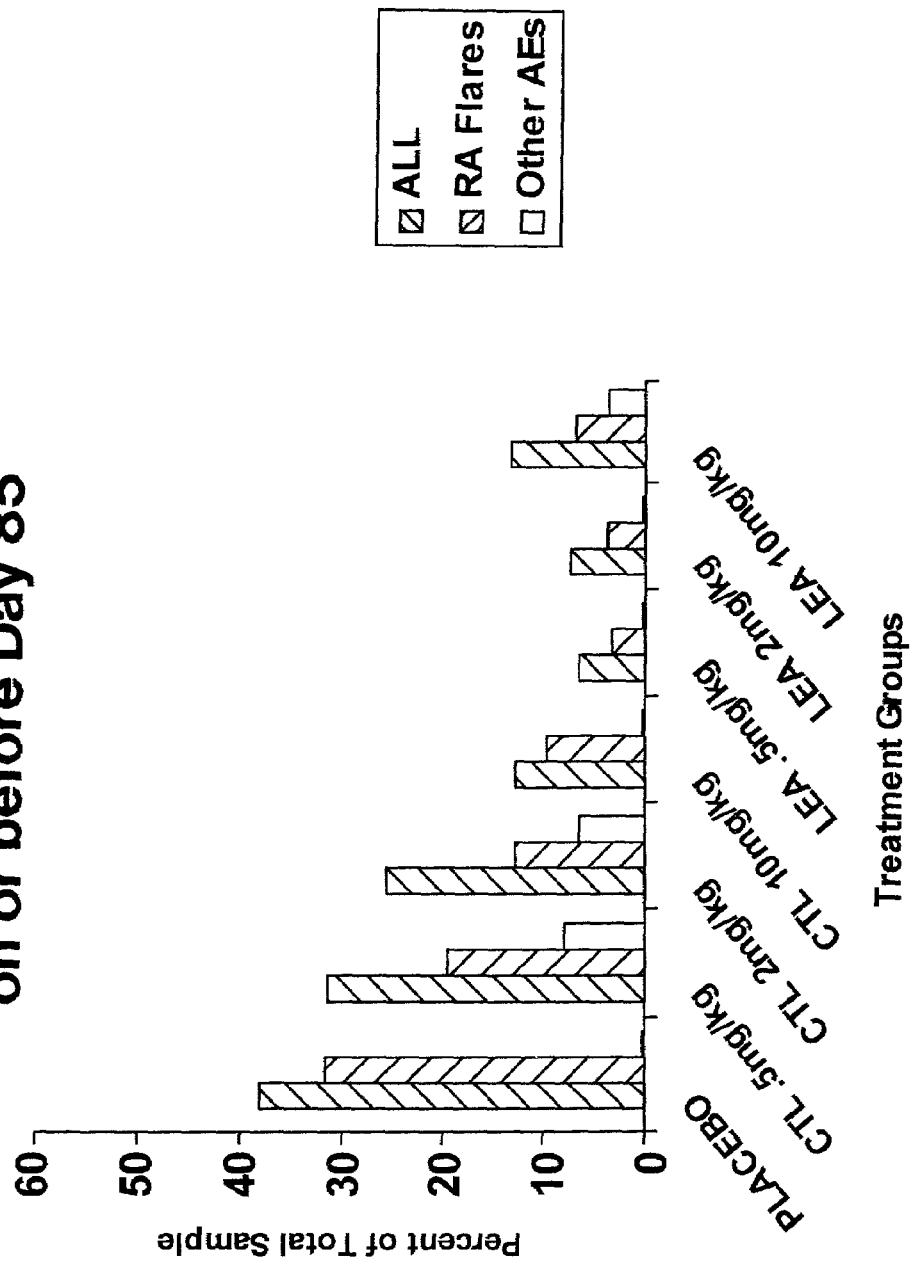
FIG. 2: Summary of discontinuations at day 85 by reason as described in Example 3, infra.

All scientific and technical terms used in this application have meanings commonly used in the art unless otherwise specified. As used in this application, the following words or phrases have the meanings specified.

As used herein, "ligand" refers to a molecule that specifically recognizes and binds another molecule, for example, a ligand for CTLA4 is a B7 molecule.

As used herein "wild type CTLA4" or "non-mutated CTLA4" has the amino acid sequence of naturally occurring, full length CTLA4 as shown in FIG. 23 (also as described U.S. Pat. Nos. 5,434,131, 5,844,095, 5,851,795), or any portion or derivative thereof, that recognizes and binds a B7 or interferes with a B7 so that it blocks binding to CD28 and/or CTLA4 (e.g., endogenous CD28 and/or CTLA4). In particular embodiments, the extracellular domain of wild type CTLA4 begins with methionine at position +1 and ends at aspartic acid at position +124, or the extracellular domain of wild type CTLA4 begins with alanine at position −1 and ends at aspartic acid at position +124. Wild type CTLA4 is a cell surface protein, having an N-terminal extracellular domain, a transmembrane domain, and a C-terminal cytoplasmic domain. The extracellular domain binds to target molecules, such as a B7 molecule. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. Alternatively, the signal peptide may not be removed completely, generating molecules that begin before the common starting amino acid methionine. Thus, the mature CTLA4 protein may start at methionine at position +1 or alanine at position −1. The mature form of the CTLA4 molecule includes the extracellular domain or any portion thereof, which binds to B7.

As used herein, a "CTLA4 mutant molecule" means wild-type CTLA4 as shown in FIG. 23 or any portion or derivative thereof, that has a mutation or multiple mutations (preferably in the extracellular domain of wildtype CTLA4). A CTLA4 mutant molecule has a sequence that it is similar but not identical to the sequence of wild type CTLA4 molecule, but still binds a B7. The mutations may include one or more amino acid residues substituted with an amino acid having conservative (e.g., substitute a leucine with an isoleucine) or non-conservative (e.g., substitute a glycine with a tryptophan) structure or chemical properties, amino acid deletions, additions, frameshifts, or truncations. CTLA4 mutant molecules may include a non-CTLA4 molecule therein or attached thereto. The mutant molecules may be soluble (i.e., circulating) or bound to a cell surface. Additional CTLA4 mutant molecules include those described in U.S. patent application Ser. Nos. 09/865,321, 60/214,065 and 60/287,576; in U.S. Pat. Nos. 6,090,914 5,844,095 and 5,773,253; and as described by Peach, R. J., et al., in *J Exp Med* 180: 2049-2058 (1994)). CTLA4 mutant molecules can be made synthetically or recombinantly.

"CTLA4Ig" is a soluble fusion protein comprising an extracellular domain of wildtype CTLA4 joined to an Ig tail, or a portion thereof that binds a B7. A particular embodiment comprises the extracellular domain of wild type CTLA4 (as shown in FIG. 23) starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 (DNA encoding CTLA4Ig was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; Linsley, P., et al., 1994 *Immunity* 1:793-80). CTLA4Ig-24, a Chinese Hamster Ovary (CHO) cell line expressing CTLA4Ig was deposited on May 31, 1991 with ATCC identification number CRL-10762). The soluble CTLA4Ig molecules used in the methods and/or kits of the invention may or may not include a signal (leader) peptide sequence. Typically, in the methods and/or kits of the invention, the molecules do not include a signal peptide sequence.

"L104EA29YIg" is a fusion protein that is a soluble CTLA4 mutant molecule comprising an extracellular domain of wildtype CTLA4 with amino acid changes A29Y (a tyrosine amino acid residue substituting for an alanine at position 29) and L104E (a glutamic acid amino acid residue substituting for a leucine at position +104), or a portion thereof that binds a B7 molecule, joined to an Ig tail (included in FIG. 19; DNA encoding L104EA29YIg was deposited on Jun. 20, 2000 with ATCC number PTA-2104; copending in U.S. patent application Ser. Nos. 09/579,927, 60/287,576 and 60/214,065, incorporated by reference herein). The soluble L104EA29YIg molecules used in the methods and/or kits of the invention may or may not include a signal (leader) peptide sequence. Typically, in the methods and/or kits of the invention, the molecules do not include a signal peptide sequence.

As used herein, "soluble" refers to any molecule, or fragments and derivatives thereof, not bound or attached to a cell, i.e., circulating. For example, CTLA4, B7 or CD28 can be made soluble by attaching an immunoglobulin (Ig) moiety to the extracellular domain of CTLA4, B7 or CD28, respectively. Alternatively, a molecule such as CTLA4 can be rendered soluble by removing its transmembrane domain. Typically, the soluble molecules used in the methods of the invention do not include a signal (or leader) sequence.

As used herein, "soluble CTLA4 molecules" means non-cell-surface-bound (i.e. circulating) CTLA4 molecules or any functional portion of a CTLA4 molecule that binds B7 including, but not limited to: CTLA4Ig fusion proteins (e.g. ATCC 68629), wherein the extracellular domain of CTLA4 is fused to an immunoglobulin (Ig) moiety rendering the fusion molecule soluble, or fragments and derivatives thereof, proteins with the extracellular domain of CTLA4 fused or joined with a portion of a biologically active or chemically active protein such as the papillomavirus E7 gene product (CTLA4-E7), melanoma-associated antigen p97 (CTLA4-p97) or HIV env protein (CTLA4-env gp120), or fragments and derivatives thereof; hybrid (chimeric) fusion proteins such as CD28/CTLA4Ig, or fragments and derivatives thereof; CTLA4 molecules with the transmembrane domain removed to render the protein soluble (Oaks, M. K., et al., 2000 *Cellular Immunology* 201:144-153), or fragments and derivatives thereof. "Soluble CTLA4 molecules" also include fragments, portions or derivatives thereof, and soluble CTLA4 mutant molecules, having CTLA4 binding activity. The soluble CTLA4 molecules used in the methods of the invention may or may not include a signal (leader) peptide sequence. Typically, in the methods of the invention, the molecules do not include a signal peptide sequence.

As used herein "the extracellular domain of CTLA4" is the portion of CTLA4 that recognizes and binds CTLA4 ligands, such as B7 molecules. For example, an extracellular domain of CTLA4 comprises methionine at position +1 to aspartic acid at position +124 (FIG. 23). Alternatively, an extracellular domain of CTLA4 comprises alanine at position −1 to aspartic acid at position +124 (FIG. 23). The extracellular domain includes fragments or derivatives of CTLA4 that bind a B7 molecule. The extracellular domain of CTLA4 as shown in FIG. 23 may also include mutations that change the binding avidity of the CTLA4 molecule for a B7 molecule.

As used herein, the term "mutation" means a change in the nucleotide or amino acid sequence of a wildtype molecule, for example, a change in the DNA and/or amino acid sequences of the wild-type CTLA4 extracellular domain. A mutation in DNA may change a codon leading to a change in the amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence as is well understood in the art. In that regard, certain nucleotide codons encode the same amino acid.

Examples include nucleotide codons CGU, CGG, CGC, and CGA encoding the amino acid, arginine (R); or codons GAU, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |

-continued

| Amino Acid | Symbol | One Letter Symbol | Codons |
|---|---|---|---|
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The mutant molecule may have one or more mutations.

As used herein, a "non-CTLA4 protein sequence" or "non-CTLA4 molecule" means any protein molecule that does not bind B7 and does not interfere with the binding of CTLA4 to its target. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,637,481, 5,844,095 and 5,434,131).

As used herein, a "fragment" or "portion" is any part or segment of a CTLA4 molecule, preferably the extracellular domain of CTLA4 or a part or segment thereof, that recognizes and binds its target, e.g., a B7 molecule.

As used herein, "B7" refers to the B7 family of molecules including, but not limited to, B7-1 (CD80), B7-2 (CD86) and B7-3 that may recognize and bind CTLA4 and/or CD28.

As used herein, "B7-positive cells" are any cells with one or more types of B7 molecules expressed on the cell surface.

As used herein, a "derivative" is a molecule that shares sequence homology and activity of its parent molecule. For example, a derivative of CTLA4 includes a soluble CTLA4 molecule having an amino acid sequence at least 70% similar to the extracellular domain of wildtype CTLA4, and which recognizes and binds B7 e.g. CTLA4Ig or soluble CTLA4 mutant molecule L104EA29YIg.

As used herein, to "block" or "inhibit" a receptor, signal or molecule means to interfere with the activation of the receptor, signal or molecule, as detected by an art-recognized test. For example, blockage of a cell-mediated immune response can be detected by determining reduction of Rheumatic Disease associated symptoms. Blockage or inhibition may be partial or total.

As used herein, "blocking B7 interaction" means to interfere with the binding of B7 to its ligands, such as CD28 and/or CTLA4, thereby obstructing T-cell and B7-positive cell interactions. Examples of agents that block B7 interactions include, but are not limited to, molecules such as an antibody (or portion or derivative thereof) that recognizes and binds to the any of CTLA4, CD28 or B7 molecules (e.g. B7-1, B7-2); a soluble form (or portion or derivative thereof) of the molecules such as soluble CTLA4; a peptide fragment or other small molecule designed to interfere with the cell signal through the CTLA4/CD28/B7-mediated interaction. In a preferred embodiment, the blocking agent is a soluble CTLA4 molecule, such as CTLA4Ig (ATCC 68629) or L104EA29YIg (ATCC PTA-2104), a soluble CD28 molecule such as CD28Ig (ATCC 68628), a soluble B7 molecule such as B7Ig (ATCC 68627), an anti-B7 monoclonal antibody (e.g. ATCC HB-253, ATCC CRL-2223, ATCC CRL-2226, ATCC HB-301, ATCC HB-11341 and monoclonal antibodies as described in by Anderson et al in U.S. Pat. No. 6,113,898 or Yokochi et al., 1982. J. Immun., 128(2)823-827), an anti-CTLA4 monoclonal antibody (e.g. ATCC HB-304, and monoclonal antibodies as described in references 82-83) and/or an anti-CD28 monoclonal antibody (e.g. ATCC HB 11944 and mAb 9.3 as described by Hansen (Hansen et al., 1980. Immunogenetics 10: 247-260) or Martin (Martin et al., 1984. J. Clin. Immun., 4(1):18-22)).

As used herein, "immune system disease" means any disease mediated by T-cell interactions with B7-positive cells including, but not limited to, autoimmune diseases, graft related disorders and immunoproliferative diseases. Examples of immune system diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis, T-cell lymphoma, T-cell acute lymphoblastic leukemia, testicular angiocentric T-cell lymphoma, benign lymphocytic angiitis, lupus (e.g. lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g. rheumatoid arthritis), polymyositis, scleroderma, and mixed connective tissue disease.

As used herein, "rheumatic diseases" means any disease that affects the joints, bone, soft tissue, or spinal cord (Mathies, H. 1983 *Rheuma*) and comprises inflammatory rheumatism, degenerative rheumatism, extra-articular rheumatism, and collagen diseases. Additionally, rheumatic diseases include, but are not limited to, chronic polyarthritis, psoriasis arthropathica, ankylosing spondylitis, rheumatoid arthritis, panarteriitis nodosa, systemic lupus erythematosus, progressive systemic scleroderma, periarthritis humeroscapularis, arthritis uratica, chondorcalcinosis, dermatomyositis, muscular rheumatism, myositis, and myogelosis. Some rheumatic diseases are known to be autoimmune diseases caused by a subject's altered immune response.

As used herein, "gene therapy" is a process to treat a disease by genetic manipulation so that a sequence of nucleic acid is transferred into a cell, the cell then expressing any genetic product encoded by the nucleic acid. For example, as is well known by those skilled in the art, nucleic acid transfer may be performed by inserting an expression vector containing the nucleic acid of interest into cells ex vivo or in vitro by a variety of methods including, for example, calcium phosphate precipitation, diethyaminoethyl dextran, polyethylene glycol (PEG), electroporation, direct injection, lipofection or viral infection (Sambrook et al., *Molecular Cloning: A Laboratory Manual* (Cold Spring Harbor Laboratory Press 1989); Kriegler M. *Gene Transfer ad Expression: A Laboratory Manual* (W. H. Freeman and Co, New York, N.Y., 1993) and Wu, *Methods in Enzymology* (Academic Press, New York, 1993), each of which is incorporated herein by reference).

Alternatively, nucleic acid sequences of interest may be transferred into a cell in vivo in a variety of vectors and by a variety of methods including, for example, direct administration of the nucleic acid into a subject (Williams et al, 1991 *PNAS* 88:2726-2730), or insertion of the nucleic acid into a viral vector and infection of the subject with the virus (Battleman et al, 1993 *J Neurosci* 13:94-951; Carroll et al, 1993 *J Cell Biochem* 17E:241; Lebkowski et al, U.S. Pat. No. 5,354,678; Davison and Elliott, Molecular Virology: A Practical Approach (IRL Press, New York, 1993)). Other methods used for in vivo transfer include encapsulation of the nucleic acid into liposomes, and direct transfer of the liposomes, or liposomes combined with a hemagglutinating Sendai virus, to a subject (U.S. Pat. No. 5,824,655, incorporated by reference herein). The transfected or infected cells express the protein products encoded by the nucleic acid in order to ameliorate a disease or the symptoms of a disease.

In order that the invention herein described may be more fully understood the following description is set forth.

Compositions and Methods of the Invention

The present invention provides compositions and methods for treating immune system diseases, such as rheumatic diseases, by administering to a subject an effective amount of a ligand that binds B7 for example, soluble CTLA4 molecules (such as CTLA4Ig and/or L104EA29YIg) and mAbs that recognize and bind B7. An effective amount is defined as the amount of soluble CTLA4 molecules that, when bound to B7 molecules on B7-positive cells, inhibit B7 molecules from binding endogenous ligands such as CTLA4 and CD28.

In a preferred embodiment, the immune disease is a rheumatic disease. Rheumatic diseases are any diseases which are characterized by (i) inflammation or degeneration of musculo-skeletal or connective tissue structures of the body, particularly the joints, and including muscles, tendons, cartilage, synovial and fibrous tissues, (ii) accompanied by joint swelling, joint tenderness, inflammation, morning stiffness, and/or pain, or impairment of locomotion or function of those structures and, in some cases, (iii) often accompanied by serological evidence of rheumatoid factor and other inflammatory surrogate markers.

Rheumatic diseases include, but are not limited to, rheumatoid arthritis. The symptoms of rheumatoid arthritis include joint swelling, joint tenderness, inflammation, morning stiffness, and pain leading to physical disability. Subjects afflicted with the advanced stages of arthritis suffer from symptoms of structural damage and debilitating pain. Other organs also can be impaired by the autoimmune mechanism.

Compositions

The present invention provides compositions for treating immune diseases, such as rheumatic diseases, comprising soluble CTLA4 molecules. Further, the present invention provides compositions comprising a biological agent that inhibits T-cell function but not T-cell depletion in a human by contacting B7-positive cells in the human with a soluble CTLA4. Examples of soluble CTLA4 include CTLA4Ig and soluble CTLA4 mutant molecule e.g. L104EA29YIg.

CTLA4 molecules, with mutant or wildtype sequences, may be rendered soluble by deleting the CTLA4 transmembrane segment (Oaks, M. K., et al., 2000 *Cellular Immunology* 201:144-153).

Alternatively, soluble CTLA4 molecules, with mutant or wildtype sequences, may be fusion proteins, wherein the CTLA4 molecules are fused to non-CTLA4 moieties such as immunoglobulin (Ig) molecules that render the CTLA4 molecules soluble. For example, a CTLA4 fusion protein may include the extracellular domain of CTLA4 fused to an immunoglobulin constant domain, resulting in the CTLA4Ig molecule (FIG. 24) (Linsley, P. S., et al., 1994 *Immunity* 1:793-80).

For clinical protocols, it is preferred that the immunoglobulin region does not elicit a detrimental immune response in a subject. The preferred moiety is the immunoglobulin constant region, including the human or monkey immunoglobulin constant regions. One example of a suitable immunoglobulin region is human Cγ1, including the hinge, CH2 and CH3 regions which can mediate effector functions such as binding to Fc receptors, mediating complement-dependent cytotoxicity (CDC), or mediate antibody-dependent cell-mediated cytotoxicity (ADCC). The immunoglobulin moiety may have one or more mutations therein, (e.g., in the CH2 domain, to reduce effector functions such as CDC or ADCC) where the mutation modulates the binding capability of the immunoglobulin to its ligand, by increasing or decreasing the binding capability of the immunoglobulin to Fc receptors. For example, mutations in the immunoglobulin may include changes in any or all its cysteine residues within the hinge domain, for example, the cysteines at positions +130, +136, and +139 are substituted with serine (FIG. 24). The immunoglobulin molecule may also include the proline at position +148 substituted with a serine, as shown in FIG. 24. Further, the mutations in the immunoglobulin moiety may include having the leucine at position +144 substituted with phenylalanine, leucine at position +1 145 substituted with glutamic acid, or glycine at position +147 substituted with alanine.

Additional non-CTLA4 moieties for use in the soluble CTLA4 molecules or soluble CTLA4 mutant molecules include, but are not limited to, p97 molecule, env gp120 molecule, E7 molecule, and ova molecule (Dash, B. et al. 1994 *J. Gen. Virol.* 75 (Pt 6):1389-97; Ikeda, T., et al. 1994 *Gene* 138(1-2):193-6; Falk, K., et al. 1993 *Cell. Immunol.* 150(2):447-52; Fujisaka, K. et al. 1994 *Virology* 204(2):789-93). Other molecules are also possible (Gerard, C. et al. 1994 *Neuroscience* 62(3):721; Byrn, R. et al. 1989 63(10):4370; Smith, D. et al. 1987 *Science* 238:1704; Lasky, L. 1996 *Science* 233:209).

The soluble CTLA4 molecule of the invention can include a signal peptide sequence linked to the N-terminal end of the extracellular domain of the CTLA4 portion of the molecule. The signal peptide can be any sequence that will permit secretion of the molecule, including the signal peptide from oncostatin M (Malik, et al., (1989) *Molec. Cell. Biol.* 9: 2847-2853), or CD5 (Jones, N. H. et al., (1986) *Nature* 323:346-349), or the signal peptide from any extracellular protein.

The soluble CTLA4 molecule of the invention can include the oncostatin M signal peptide linked at the N-terminal end of the extracellular domain of CTLA4, and the human immunoglobulin molecule (e.g., hinge, CH2 and CH3) linked to the C-terminal end of the extracellular domain (wildtype or mutated) of CTLA4. This molecule includes the oncostatin M signal peptide encompassing an amino acid sequence having methionine at position −26 through alanine at position −1, the CTLA4 portion encompassing an amino acid sequence having methionine at position +1 through aspartic acid at position +124, a junction amino acid residue glutamine at position +125, and the immunoglobulin portion encompassing an amino acid sequence having glutamic acid at position +126 through lysine at position +357.

Specifically, the soluble CTLA4 mutant molecules of the invention, comprising the mutated CTLA4 sequences described infra, are fusion molecules comprising human IgCγ1 moieties fused to the mutated CTLA4 fragments.

In one embodiment, the soluble CTLA4 mutant molecules comprise IgCγ1 fused to a CTLA4 fragment comprising a single-site mutation in the extracellular domain. The extracellular domain of CTLA4 comprises methionine at position +1 through aspartic acid at position +124 (e.g., FIG. 23). The extracellular portion of the CTLA4 can comprise alanine at position −1 through aspartic acid at position +124 (e.g., FIG. 23). Examples of single-site mutations include the following wherein the leucine at position +104 is changed to any other amino acid:

| Single-site mutant: | Codon change: |
|---|---|
| L104EIg | Glutamic acid GAG |
| L104SIg | Serine AGT |
| L104TIg | Threonine ACG |
| L104AIg | Alanine GCG |
| L104WIg | Tryptophan TGG |
| L104QIg | Glutamine CAG |
| L104KIg | Lysine AAG |
| L104RIg | Arginine CGG |
| L104GIg | Glycine GGG |

Further, the invention provides mutant molecules having the extracellular domain of CTLA4 with two mutations, fused to an Ig Cγ1 moiety. Examples include the following wherein the leucine at position +104 is changed to another amino acid (e.g. glutamic acid) and the glycine at position +105, the serine at position +25, the threonine at position +30 or the alanine at position +29 is changed to any other amino acid:

| Double-site mutants: | Codon change: |
|---|---|
| L104EG105FIg | Phenylalanine TTC |
| L104EG105WIg | Tryptophan TGG |
| L104EG105LIg | Leucine CTT |
| L104ES25RIg | Arginine CGG |
| L104ET30GIg | Glycine GGG |
| L104ET30NIg | Asparagine AAT |
| L104EA29YIg | Tyrosine TAT |
| L104EA29LIg | Leucine TTG |
| L104EA29TIg | Threonine ACT |
| L104EA29WIg | Tryptophan TGG |

Further still, the invention provides mutant molecules having the extracellular domain of CTLA4 comprising three mutations, fused to an Ig Cγ1 moiety. Examples include the following wherein the leucine at position +104 is changed to another amino acid (e.g. glutamic acid), the alanine at position +29 is changed to another amino acid (e.g. tyrosine) and the serine at position +25 is changed to another amino acid:

| Triple-site Mutants: | Codon changes: |
|---|---|
| L104EA29YS25KIg | Lysine AAA |
| L104EA29YS25KIg | Lysine AAG |
| L104EA29YS25NIg | Asparagine AAC |
| L104EA29YS25RIg | Arginine CGG |

Soluble CTLA4 mutant molecules may have a junction amino acid residue which is located between the CTLA4 portion and the Ig portion of the molecule. The junction amino acid can be any amino acid, including glutamine. The junction amino acid can be introduced by molecular or chemical synthesis methods known in the art.

The present invention provides CTLA4 mutant molecules including a signal peptide sequence linked to the N-terminal end of the extracellular domain of the CTLA4 portion of the mutant molecule. The signal peptide can be any sequence that will permit secretion of the mutant molecule, including the signal peptide from oncostatin M (Malik, et al., 1989 *Molec. Cell. Biol.* 9: 2847-2853), or CD5 (Jones, N. H. et al., 1986 *Nature* 323:346-349), or the signal peptide from any extracellular protein.

The invention provides soluble CTLA4 mutant molecules comprising a single-site mutation in the extracellular domain of CTLA4 such as L104EIg (as included in FIG. 18) or L104SIg, wherein L104EIg and L104SIg are mutated in their CTLA4 sequences so that leucine at position +104 is substituted with glutamic acid or serine, respectively. The single-site mutant molecules further include CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated so that the cysteines at positions +130, +136, and +139 are substituted with serine, and the proline at position +148 is substituted with serine. Alternatively, the single-site soluble CTLA4 mutant molecule may have a CTLA4 portion encompassing alanine at position −1 through aspartic acid at position +124.

The invention provides soluble CTLA4 mutant molecules comprising a double-site mutation in the extracellular domain of CTLA4, such as L104EA29YIg, L104EA29LIg, L104EA29TIg or L104EA29WIg, wherein leucine at position +104 is substituted with a glutamic acid and alanine at position +29 is changed to tyrosine, leucine, threonine and tryptophan, respectively. The sequences for L104EA29YIg, L104EA29LIg, L104EA29TIg and L104EA29WIg, starting at methionine at position +1 and ending with lysine at position +357, plus a signal (leader) peptide sequence are included in the sequences as shown in FIGS. 19-22 respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a double-site mutation in the extracellular domain of CTLA4, such as L104EG105FIg, L104EG105WIg and L104EG105LIg, wherein leucine at position +104 is substituted with a glutamic acid and glycine at position +105 is substituted with phenylalanine, tryptophan and leucine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides L104ES25RIg which is a double-site mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with arginine, and leucine at position +104 is substituted with glutamic acid. Alternatively, L104ES25RIg can have a CTLA4 portion encompassing alanine at position −1 through aspartic acid at position +124.

The invention provides soluble CTLA4 mutant molecules comprising a double-site mutation in the extracellular domain of CTLA4, such as L104ET30GIg and L104ET30NIg, wherein leucine at position +104 is substituted with a glutamic acid and threonine at position +30 is substituted with glycine and asparagine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a triple-site mutation in the extracellular domain of CTLA4, such as L104EA29YS25KIg, L104EA29YS25NIg, L104EA29YS25RIg, wherein leucine at position +104 is substituted with a glutamic acid, alanine at position +29 is changed to tyrosine and serine at position +25 is changed to lysine, asparagine and arginine, respectively. The triple-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine.

Alternatively, these mutant molecules can have a CTLA4 portion encompassing alanine at position −1 through aspartic acid at position +124.

Additional embodiments of soluble CTLA4 mutant molecules include chimeric CTLA4/CD28 homologue mutant molecules that bind a B7 (Peach, R. J., et al., 1994 *J Exp Med* 180:2049-2058). Examples of these chimeric CTLA4/CD28 mutant molecules include HS1, HS2, HS3, HS4, HS5, HS6, HS4A, HS4B, HS7, HS8, HS9, HS10, HS11, HS12, HS13 and HS14 (U.S. Pat. No. 5,773,253)

Preferred embodiments of the invention are soluble CTLA4 molecules such as CTLA4Ig (as shown in FIG. 24, starting at methionine at position +1 and ending at lysine at position +357) and soluble CTLA4 mutant L104EA29YIg (as shown in FIG. 19, starting at methionine at position +1 and ending at lysine at position +357). The invention further provides nucleic acid molecules comprising nucleotide sequences encoding the amino acid sequences corresponding to the soluble CTLA4 molecules of the invention. In one embodiment, the nucleic acid molecule is a DNA (e.g., cDNA) or a hybrid thereof. DNA encoding CTLA4Ig (FIG. 24) was deposited on May 31, 1991 with the American Type Culture Collection (ATCC), 10801 University Blvd., Manassas, Va. 20110-2209 and has been accorded ATCC accession number ATCC 68629. DNA encoding L104EA29YIg (sequence included in FIG. 19) was deposited on Jun. 19, 2000 with ATCC and has been accorded ATCC accession number PTA-2104. Alternatively, the nucleic acid molecules are RNA or a hybrid thereof.

Additionally, the invention provides a vector, which comprises the nucleotide sequences of the invention. Examples of expression vectors for include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pCDNA-3 (Invitrogen) or modified forms thereof, adenoviral vectors; adeno-associated virus vectors, baculovirus vectors, yeast vectors (e.g., pESC vectors (Stratagene)).

A host vector system is also provided. The host vector system comprises the vector of the invention in a suitable host cell. Examples of suitable host cells include, but are not limited to, prokaryotic and eukaryotic cells. In accordance with the practice of the invention, eukaryotic cells are also suitable host cells. Examples of eukaryotic cells include any animal cell, whether primary or immortalized, yeast (e.g., *Saccharomces cerevisiae, Schizosaccharomyces pombe,* and *Pichia pastoris*), and plant cells. Myeloma, COS and CHO cells are examples of animal cells that may be used as hosts. Particular CHO cells include, but are not limited to, DG44 (Chasin, et la., 1986 *Som. Cell. Molec. Genet.* 12:555-556; Kolkekar 1997 *Biochemistry* 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

The CTLA4 mutant molecules of the invention may be isolated as naturally-occurring polypeptides, or from any source whether natural, synthetic, semi-synthetic or recombinant. Accordingly, the CTLA4 mutant polypeptide molecules may be isolated as naturally-occurring proteins from any species, particularly mammalian, including bovine, ovine, porcine, murine, equine, and preferably human. Alternatively, the CTLA4 mutant polypeptide molecules may be isolated as recombinant polypeptides that are expressed in prokaryote or eukaryote host cells, or isolated as a chemically synthesized polypeptide.

A skilled artisan can readily employ standard isolation methods to obtain isolated CTLA4 mutant molecules. The nature and degree of isolation will depend on the source and the intended use of the isolated molecules.

CTLA4 mutant molecules and fragments or derivatives thereof, can be produced by recombinant methods. Accordingly, an isolated nucleotide sequence encoding wild-type CTLA4 molecules may be manipulated to introduce mutations, resulting in nucleotide sequences that encode the CTLA4 mutant polypeptide molecules. For example, the nucleotide sequences encoding the CTLA4 mutant molecules may be generated by site-directed mutagenesis methods, using primers and PCR amplification. The primers can include specific sequences designed to introduce desired mutations. Alternatively, the primers can be designed to include randomized or semi-randomized sequences to introduce random mutations. Standard recombinant methods (*Molecular Cloning; A Laboratory Manual*, $2^{nd}$ edition, Sambrook, Fritch, and Maniatis 1989, Cold Spring Harbor Press) and PCR technology (U.S. Pat. No. 4,603,102) can be employed for generating and isolating CTLA4 mutant polynucleotides encoding CTLA4 mutant polypeptides.

The invention includes pharmaceutical compositions for use in the treatment of immune system diseases comprising pharmaceutically effective amounts of soluble CTLA4 molecules. In certain embodiments, the immune system diseases are mediated by CD28/CTLA4/B7 interactions. The soluble CTLA4 molecules are preferably soluble CTLA4 molecules with wildtype sequence and/or soluble CTLA4 molecules having one or more mutations in the extracellular domain of CTLA4. The pharmaceutical composition can include soluble CTLA4 protein molecules and/or nucleic acid molecules, and/or vectors encoding the molecules. In preferred embodiments, the soluble CTLA4 molecules have the amino acid sequence of the extracellular domain of CTLA4 as shown in either FIG. 24 or 19 (CTLA4Ig or L104EA29Y, respectively). Even more preferably, the soluble CTLA4 mutant molecule is L104EA29YIg as disclosed herein. The compositions may additionally include other therapeutic agents, including, but not limited to, drug toxins, enzymes, antibodies, or conjugates.

As is standard practice in the art, pharmaceutical compositions, comprising the molecules of the invention admixed with an acceptable carrier or adjuvant which is known to those of skill of the art, are provided. The pharmaceutical compositions preferably include suitable carriers and adjuvants which include any material which when combined with the molecule of the invention (e.g., a soluble CTLA4 molecule, such as, CTLA4Ig or L104EA29Y) retains the molecule's activity and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

Methods

The invention provides methods for regulating functional CTLA4- and CD28-positive cell interactions with B7-positive cells. The methods comprise contacting the B7-positive cells with a soluble CTLA4 molecule of the invention so as to form soluble CTLA4/B7 complexes, the complexes interfering with reaction of an endogenous CTLA4 and/or CD28 molecule with a B7 molecule.

The present invention also provides methods for inhibiting T-cell function but not T-cell depletion in a human by contacting B7-positive cells in the human with a soluble CTLA4. Examples of soluble CTLA4 include CTLA4Ig and soluble CTLA4 mutant molecule e.g. L104EA29YIg.

The present invention further provides methods for treating immune system diseases such as rheumatic diseases. The methods comprise administering a therapeutic composition, comprising soluble CTLA4 molecules of the invention, to a subject in an amount effective to relieve at least one of the symptoms associated with immune system diseases. Additionally, the invention may provide long-term therapy for immune system diseases by blocking the T-cell/B7-positive cell interactions, thereby blocking T-cell stimulation by co-stimulatory signals such as B7 binding to CD28, leading to induction of T-cell anergy or tolerance. Immune system diseases include, but are not limited to, autoimmune diseases, immunoproliferative diseases, and graft-related disorders. Examples of graft-related diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis; T cell lymphoma; T cell acute lymphoblastic leukemia; testicular angiocentric T cell lymphoma; benign lymphocytic angiitis; and autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitis, type I diabetes mellitis, type II diabetes mellitis), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g., rheumatoid arthritis), polymyositis, scleroderma, and mixed connective tissue disease.

The soluble CTLA4 molecules of the invention exhibit inhibitory properties in vivo. Under conditions where T-cell/B7-positive cell interactions, for example T cell/B cell interactions, are occurring as a result of contact between T cells and B7-positive cells, binding of introduced CTLA4 molecules to react to B7-positive cells, for example B cells, may interfere, i.e., inhibit, the T cell/B7-positive cell interactions resulting in regulation of immune responses.

The invention provides methods for downregulating immune responses. Down regulation of an immune response by the soluble CTLA4 molecules of the invention may be by way of inhibiting or blocking an immune response already in progress or may involve preventing the induction of an immune response. The soluble CTLA4 molecules of the invention may inhibit the functions of activated T cells, such as T lymphocyte proliferation and cytokine secretion, by suppressing T cell responses or by inducing specific tolerance in T cells, or both. Further, the soluble CTLA4 molecules of this invention, interfering with the CTLA4/CD28/B7 pathway may inhibit T-cell proliferation and/or cytokine secretion, and thus result in reduced tissue destruction and induction of T-cell unresponsiveness or anergy.

A preferred embodiment of the invention comprises use of the soluble CTLA4 mutant molecule L104EA29YIg to regulate functional CTLA4- and CD28-positive cell interactions with B7-positive cells, to treat immune system diseases such as rheumatic diseases and/or to downregulate immune responses. The L104EA29YIg of the invention is a soluble CTLA4 mutant molecule comprising at least the two amino acid changes, the leucine (L) to glutamic acid (E) at position +104 and the alanine (A) to tyrosine (Y) change at position +29. The L104EA29YIg molecule may encompass further mutations beyond the two specified herein.

A preferred embodiment includes methods for treating a rheumatic disease, such as rheumatoid arthritis, by administering an effective amount of soluble CTLA4 molecules to a subject. Administration of an effective amount of the therapeutic composition, thereby relieving the subject of at least one of the symptoms associated with the disease, including reducing: joint swelling, joint tenderness, inflammation, morning stiffness, and pain, and structural damage subsequently decreasing the physical disability. The methods of the invention also may be used to reduce at least one symptom associated with rheumatoid arthritis, including reducing erythrocyte sedimentation rates, serum levels of C-reactive protein, soluble ICAM-1, soluble E-selectin and/or soluble IL-2r.

The amount of symptom relief provided by the present invention can be measured using any of the accepted criteria established to measure and document symptom relief in a clinical setting. Acceptable criteria for measuring symptom relief may include scores based on the criteria established by the American College of Rheumatology (e.g., ACR 20), the four measures of symptom relief (in: "CDER Guideline for the Clinical Evaluation of Anti-Inflammatory and Antirheumatic Drugs—FDA 1988), and the Health Assessment Questionnaire (HAQ) (Fries, J. F., et al., 1982 J. of Rheumatology 9:789-793). For a general description of these criteria, see "Guidance for Industry: Clinical Development Programs for Drugs, Devices, and Biological products for the Treatment of Rheumatoid Arthritis (RA)", February 1999.

The subjects treated by the present invention include mammalian subjects, including, human, monkey, ape, dog, cat, cow, horse, rabbit, mouse and rat.

The present invention provides various methods, local or systemic, for administering the soluble CTLA4 molecule. The methods include intravenous, intramuscular, intraperitoneal, oral, inhalation and subcutaneous methods, as well as implantable pump, continuous infusion, gene therapy, liposomes, suppositories, topical contact, vesicles, capsules and injection methods. The therapeutic agent, compounded with a carrier, is commonly lyophilized for storage and is reconstituted with water or a buffered solution with a neutral pH (about pH 7-8, e.g., pH 7.5) prior to administration.

As is standard practice in the art, the compositions of the invention may be administered to the subject in any pharmaceutically acceptable form.

In accordance with the practice of the invention, the methods comprise administering to a subject the soluble CTLA4 molecules of the invention to regulate CD28- and/or CTLA4-positive cell interactions with B7-positive cells. The B7-positive cells are contacted with an effective amount of the soluble CTLA4 molecules of the invention, or fragments or derivatives thereof, so as to form soluble CTLA4/B7 complexes. The complexes interfere with interaction between endogenous CTLA4 and CD28 molecules with B7 family molecules.

The soluble CTLA4 molecules may be administered to a subject in an amount and for a time (e.g. length of time and/or multiple times) sufficient to block endogenous B7 molecules from binding their respective ligands, in the subject. Blockage of endogenous B7/ligand binding thereby inhibiting interactions between B7-positive cells with CD28- and/or CTLA4-positive cells.

Dosage of a therapeutic agent is dependant upon many factors including, but not limited to, the type of tissue affected, the type of autoimmune disease being treated, the severity of the disease, a subject's health and response to the treatment with the agents. Accordingly, dosages of the agents can vary depending on each subject and the mode of administration. The soluble CTLA4 molecules may be administered in an amount between 0.1 to 20.0 mg/kg weight of the patient/day, preferably between 0.5 to 10.0 mg/kg/day.

The invention also encompasses the use of the compositions of the invention together with other pharmaceutical agents to treat immune system diseases. For example, rheumatic diseases may be treated with molecules of the invention in conjunction with, but not limited to, immunosuppressants such as corticosteroids, cyclosporin (Mathiesen 1989 Cancer Lett. 44(2):151-156), prednisone, azathioprine, methotrexate (R. Handschumacher, in: "Drugs Used for Immunosuppression" pages 1264-1276), TNFα blockers or antagonists (New England Journal of Medicine, vol. 340: 253-259, 1999; The Lancet vol. 354: 1932-39, 1999, Annals of Internal Medicine, vol. 130: 478-486), or any other biological agent targeting any inflammatory cytokine, nonsteroidal antiinflammatory drugs/Cox-2 inhibitors, hydroxychloroquine, sulphasalazopryine, gold salts, etanercept, infliximab, rapamycin, mycophenolate mofetil, azathioprine, tacrolismus, basiliximab, cytoxan, interferon beta-1a, interferon beta-1b, glatiramer acetate, mitoxantrone hydrochloride, anakinra and/or other biologics.

The soluble CTLA4 molecules (preferably, L104EA29YIg) can also be used in combination with one or more of the following agents to regulate an immune response: soluble gp39 (also known as CD40 ligand (CD40L), CD154, T-BAM, TRAP), soluble CD29, soluble CD40, soluble CD80 (e.g. ATCC 68627), soluble CD86, soluble CD28 (e.g. 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g. ATCC HB-10916, ATCC HB-12055 and ATCC HB-12056), antibodies reactive with CD40 (e.g. ATCC HB-9110), antibodies reactive with B7 (e.g. ATCC HB-253, ATCC CRL-2223, ATCC CRL-2226, ATCC HB-301, ATCC HB-11341, etc), antibodies reactive with CD28 (e.g. ATCC HB-11944 or mAb 9.3 as described by Martin et al (J. Clin. Immun. 4(1):18-22, 1980), antibodies reactive with LFA-1 (e.g. ATCC HB-9579 and ATCC TIB-213), antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-1 (ATCC CRL-2252), ICAM-2 and ICAM-3), antibodies reactive with CTLA4 (e.g. ATCC HB-304),, antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44. In certain embodiments, monoclonal antibodies are preferred. In other embodiments, antibody fragments are preferred. As persons skilled in the art will readily understand, the combination can include the soluble CTLA4 molecules of the invention and one other immunosuppressive agent, the soluble CTLA4 molecules with two other immunosuppressive agents, the soluble CTLA4 molecules with three other immunosuppressive agents, etc. The determination of the optimal combination and dosages can be determined and optimized using methods well known in the art.

Some specific combinations include the following: L104EA29YIg and CD80 monoclonal antibodies (mAbs); L104EA29YIg and CD86 mAbs; L104EA29YIg, CD80 mAbs, and CD86 mAbs; L104EA29YIg and gp39 mAbs; L104EA29YIg and CD40 mAbs; L104EA29YIg and CD28 mAbs; L104EA29YIg, CD80 and CD86 mAbs, and gp39 mAbs; L104EA29YIg, CD80 and CD86 mAbs and CD40 mAbs; and L104EA29YIg, anti-LFA1 mAb, and anti-gp39 mAb. A specific example of a gp39 mAb is MR1. Other combinations will be readily appreciated and understood by persons skilled in the art.

The soluble CTLA4 molecules of the invention, for example L104EA29YIg, may be administered as the sole active ingredient or together with other drugs in immunomodulating regimens or other anti-inflammatory agents e.g. for the treatment or prevention of allo- or xenograft acute or chronic rejection or inflammatory or autoimmune disorders, or to induce tolerance. For example, it may be used in combination with a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g. CTLA4/CD28-Ig, or other adhesion molecule inhibitors, e.g. mAbs or low molecular weight inhibitors including LFA-1 antagonists, Selectin antagonists and VLA-4 antagonists. The compound is particularly useful in combination with a compound that interferes with CD40 and its ligand, e.g. antibodies to CD40 and antibodies to CD40-L.

Where the soluble CTLA4 mutant molecules of the invention are administered in conjunction with other immunosuppressive/immunomodulatory or anti-inflammatory therapy, e.g. as hereinabove specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth.

In accordance with the foregoing the present invention provides in a yet further aspect methods as defined above comprising co-administration, e.g. concomitantly or in sequence, of a therapeutically effective amount of soluble CTLA4 molecules of the invention, e.g. CTLA4Ig and/or L104EA29YIg, in free form or in pharmaceutically acceptable salt form, and a second drug substance, said second drug substance being an immunosuppressant, immunomodulatory or anti-inflammatory drug, e.g. as indicated above. Further provided are therapeutic combinations, e.g. a kit, e.g. for use in any method as defined above, comprising a soluble CTLA4 molecule, in free form or in pharmaceutically acceptable salt form, to be used concomitantly or in sequence with at least one pharmaceutical composition comprising an immunosuppressant, immunomodulatory or anti-inflammatory drug. The kit may comprise instructions for its administration.

The invention also provides methods for producing the soluble CTLA4 mutant molecules molecules of the invention.

Expression of soluble CTLA4 mutant molecules can be in prokaryotic cells or eukaryotic cells.

Prokaryotes most frequently are represented by various strains of bacteria. The bacteria may be a gram positive or a gram negative. Typically, gram-negative bacteria such as *E. coli* are preferred. Other microbial strains may also be used. Sequences encoding soluble CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, including such commonly used promoters as the beta-lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived $P_L$ promoter and N-gene ribosome binding site (Shimatake, et al., (1981) *Nature* 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to $CaCl_2$-shock (Cohen, (1972) *Proc. Natl. Acad. Sci. USA* 69:2110, and Sambrook et al. (eds.), "*Molecular Cloning: A Laboratory Manual*", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin, et la., 1986 *Som. Cell. Molec. Genet.* 12:555-556; Kolkekar 1997 *Biochemistry* 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

Nucleic acid sequences encoding the CTLA4 mutant molecules can also be inserted into a vector designed for expressing foreign sequences in an eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., (1973) *Nature* 273:113), or other viral promoters such as those derived from polyoma, Adenovirus 2, and bovine papilloma virus. An inducible promoter, such as hMTII (Karin, et al., (1982) *Nature* 299:797-802) may also be used.

Vectors for expressing CTLA4 mutant molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, (1983) *Meth. Enz.* 101:307). Alternatively, sequences from the yeast genome capable of promoting autonomous replication can be used (see, for example, Stinchcomb et al., (1979) *Nature* 282:39); Tschemper et al., (1980) *Gene* 10:157; and Clarke et al., (1983) *Meth. Enz.* 101:300).

Transcriptional control sequences for yeast vectors include promoters for the synthesis of glycolytic enzymes (Hess et al., (1968) *J. Adv. Enzyme Reg.* 7:149; Holland et al., (1978) *Biochemistry* 17:4900). Additional promoters known in the art include the CMV promoter provided in the CDM8 vector (Toyama and Okayama, (1990) *FEBS* 268:217-221); the promoter for 3-phosphoglycerate kinase (Hitzeman et al., (1980) *J. Biol. Chem.* 255:2073), and those for other glycolytic enzymes.

Other promoters are inducible because they can be regulated by environmental stimuli or by the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include, but are not limited to, Agrobacterium $T_i$ plasmids, cauliflower mosaic virus (CaMV), and tomato golden mosaic virus (TGMV).

General aspects of mammalian cell host system transformations have been described by Axel (U.S. Pat. No. 4,399,216 issued Aug. 16, 1983). Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

Once the CTLA4 mutant molecules of the inventions are expressed, they can be harvested by methods well known in the art such as cell lysis (e.g. sonication, lysozyme and/or detergents) and protein recovery performed using standard protein purification means, e.g., affinity chromatography or ion-exchange chromatography, to yield substantially pure product (R. Scopes in: "*Protein Purifications Principles and Practice*", Third Edition, Springer-Verlag (1994); Sambrook et al. (eds.), "*Molecular Cloning: A Laboratory Manual*", 2nd Edition, Cold Spring Harbor Press, (1989)). Expression of CTLA4 mutant molecules can be detected by methods known in the art. For example, the mutant molecules can be detected by Coomassie staining SDS-PAGE gels and immunoblotting using antibodies that bind CTLA4.

The following examples are presented to illustrate the present invention and to assist one of ordinary skill in making and using the same. The examples are not intended in any way to otherwise limit the scope of the invention.

EXAMPLE 1

The following provides a description of the methods used to generate the nucleotide sequences encoding the CTLA4 molecules of the invention.

A CTLA4Ig encoding plasmid was first constructed, and shown to express CTLA4Ig molecules as described in U.S. Pat. Nos. 5,434,131, 5,885,579 and 5,851,795. Then single-site mutant molecules (e.g., L104EIg) were generated from the CTLA4Ig encoding sequence, expressed and tested for binding kinetics for various B7 molecules. The L104EIg nucleotide sequence (as included in the sequence shown in FIG. 18) was used as a template to generate the double-site CTLA4 mutant sequences (as included in the sequences shown in FIGS. 19-22) which were expressed as proteins and tested for binding kinetics. The double-site CTLA4 mutant sequences include: L104EA29YIg, L104EA29LIg, L104EA29TIg, and L104EA29WIg. Triple-site mutants were also generated.

CTLA4Ig Construction

A genetic construct encoding CTLA4Ig comprising the extracellular domain of CTLA4 and an IgCgamma1 domain was constructed as described in U.S. Pat. Nos. 5,434,131, 5,844,095 and 5,851,795, the contents of which are incorporated by reference herein. The extracellular domain of the CTLA4 gene was cloned by PCR using synthetic oligonucleotides corresponding to the published sequence (Dariavach et al., *Eur. Journ. Immunol.* 18:1901-1905 (1988)).

Because a signal peptide for CTLA4 was not identified in the CTLA4 gene, the N-terminus of the predicted sequence of CTLA4 was fused to the signal peptide of oncostatin M (Malik et al., *Mol. and Cell. Biol.* 9:2847 (1989)) in two steps using overlapping oligonucleotides. For the first step, the oligonucleotide, CTCAGTCTGGTCCTTGCACTCCT-GTTTCCAAGCATGGCGAGCATGGCAATGCA CGTG-GCCCAGCC (SEQ ID NO:1) (which encoded the C terminal 15 amino acids from the oncostatin M signal peptide fused to the N terminal 7 amino acids of CTLA4) was used as forward primer, and TTTGGGCTCCTGATCA-GAATCTGGGCACGGTTG (SEQ ID NO: 2) (encoding amino acid residues 119-125 of the amino acid sequence encoding CTLA4 receptor and containing a Bcl I restriction enzyme site) as reverse primer. The template for this step was cDNA synthesized from 1 micro g of total RNA from H38 cells (an HTLV II infected T-cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGCCACTGAAGCT-TCACCAATGGGTGTACTGCTCACACA-GAGGACGCTGCTCAGTCTGGTCCTTGCACTC (SEQ ID NO: 3) and the same reverse primer. The product of the PCR reaction was digested with Hind III and Bcl I and ligated together with a Bcl I/Xba I cleaved cDNA fragment encoding the amino acid sequences corresponding to the hinge, CH2 and CH3 regions of IgC(gamma)1 into the Hind III/Xba I cleaved expression vector, CDM8 or Hind III/Xba I cleaved expression vector piLN (also known as πLN).

DNA encoding the amino acid sequence corresponding to CTLA4Ig has been deposited with the ATCC under the Budapest Treaty on May 31, 1991, and has been accorded ATCC accession number 68629.

CTLA4Ig Codon Based Mutagenesis:

A mutagenesis and screening strategy was developed to identify mutant CTLA4Ig molecules that had slower rates of dissociation ("off" rates) from CD80 and/or CD86 molecules i.e. improved binding ability. In this embodiment, mutations were carried out in and/or about the residues in the CDR-1, CDR-2 (also known as the C' strand) and/or CDR-3 regions of the extracellular domain of CTLA4 (as described in U.S. Pat Nos. 6,090,914, 5,773,253 and 5,844,095; in copending U.S. patent application Ser. No. 60/214,065; and by Peach, R. J., et al *J Exp Med* 1994 180:2049-2058. A CDR-like region encompasses the each CDR region and extends, by several amino acids, upstream and/or downstream of the CDR motif). These sites were chosen based on studies of chimeric CD28/CTLA4 fusion proteins (Peach et al., *J. Exp. Med.,* 1994, 180:2049-2058), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues is considered part of the present invention.

To synthesize and screen soluble CTLA4 mutant molecules with altered affinities for a B7 molecule (e.g. CD80, CD86), a two-step strategy was adopted. The experiments entailed first generating a library of mutations at a specific codon of an extracellular portion of CTLA4 and then screening these by BIAcore analysis to identify mutants with altered reactivity to B7. The Biacore assay system (Pharmacia, Piscataway, N.J.) uses a surface plasmon resonance detector system that essentially involves covalent binding of either CD80Ig or CD86Ig to a dextran-coated sensor chip which is located in a detector. The test molecule can then be injected into the chamber containing the sensor chip and the amount of complementary protein that binds can be assessed based on the change in molecular mass which is physically associated with the dextran-coated side of the sensor chip; the change in molecular mass can be measured by the detector system.

Specifically, single-site mutant nucleotide sequences were generated using non-mutated (e.g., wild-type) DNA encoding CTLA4Ig (U.S. Pat. Nos.: 5,434,131, 5,844,095; 5,851,795; and 5,885,796; ATCC Accession No. 68629) as a template. Mutagenic oligonucleotide PCR primers were designed for random mutagenesis of a specific codon by allowing any base at positions 1 and 2 of the codon, but only guanine or thymine at position 3 (XXG/T or also noted as NNG/T). In this manner, a specific codon encoding an amino acid could be randomly mutated to code for each of the 20 amino acids. In that regard, XXG/T mutagenesis yields 32 potential codons encoding each of the 20 amino acids. PCR products encoding mutations in close proximity to the CDR3-like loop of CTLA4Ig (MYPPPY) (SEQ ID NO:20), were digested with SacI/XbaI and sub cloned into similarly cut CTLA4Ig (as included in FIG. 24) πLN expression vector. This method was used to generate the single-site CTLA4 mutant molecule L104EIg (as included in FIG. 18).

For mutagenesis in proximity to the CDR-1-like loop of CTLA4Ig, a silent NheI restriction site was first introduced 5' to this loop, by PCR primer-directed mutagenesis. PCR products were digested with NheI/XbaI and subcloned into similarly cut CTLA4Ig or L104EIg expression vectors. This method was used to generate the double-site CTLA4 mutant molecule L104EA29YIg (as included in FIG. 19). In particular, the nucleic acid molecule encoding the single-site CTLA4 mutant molecule, L104EIg, was used as a template to generate the double-site CTLA4 mutant molecule, L104EA29YIg.

The double-site mutant nucleotide sequences encoding CTLA4 mutant molecules, such as L104EA29YIg (deposited on Jun. 19, 2000 with the American Type Culture Collection (ATCC), 10801 University Blvd., Manassas, Va. 20110-2209 and accorded ATCC accession number PTA-2104), were generated by repeating the mutagenesis procedure described above using L104EIg as a template. This method was used to generate numerous double-site mutants nucleotide sequences such as those encoding CTLA4 molecules L104EA29YIg (as included in the sequence shown in FIG. 19), L104EA29LIg (as included in the sequence shown in FIG. 20), L104EA29TIg (as included in the sequence shown in FIG. 21), and L104EA29WIg (as included in the sequence shown in FIG. 22). Triple-site mutants, such as those encoding L104EA29YS25KIg, L104EA29YS25NIg and L104EA29YS25RIg, were also generated The soluble CTLA4 molecules were expressed from the nucleotide sequences and used in the phase II clinical studies described in Example 3, infra.

As those skilled-in-the-art will appreciate, replication of nucleic acid sequences, especially by PCR amplification, easily introduces base changes into DNA strands. However, nucleotide changes do not necessarily translate into amino acid changes as some codons redundantly encode the same amino acid. Any changes of nucleotide from the original or wildtype sequence, silent (i.e. causing no change in the translated amino acid) or otherwise, while not explicitly described herein, are encompassed within the scope of the invention.

EXAMPLE 2

The following example provides a description of the screening methods used to identify the single- and double-site mutant CTLA polypeptides, expressed from the constructs described in Example 1, that exhibited a higher binding avidity for B7 molecules, compared to non-mutated CTLA4Ig molecules.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did augment the inhibition, indicating that CTLA4Ig was not as effective at blocking CD86 interactions. These data support earlier findings by Linsley et al. (*Immunity*, (1994), 1:793-801) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild type CTLA4 should be better able to block the priming of antigen specific activated cells than CTLA4Ig.

To this end, the soluble CTLA4 mutant molecules described in Example 1 above were screened using a novel screening procedure to identify several mutations in the extracellular domain of CTLA4 that improve binding avidity for CD80 and CD86. This screening strategy provided an effective method to directly identify mutants with apparently slower "off" rates without the need for protein purification or quantitation since "off" rate determination is concentration independent (O'Shannessy et al., (1993) *Anal. Biochem.*, 212:457-468).

COS cells were transfected with individual miniprep purified plasmid DNA and propagated for several days. Three day conditioned culture media was applied to BIAcore biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J., et al., 1997 *Anal. Biochem.* 212:457-468). All experiments were run on BIAcore™ or BIAcore™ 2000 biosensors at 25° C. Ligands were immobilized on research grade NCM5 sensor chips (Pharmacia) using standard N-ethyl-N'-(dimethylaminopropyl) carbodiimidN-hydroxysuccinimide coupling (Johnsson, B., et al. (1991) *Anal. Biochem.* 198: 268-277; Khilko, S. N., et al. (1993) *J. Biol. Chem* 268:5425-15434).

Screening Method

COS cells grown in 24 well tissue culture plates were transiently transfected with mutant CTLA4Ig. Culture media containing secreted soluble mutant CTLA4Ig was collected 3 days later.

Conditioned COS cell culture media was allowed to flow over BIAcore biosensor chips derivitized with CD86Ig or CD80Ig (as described in Greene et al., 1996 *J. Biol. Chem.* 271:26762-26771), and mutant molecules were identified with off-rates slower than that observed for wild type CTLA4Ig. The DNAs corresponding to selected media samples were sequenced and more DNA prepared to perform larger scale COS cell transient transfection, from which CTLA4Ig mutant protein was prepared following protein A purification of culture media.

BIAcore analysis conditions and equilibrium binding data analysis were performed as described in J. Greene et al. 1996 *J. Biol. Chem.* 271:26762-26771 and in U.S. patent application Ser. Nos. 09/579,927, and 60/214,065 which are herein incorporated by reference.

BIAcore Data Analysis

Senosorgram baselines were normalized to zero response units (RU) prior to analysis. Samples were run over mock-derivatized flow cells to determine background RU values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple langmuir system, $A+B \leftrightarrows AB$), and equilibrium association constants ($K_d=[A]\cdot[B]\setminus[AB]$) were calculated from the equation $R=R_{max}\cdot C/(K_d+C)$. Subsequently, data were fit to the simplest two-site model of ligand binding (i.e., to a receptor having two non-interacting independent binding sites as described by the equation $R=R_{max1} \cdot C \backslash (K_{d1}+C)+R_{max2} \cdot C \backslash (K_{d2}+C)$.

The goodness-of-fits of these two models were analyzed visually by comparison with experimental data and statistically by an F test of the sums-of-squares. The simpler one-site model was chosen as the best fit, unless the two-site model fit significantly better (p<0.1).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t_0)})$, where $R_t$ is a response at a given time, t; $R_{eq}$ is the steady-state response; $t_0$ is the time at the start of the injection; and $k_s=dR/dt=k_{on} \cdot C k_{off}$, where C is a concentration of analyte, calculated in terms of monomeric binding sites. For two-site interactions $k_{on}$ values were calculated according to the equation $R_t=R_{eq1}(1-\exp^{-ks1(t-t_0)})+R_{eq2}(1-\exp^{ks2(t-t_0)})$. For each model, the values of $k_{on}$ were determined from the calculated slope (to about 70% maximal association) of plots of $k_s$ versus C.

Dissociation data were analyzed according to one site (AB=A+B) or two site (AiBj=Ai+Bj) models, and rate constants ($k_{off}$) were calculated from best fit curves. The binding site model was used except when the residuals were greater than machine background (2-10RU, according to machine), in which case the two-binding site model was employed. Half-times of receptor occupancy were calculated using the relationship $t_{1/2}=0.693/k_{off}$.

Flow Cytometry:

Murine mAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80-positive and/or CD86-positive CHO cells were removed from their culture vessels by incubation in phosphate-buffered saline (PBS) containing 10 mM EDTA. CHO cells (1-10×10$^5$) were first incubated with mAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

SDS-PAGE and Size Exclusion Chromatography

SDS-PAGE was performed on Tris/glycine 4-20% acrylamide gels (Novex, San Diego, Calif.). Analytical gels were stained with Coomassie Blue, and images of wet gels were obtained by digital scanning. CTLA4Ig (25 µg) and L104EA29YIg (25 µg) were analyzed by size exclusion chromatography using a TSK-GEL G300 SW$_{XL}$ column (7.8×300 mm, Tosohaas, Montgomeryville, Pa.) equilibrated in phosphate buffered saline containing 0.02% NAN$_3$ at a flow rate of 1.0 ml/min.

CTLA4X$_{C120S}$ and L104EA29YX$_{C120S}$

Single chain CTLA4X$_{C120S}$ was prepared as previously described (Linsley et al., (1995) *J. Biol. Chem.*, 270:15417-15424). Briefly, an oncostatin M CTLA4 (OMCTLA4) expression plasmid was used as a template, the forward primer, GAGGTGATAAAGCTTCACCAATGGGTGTACTGCTCACACAG (SEQ ID NO: 4) was chosen to match sequences in the vector; and the reverse primer, GTGGTGTATTGGTCTAGATCAATCAGAATCTGGGCACGGTTC (SEQ ID NO: 5) corresponded to the last seven amino acids (i.e. amino acids 118-124) in the extracellular domain of CTLA4, and contained a restriction enzyme site, and a stop codon (TGA). The reverse primer specified a C120S (cysteine to serine at position 120) mutation. In particular, the nucleotide sequence GCA (nucleotides 34-36) of the reverse primer shown above is replaced with one of the following nucleotide sequences: AGA, GGA, TGA, CGA, ACT, or GCT. As persons skilled in the art will understand, the nucleotide sequence GCA is a reversed complementary sequence of the codon TGC for cysteine. Similarly, the nucleotide sequences AGA, GGA, TGA, CGA, ACT, or GCT are the reversed complementary sequences of the codons for serine. Polymerase chain reaction products were digested with HindIII/XbaI and directionally subcloned into the expression vector πLN (Bristol-Myers Squibb Company, Princeton, N.J.). L104EA29YX$_{C120S}$ was prepared in an identical manner. Each construct was verified by DNA sequencing.

Identification and Biochemical Characterization of High Avidity Mutants

Figure 25A:
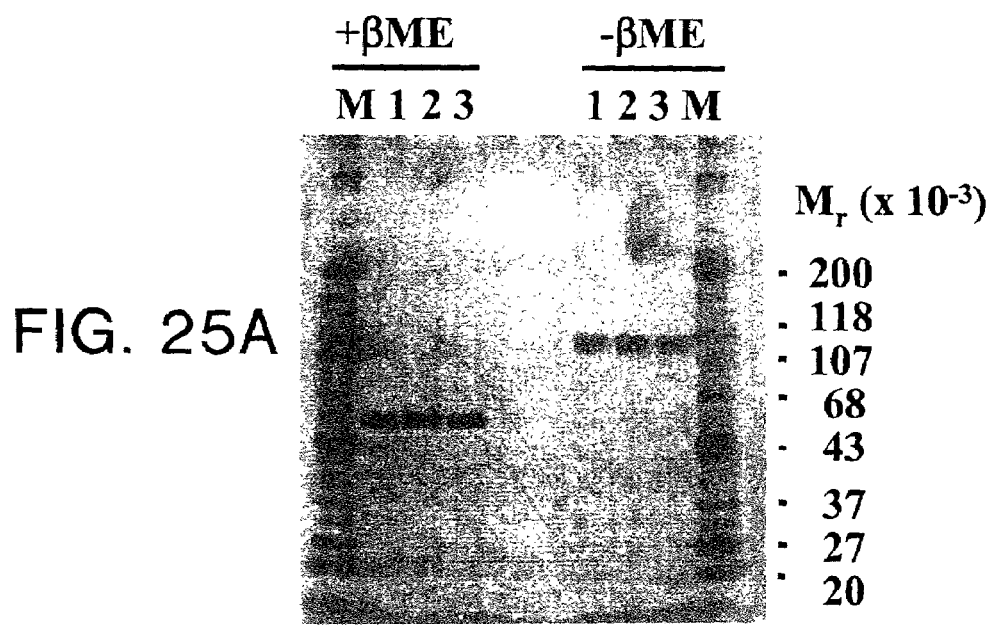
FIG. 25: SDS gel (FIG. 25A) for CTLA4Ig (lane 1), L104EIg (lane 2), and L104EA29YIg (lane 3A); and size exclusion chromatographs of CTLA4Ig (FIG. 25B) and L104EA29YIg (FIG. 25C).
Figure 25B:
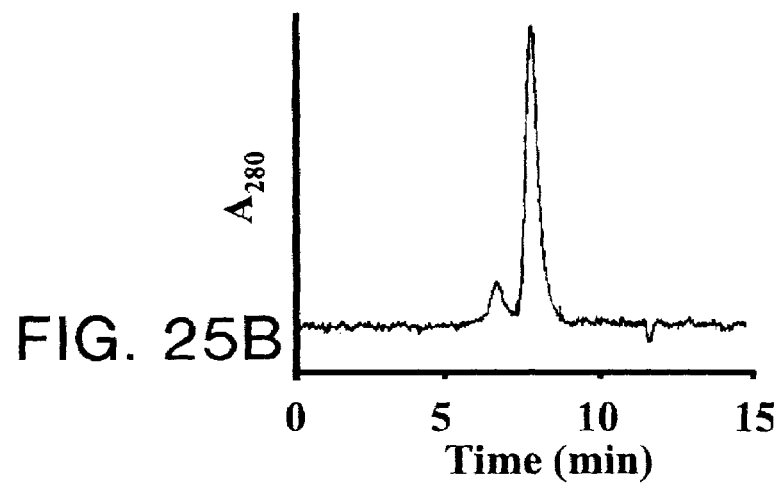
Figure 25C:
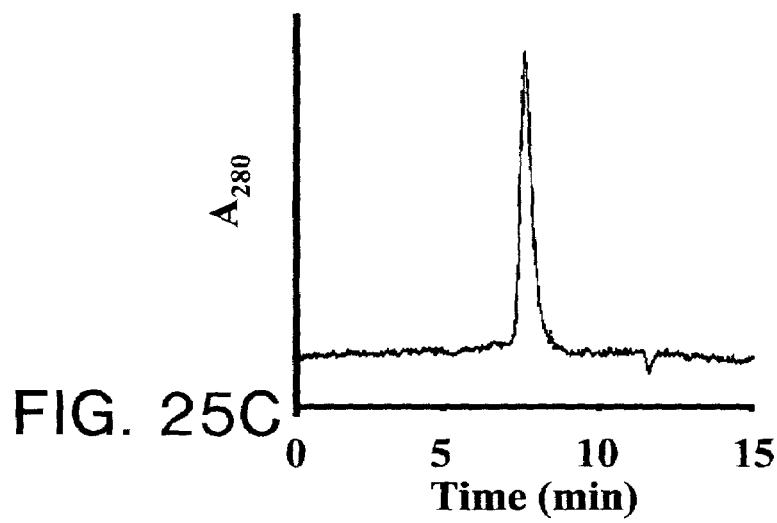

Twenty four amino acids were chosen for mutagenesis and the resulting ~2300 mutant proteins assayed for CD86Ig binding by surface plasmon resonance (SPR; as described, supra). The predominant effects of mutagenesis at each site are summarized in Table II, infra. Random mutagenesis of some amino acids in the CDR-1 region (S25-R33) apparently did not alter ligand binding. Mutagenesis of E31 and R33 and residues M97-Y102 apparently resulted in reduced ligand binding. Mutagenesis of residues, S25, A29, and T30, K93, L96, Y103, L104, and G105, resulted in proteins with slow "on" and/or slow "off" rates. These results confirm previous findings that residues in the CDR-1 (S25-R33) region, and residues in or near M97-Y102 influence ligand binding (Peach et al., (1994) *J. Exp. Med.*, 180:2049-2058).

Mutagenesis of sites S25, T30, K93, L96, Y103, and G105 resulted in the identification of some mutant proteins that had slower "off" rates from CD86Ig. However, in these instances, the slow "off" rate was compromised by a slow "on" rate that resulted in mutant proteins with an overall avidity for CD86Ig that was apparently similar to that seen with wild type CTLA4Ig. In addition, mutagenesis of K93 resulted in significant aggregation that may have been responsible for the kinetic changes observed.

Random mutagenesis of L104 followed by COS cell transfection and screening by SPR of culture media samples over immobilized CD86Ig yielded six media samples containing mutant proteins with approximately 2-fold slower "off" rates than wild type CTLA4Ig. When the corresponding cDNA of these mutants were sequenced, each was found to encode a leucine to glutamic acid mutation (L104E). Apparently, substitution of leucine 104 to aspartic acid (L104D) did not affect CD86Ig binding.

Mutagenesis was then repeated at each site listed in Table II, this time using L104E as the PCR template instead of wild type CTLA4Ig, as described above. SPR analysis, again using immobilized CD86Ig, identified six culture media samples from mutagenesis of alanine 29 with proteins having approximately 4-fold slower "off" rates than wild type CTLA4Ig. The two slowest were tyrosine substitutions (L104EA29Y), two were leucine (L104EA29L), one was tryptophan (L104EA29W), and one was threonine (L104EA29T). Apparently, no slow "off" rate mutants were identified when alanine 29 was randomly mutated, alone, in wild type CTLA4Ig.

The relative molecular mass and state of aggregation of purified L104E and L104EA29YIg was assessed by SDS-PAGE and size exclusion chromatography. L104EA29YIg (~1 μg; lane 3) and L104EIg (~1 μg; lane 2) apparently had the same electrophoretic mobility as CTLA4Ig (~1 µg; lane 1) under reducing (~50 kDa; +βME; plus 2-mercaptoethanol) and non-reducing (~100 kDa; −βME) conditions (FIG. 25A). Size exclusion chromatography demonstrated that L104EA29YIg (FIG. 25C) apparently had the same mobility as dimeric CTLA4Ig (FIG. 25B). The major peaks represent protein dimer while the faster eluting minor peak in FIG. 25B represents higher molecular weight aggregates. Approximately 5.0% of CTLA4Ig was present as higher molecular weight aggregates but there was no evidence of aggregation of L104EA29YIg or L104EIg. Therefore, the stronger binding to CD86Ig seen with L104EIg and L104EA29YIg could not be attributed to aggregation induced by mutagenesis.

Equilibrium and Kinetic Binding Analysis

Equilibrium and kinetic binding analysis was performed on protein A purified CTLA4Ig, L104EIg, and L104EA29YIg using surface plasmon resonance (SPR). The results are shown in Table I, infra. Observed equilibrium dissociation constants ($K_d$; Table I) were calculated from binding curves generated over a range of concentrations (5.0-200 nM). L104EA29YIg binds more strongly to CD86Ig than does L104EIg or CTLA4Ig. The lower $K_d$ of L104EA29YIg (3.21 nM) than L104EIg (6.06 nM) or CTLA4Ig (13.9 nM) indicates higher binding avidity of L104EA29YIg to CD86Ig. The lower $K_d$ of L104EA29YIg (3.66 nM) than L104EIg (4.47 nM) or CTLA4Ig (6.51 nM) indicates higher binding avidity of L104EA29YIg to CD80Ig.

Kinetic binding analysis revealed that the comparative "on" rates for CTLA4Ig, L104EIg, and L104EA29YIg binding to CD80 were similar, as were the "on" rates for CD86Ig (Table I). However, "off" rates for these molecules were not equivalent (Table I). Compared to CTLA4Ig, L104EA29YIg had approximately 2-fold slower "off" rate from CD80Ig, and approximately 4-fold slower "off" rate from CD86Ig. L104E had "off" rates intermediate between L104EA29YIg and CTLA4Ig. Since the introduction of these mutations did not significantly affect "on" rates, the increase in avidity for CD80Ig and CD86Ig observed with L104EA29YIg was likely primarily due to a decrease in "off" rates.

To determine whether the increase in avidity of L104EA29YIg for CD86Ig and CD80Ig was due to the mutations affecting the way each monomer associated as a dimer, or whether there were avidity enhancing structural changes introduced into each monomer, single chain constructs of CTLA4 and L104EA29Y extracellular domains were prepared following mutagenesis of cysteine 120 to serine as described supra, and by Linsley et al., (1995) *J. Biol. Chem.*, 270:15417-15424 (84). The purified proteins CTLA4$X_{C120S}$ and L104EA29YX$_{C120S}$ were shown to be monomeric by gel permeation chromatography (Linsley et al., (1995), supra), before their ligand binding properties were analyzed by SPR. Results showed that binding affinity of both monomeric proteins for CD86Ig was approximately 35-80-fold less than that seen for their respective dimers (Table I). This supports previously published data establishing that dimerization of CTLA4 was required for high avidity ligand binding (Greene et al., (1996) *J. Biol. Chem.*, 271:26762-26771).

L104EA29YX$_{c120S}$ bound with approximately 2-fold higher affinity than CTLA4X$_{C120S}$ to both CD80Ig and CD86Ig. The increased affinity was due to approximately 3-fold slower rate of dissociation from both ligands. Therefore, stronger ligand binding by L104EA29Y was most likely due to avidity enhancing structural changes that had been introduced into each monomeric chain rather than alterations in which the molecule dimerized.

Location and Structural Analysis of Avidity Enhancing Mutations

Figure 26:
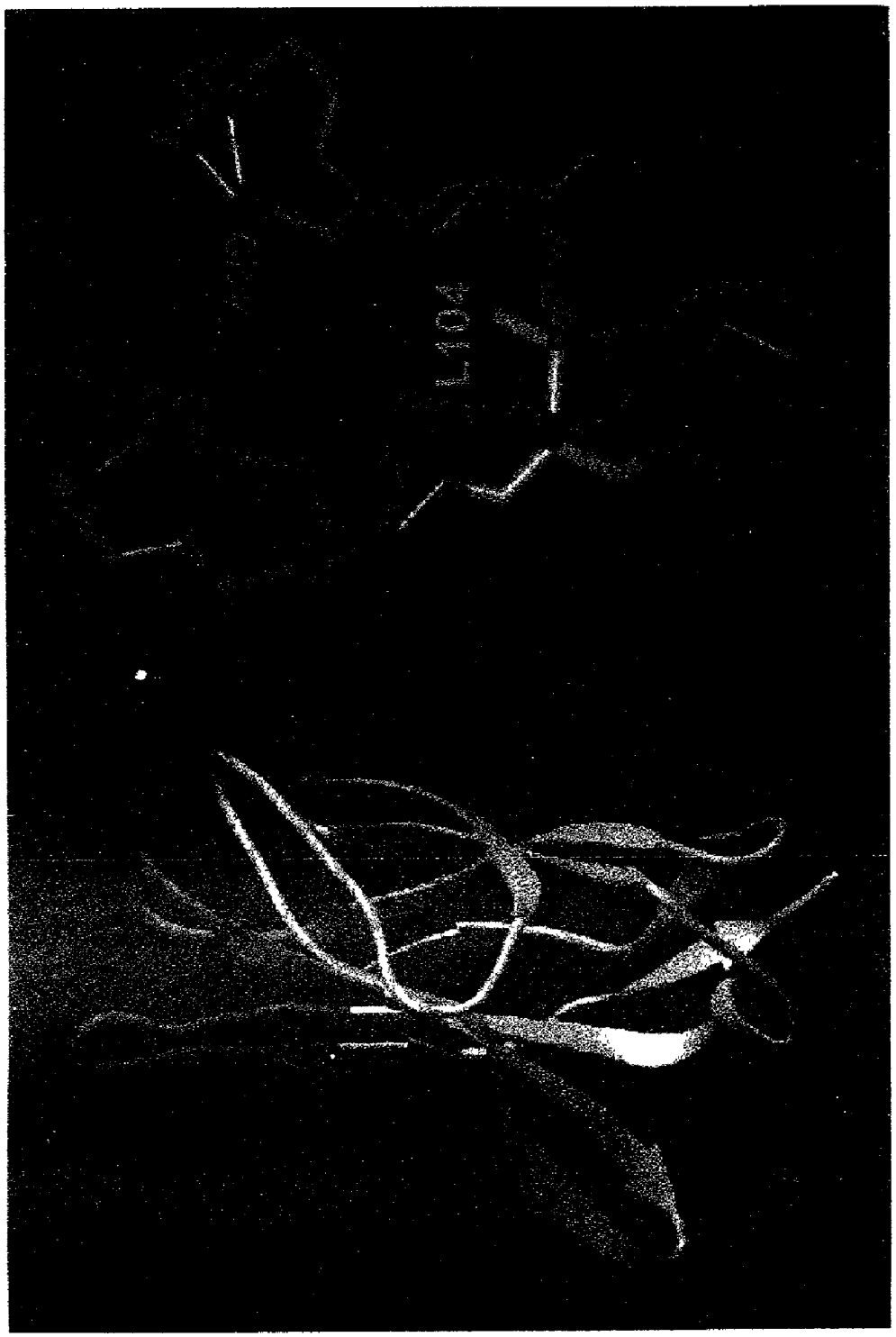
FIG. 26 (left and right depictions): A ribbon diagram of the CTLA4 extracellular Ig V-like fold generated from the solution structure determined by NMR spectroscopy.

The solution structure of the extracellular IgV-like domain of CTLA4 has recently been determined by NMR spectroscopy (Metzler et al., (1997) *Nature Struct. Biol.*, 4:527-531). This allowed accurate location of leucine 104 and alanine 29 in the three dimensional fold (FIG. 26 left and right depictions). Leucine 104 is situated near the highly conserved MYPPPY amino acid sequence (SEQ ID NO:20). Alanine 29 is situated near the C-terminal end of the CDR-1 (S25-R33) region, which is spatially adjacent to the MYPPPY region. While there is significant interaction between residues at the base of these two regions, there is apparently no direct interaction between L104 and A29 although they both comprise part of a contiguous hydrophobic core in the protein. The structural consequences of the two avidity enhancing mutants were assessed by modeling. The A29Y mutation can be easily accommodated in the cleft between the CDR-1 (S25-R33) region and the MYPPPY region, and may serve to stabilize the conformation of the MYPPPY region. In wild type CTLA4, L104 forms extensive hydrophobic interactions with L96 and V94 near the MYPPPY region. It is highly unlikely that the glutamic acid mutation adopts a conformation similar to that of L104 for two reasons. First, there is insufficient space to accommodate the longer glutamic acid side chain in the structure without significant perturbation to the CDR-1 (S25-R33 region). Second, the energetic costs of burying the negative charge of the glutamic acid side chain in the hydrophobic.

Binding of High Avidity Mutants to CHO Cells Expressing CD80 or CD86

FACS analysis (FIG. 27) of CTLA4Ig and mutant molecules binding to stably transfected CD80+ and CD86+CHO cells was performed as described herein. CD80-positive and CD86-positive CHO cells were incubated with increasing concentrations of CTLA4Ig, L104EA29YIg, or L104EIg, and then washed. Bound immunoglobulin fusion protein was detected using fluorescein isothiocyanate-conjugated goat anti-human immunoglobulin.

As shown in FIG. 27, CD80-positive or CD86-positive CHO cells ($1.5 \times 10^5$) were incubated with the indicated concentrations of CTLA4Ig (closed squares), L104EA29YIg (circles), or L104EIg (triangles) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data were corrected for background fluorescence measured on cells incubated with second step reagent only (MFI=7). Control L6 mAb (80 µg/ml) gave MFI<30. These results are representative of four independent experiments.

Figure 27A:
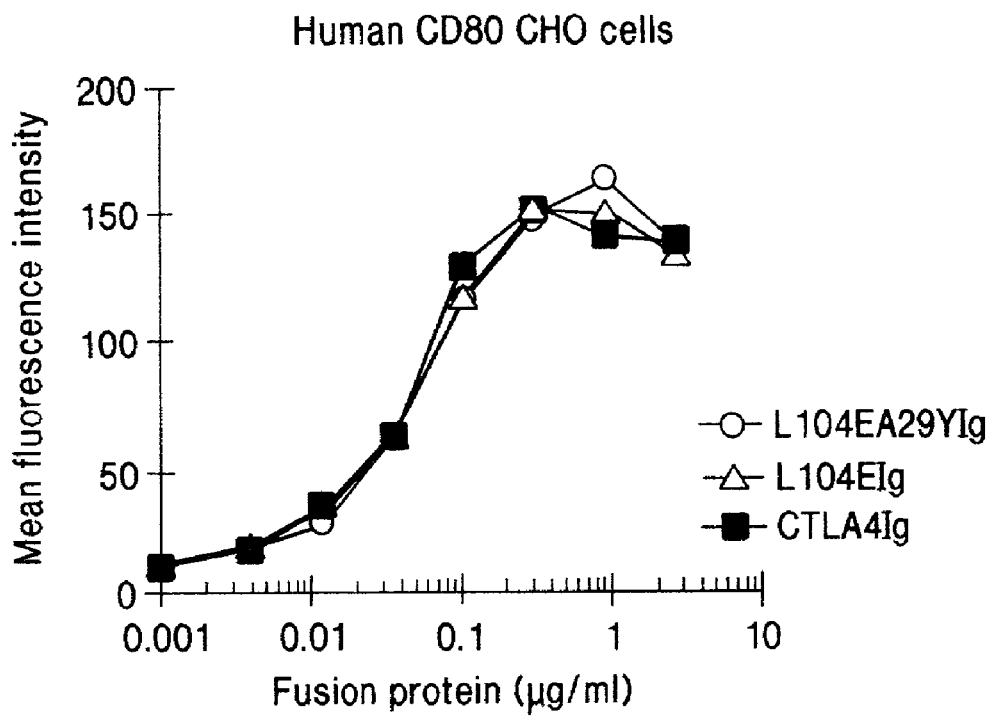
FIGS. 27A & 27B: FACS assays showing binding of L104EA29YIg, L104EIg, and CTLA4Ig to human CD80- or CD86-transfected CHO cells as described in Example 2, infra.
Figure 27B:
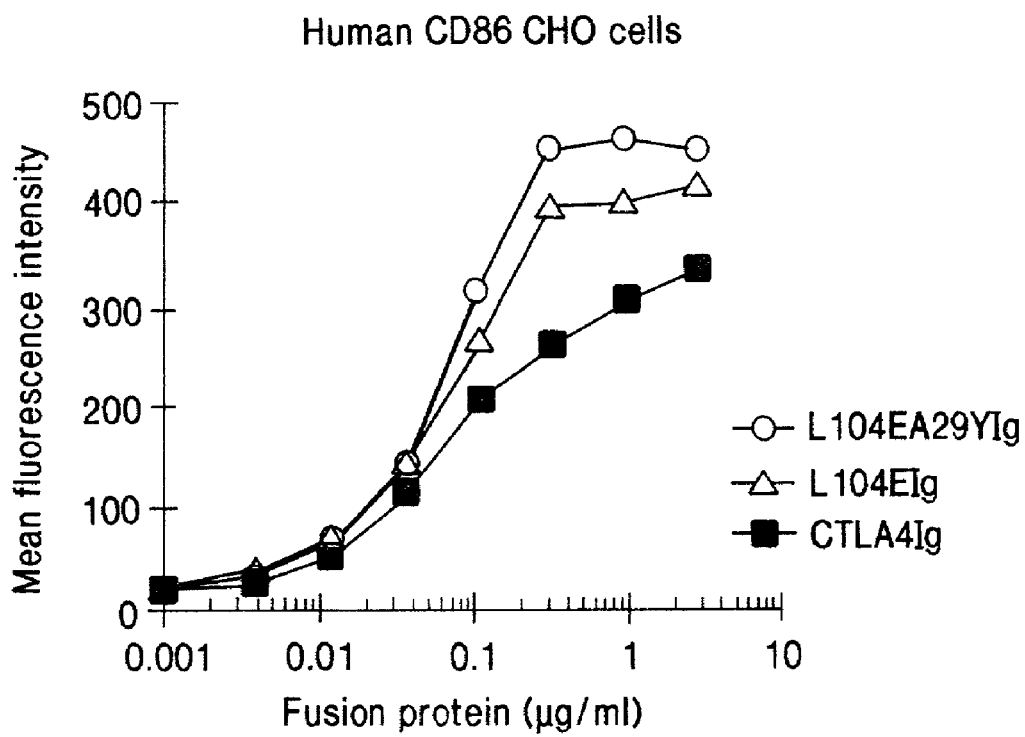

Binding of L104EA29YIg, L104EIg, and CTLA4Ig to human CD80-transfected CHO cells is approximately equivalent (FIG. 27A). L104EA29YIg and L104EIg bind more strongly to CHO cells stably transfected with human CD86 than does CTLA4Ig (FIG. 27B).

Figure 28A:
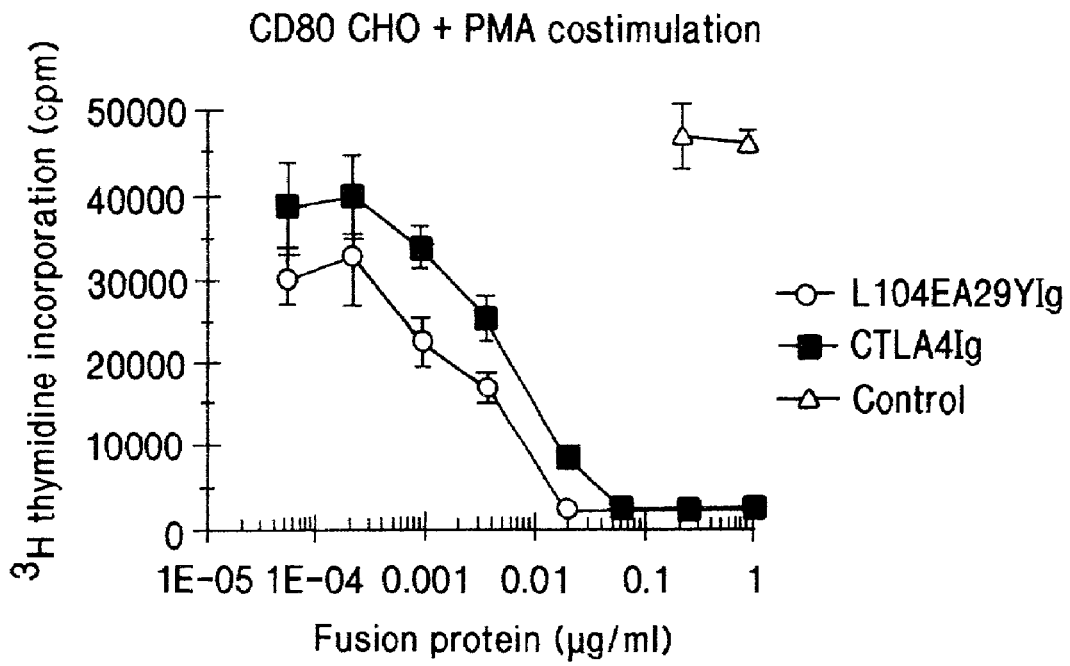
FIGS. 28A & 28B: Graphs showing inhibition of proliferation of CD80-positive and CD86-positive CHO cells as described in Example 2, infra.
Figure 28B:
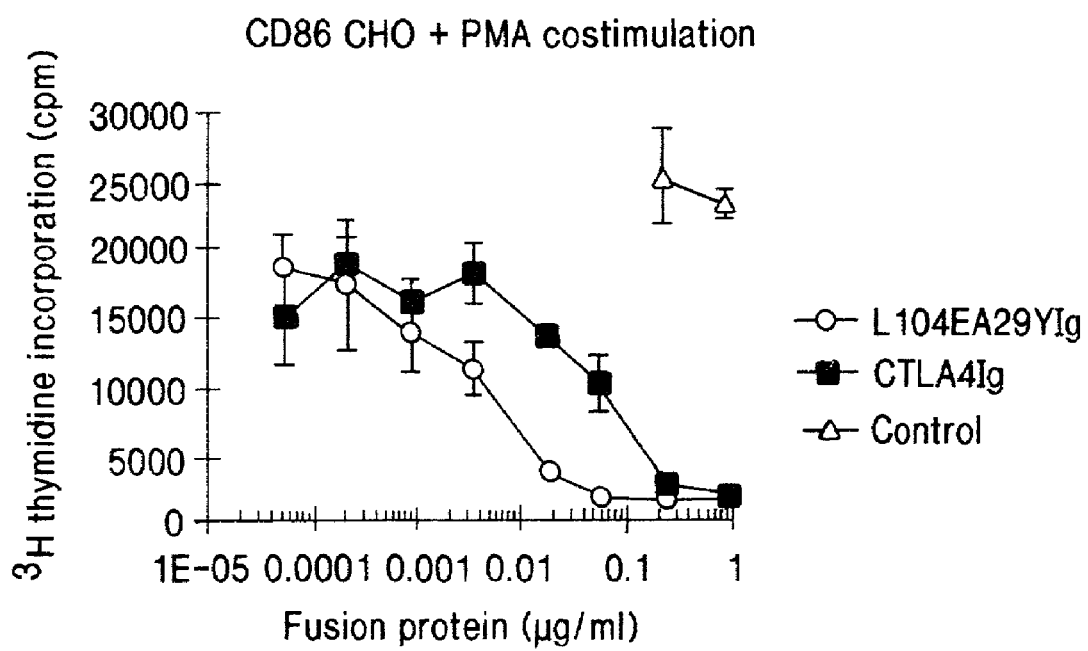

Functional Assays:

Human CD4-positive T cells were isolated by immunomagnetic negative selection (Linsley et al., (1992) *J. Exp. Med.* 176:1595-1604). Isolated CD4-positive T cells were stimulated with phorbal myristate acetate (PMA) plus CD80-positive or CD86-positive CHO cells in the presence of titrating concentrations of inhibitor. CD4-positive T cells ($8-10 \times 10^4$/well) were cultured in the presence of 1 nM PMA with or without irradiated CHO cell stimulators. Proliferative responses were measured by the addition of 1 μCi/well of [3H]thymidine during the final 7 hours of a 72 hour culture. Inhibition of PMA plus CD80-positive CHO, or CD86-positive CHO, stimulated T cells by L104EA29YIg and CTLA4Ig was performed. The results are shown in FIG. 28. L104EA29YIg inhibits proliferation of CD80-positive PMA treated CHO cells more than CTLA4Ig (FIG. 28A). L104EA29YIg is also more effective than CTLA4Ig at inhibiting proliferation of CD86-positive PMA treated CHO cells (FIG. 28B). Therefore, L104EA29YIg is a more potent inhibitor of both CD80- and CD86-mediated costimulation of T cells.

FIG. 29 shows inhibition by L104EA29YIg and CTLA4Ig of allostimulated human T cells prepared above, and further allostimulated with a human B lymphoblastoid cell line (LCL) called PM that expressed CD80 and CD86 (T cells at $3.0 \times 10^4$/well and PM at $8.0 \times 10^3$/well). Primary allostimulation occurred for 6 days, then the cells were pulsed with $^3$H-thymidine for 7 hours, before incorporation of radiolabel was determined.

Figure 29A:
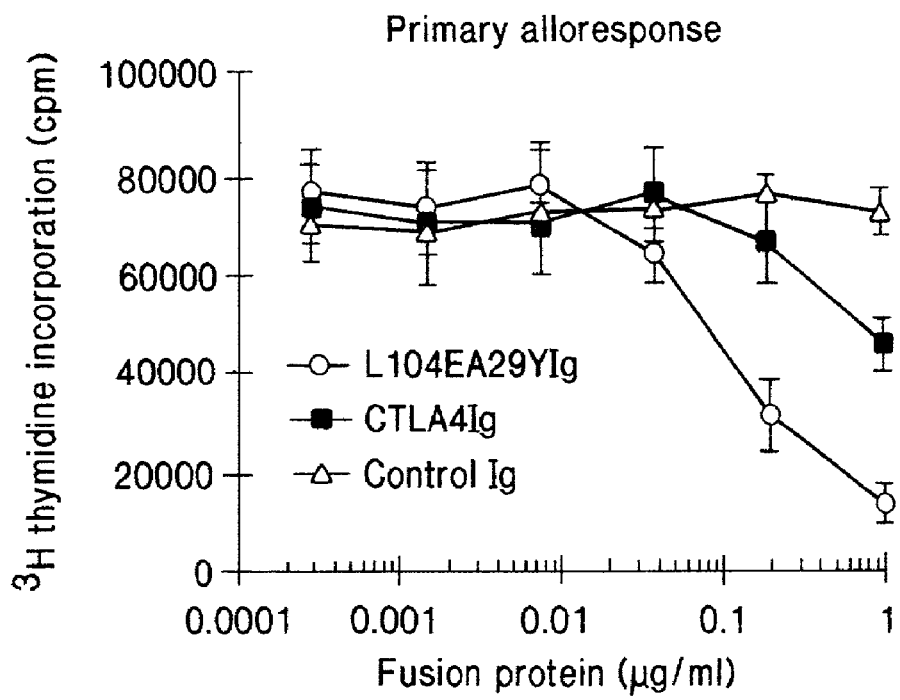
FIGS. 29A & 29B: Graphs showing that L104EA29YIg is more effective than CTLA4Ig at inhibiting proliferation of primary and secondary allostimulated T cells as described in Example 2, infra.
Figure 29B:
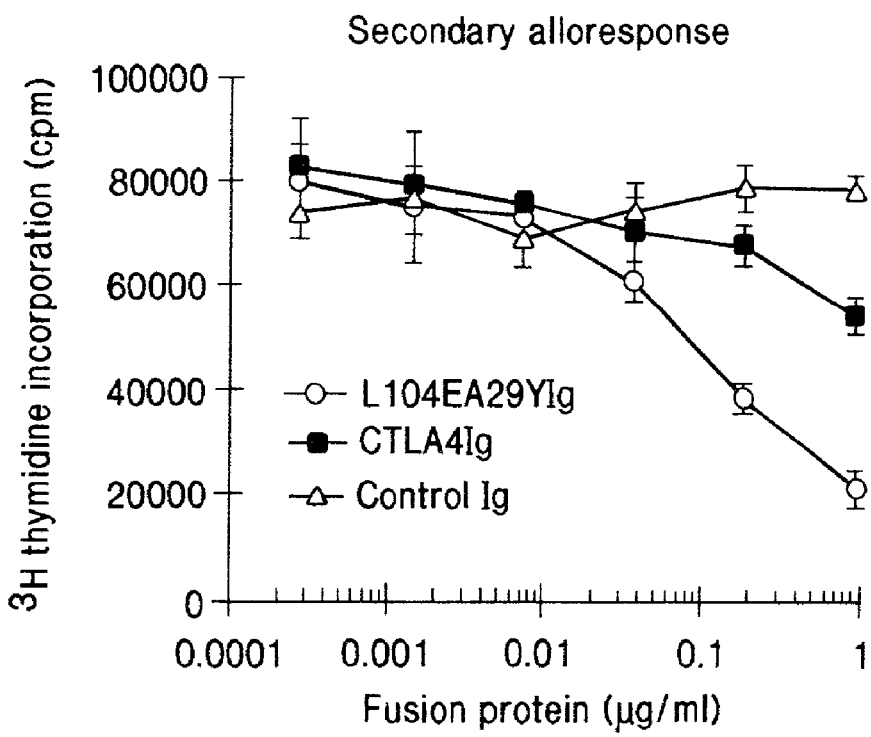

Secondary allostimulation was performed as follows. Seven day primary allostimulated T cells were harvested over lymphocyte separation medium (LSM) (ICN, Aurora, Ohio) and rested for 24 hours. T cells were then restimulated (secondary), in the presence of titrating amounts of CTLA4Ig or L104EA29YIg, by adding PM in the same ratio as above. Stimulation occurred for 3 days, then the cells were pulsed with radiolabel and harvested as above. The effect of L104EA29YIg on primary allostimulated T cells is shown in FIG. 29A. The effect of L104EA29YIg on secondary allostimulated T cells is shown in FIG. 29B. L104EA29YIg inhibits both primary and secondary T cell proliferative responses better than CTLA4Ig.

Figure 30A:
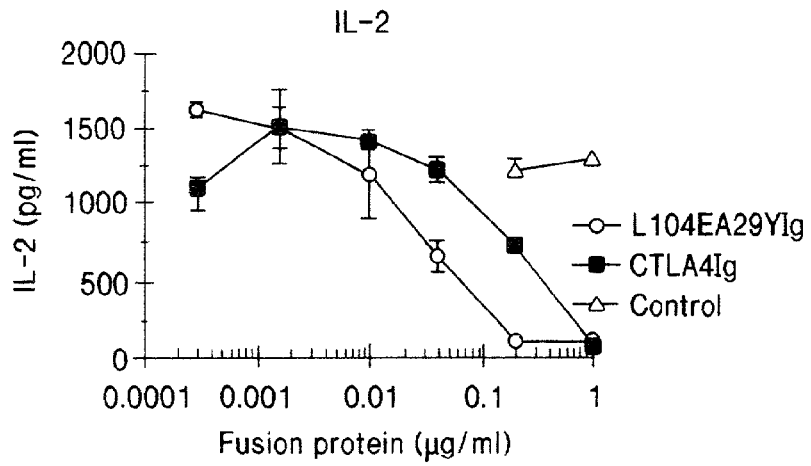
FIGS. 30A-C: Graphs illustrating that L104EA29YIg is more effective than CTLA4Ig at inhibiting IL-2 (FIG. 30A), IL-4 (FIG. 30B), and gamma (γ)-interferon (FIG. 30C) cytokine production of allostimulated human T cells as described in Example 2, infra.
Figure 30B:
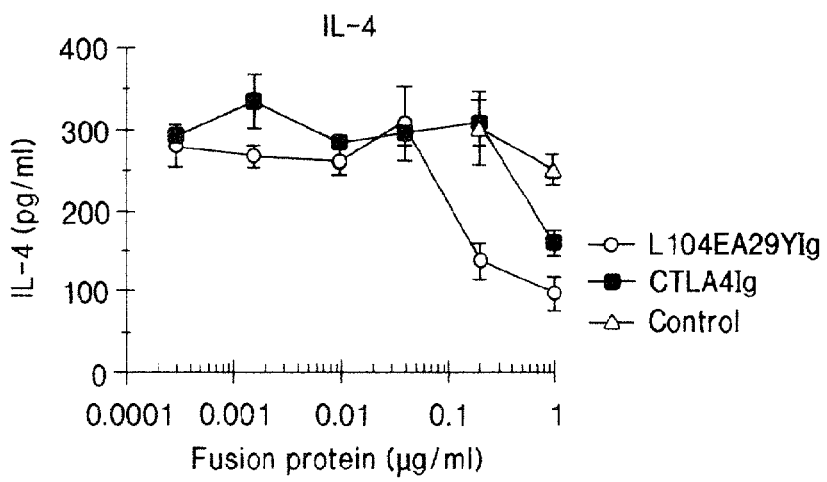
Figure 30C:
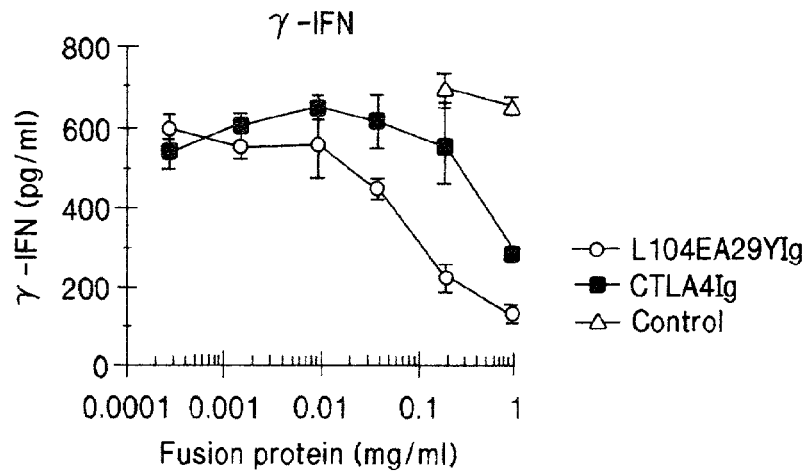

To measure cytokine production (FIG. 30), duplicate secondary allostimulation plates were set up. After 3 days, culture media was assayed using ELISA kits (Biosource, Camarillo, Calif.) using conditions recommended by the manufacturer. L104EA29YIg was found to be more potent than CTLA4Ig at blocking T cell IL-2, IL-4, and γ-IFN cytokine production following a secondary allogeneic stimulus (FIGS. 30A-C).

Figure 31:
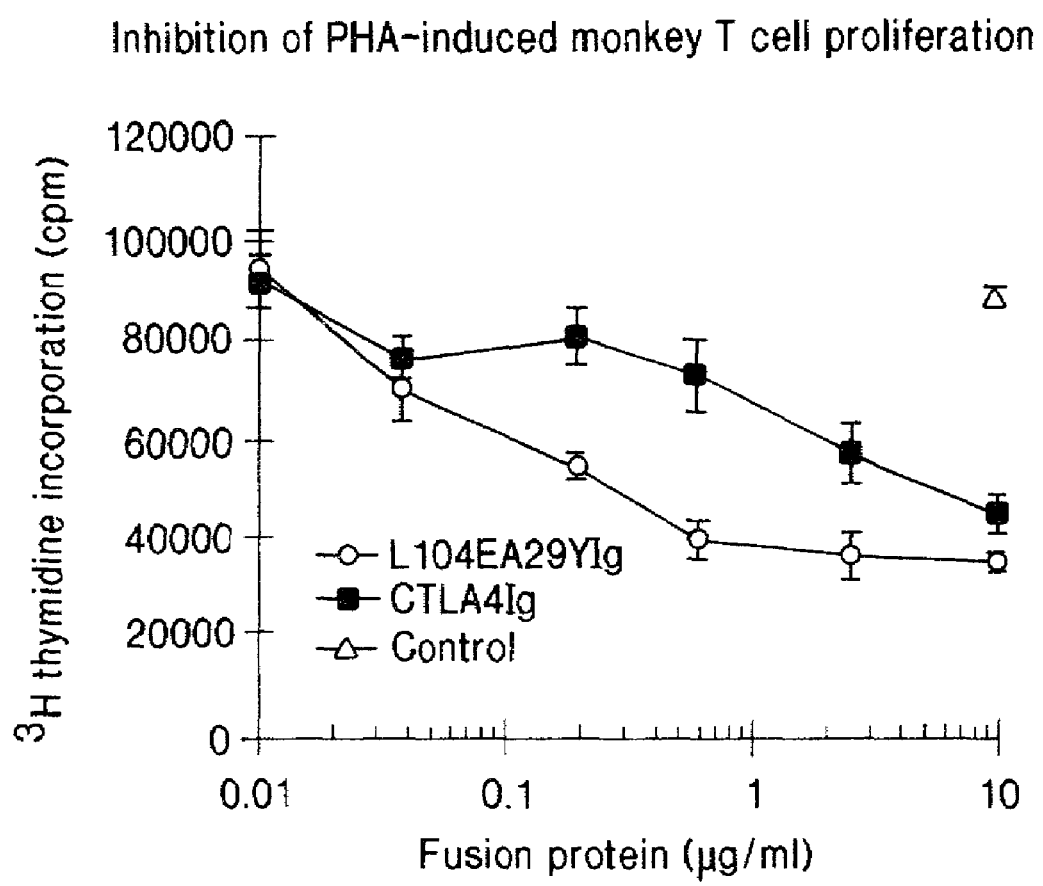
FIG. 31: A graph demonstrating that L104EA29YIg is more effective than CTLA4Ig at inhibiting proliferation of phytohemaglutinin-(PHA) stimulated monkey T cells as described in Example 2, infra.
Figure 32:
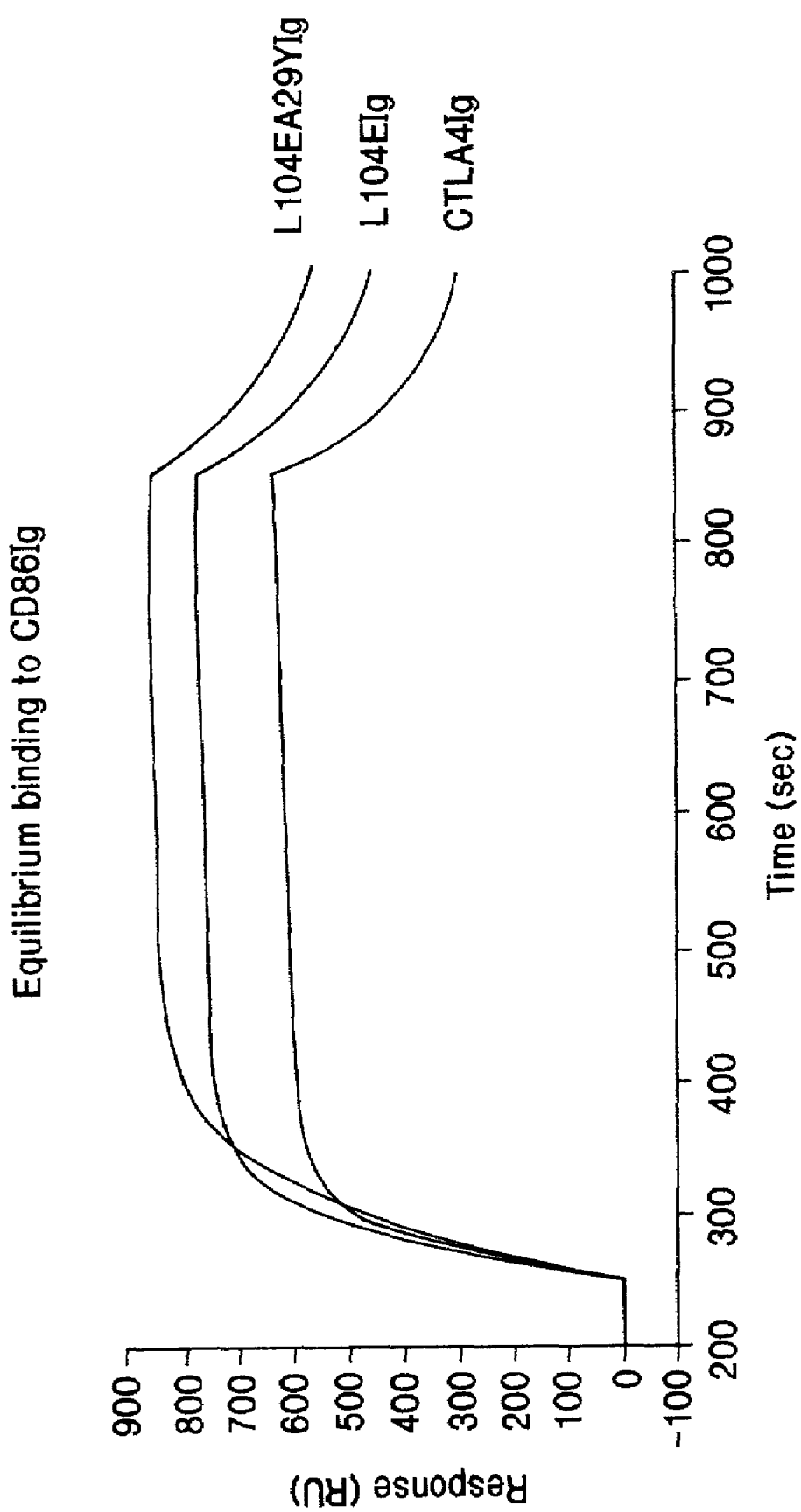
FIG. 32: A graph showing the equilibrium binding analysis of L104EA29YIg, L104EIg, and wild-type CTLA4Ig to CD86Ig.

The effects of L104EA29YIg and CTLA4Ig on monkey mixed lymphocyte response (MLR) are shown in FIG. 31. Peripheral blood mononuclear cells (PBMC'S; $3.5 \times 10^4$ cells/well from each monkey) from 2 monkeys were purified over lymphocyte separation medium (LSM) and mixed with 2 μg/ml phytohemaglutinin (PHA). The cells were stimulated 3 days then pulsed with radiolabel 16 hours before harvesting. L104EA29YIg inhibited monkey T cell proliferation better than CTLA4Ig.

TABLE I

Equilibrium and apparent kinetic constants are given in the following table (values are means ± standard deviation from three different experiments):

| Immobilized Protein | Analyte | $k_{on} (\times 10^5)$ $M^{-1} S^{-1}$ | $k_{off} (\times 10^{-3})$ $S^{-1}$ | $K_d$ nM |
|---|---|---|---|---|
| CD80Ig | CTLA4Ig | 3.44 ± 0.29 | 2.21 ± 0.18 | 6.51 ± 1.08 |
| CD80Ig | L104EIg | 3.02 ± 0.05 | 1.35 ± 0.08 | 4.47 ± 0.36 |
| CD80Ig | L104EA29YIg | 2.96 ± 0.20 | 1.08 ± 0.05 | 3.66 ± 0.41 |
| CD80Ig | CTLA4X$_{C120S}$ | 12.0 ± 1.0 | 230 ± 10 | 195 ± 25 |
| CD80Ig | L104EA29YX$_{C120S}$ | 8.3 ± 0.26 | 71 ± 5 | 85.0 ± 2.5 |
| CD86Ig | CTLA4Ig | 5.95 ± 0.57 | 8.16 ± 0.52 | 13.9 ± 2.27 |
| CD86Ig | L104EIg | 7.03 ± 0.22 | 4.26 ± 0.11 | 6.06 ± 0.05 |
| CD86Ig | L104EA29YIg | 6.42 ± 0.40 | 2.06 ± 0.03 | 3.21 ± 0.23 |

TABLE I-continued

Equilibrium and apparent kinetic constants are given in the following table (values are means ± standard deviation from three different experiments):

| Immobilized Protein | Analyte | $k_{on} (\times 10^5)$ $M^{-1} S^{-1}$ | $k_{off} (\times 10^{-3})$ $S^{-1}$ | $K_d$ nM |
|---|---|---|---|---|
| CD86Ig | CTLA4X$_{C120S}$ | 16.5 ± 0.5 | 840 ± 55 | 511 ± 17 |
| CD86Ig | L104EA29YX$_{C120S}$ | 11.4 ± 1.6 | 300 ± 10 | 267 ± 29 |

TABLE II

The effect on CD86Ig binding by mutagenesis of CTLA4Ig at the sites listed was determined by SPR, described supra. The predominant effect is indicated with a "+" sign.

| | Effects of Mutagenesis | | |
|---|---|---|---|
| Mutagenesis Site | No Apparent Effect | Slow "on" rate/ slow "off rate | Reduced ligand binding |
| S25 | | + | |
| P26 | + | | |
| G27 | + | | |
| K28 | + | | |
| A29 | | + | |
| T30 | | + | |
| E31 | | | + |
| R33 | | | + |
| K93 | | + | |
| L96 | | + | |
| M97 | | | + |
| Y98 | | | + |
| P99 | | | + |
| P100 | | | + |
| P101 | | | + |
| Y102 | | | + |
| Y103 | | + | |
| L104 | | + | |
| G105 | | + | |
| I106 | + | | |
| G107 | + | | |
| Q111 | + | | |
| Y113 | + | | |
| I115 | + | | |

EXAMPLE 3

The following provides a description of phase II clinical studies of human patients administered soluble CTLA4 mutant molecule L104EA29YIg (also known as LEA29Y or LEA) or CTLA4Ig, to relieve at least one symptom associated with rheumatoid arthritis, including reducing: joint swelling, joint tenderness, inflammation, morning stiffness, and pain. The CTLA4Ig molecule used herein begins with methionine at position +1 (or alternatively with alanine at position −1) and ends with lysine at position +357 as shown in FIG. 24. DNA encoding an embodiment of the CTLA4Ig molecule has been deposited as ATCC 68629. The L104EA29YIg molecule used herein begins with methionine at position +1 (or alternatively with alanine at position −1) and ends with lysine at position +357 as shown in FIG. 19. DNA encoding an embodiment of the L104EA29YIg molecule has been deposited as ATCC PTA 2104.

Additionally, the following provides a description of human patients administered L104EA29YIg or CTLA4Ig to relieve at least one biological surrogate marker associated with rheumatoid arthritis, including reducing erythrocyte sedimentation rates, and serum levels of C-reactive protein and/or IL2 receptor.

Patient Cohorts

A total of 214 patients, including 54 males and 160 females, participated in the study (FIGS. 1A, 1B). The patients at baseline had a mean disease duration of 3.4 (±2.0) years and had failed at least one Disease Modifying Antirheumatic Drug (DMARD). Stable Nonsteroidal Anti-inflammatory Drugs (NSAIDS) or steroids ($\leq$10 mg/day) were permitted and concomitant DMARDS were prohibited. The patients were randomized into groups of 25 to 32 patients per treatment group. Thirty-two patients received a placebo, 92 received L104EA29YIg, and 90 received CTLA4Ig. The patients who followed protocol guidelines and did not discontinue before day 57 received a total of 4 intravenous infusions, one infusion each on days 1, 15, 29, and 57. All patients were evaluated on days 1, 15, 29, 43, 57, 71, and 85. The doses administered included 0.5, 2.0, or 10.0 mg/kg of L104EA29YIg (denoted as LEA.5, LEA2 and LEA10, respectively in FIGS. 1A-1E) or of CTLA4Ig (denoted as CTLA.5, CTLA2 and CTLA10, respectively in FIGS. 1A-1E).

All subjects were monitored for peri-infusional adverse events and global safety by answering a questionnaire listing potential adverse events. The patients were questioned about potential adverse events that may have occurred within twenty-four hours post-infusion. In addition, the patients were encouraged to spontaneously report any adverse events that they experienced. The physicians routinely monitored laboratory samples from the patients for abnormalities in blood chemistry and hematology e.g. assessed the levels of inflammatory response mediators such as cytokines (TNF, IL-6), tryptase and complement. The primary endpoint was the proportion of subjects meeting the ACR 20 criteria on day 85.

Storage of Test Material

The CTLA4Ig and L104EA29YIg were supplied in single-use glass vials containing 200 mg/vial of CTLA4Ig or 100 mg/vial of L104EA29YIg, respectively. Prior to infusion, the CTLA4Ig and L104EA29YIg were diluted to a final concentration of 25 mg/ml with sterile water for injection (SWFI).

Administration Protocol

All infusions were administered intravenously over 1 hour (FIGS. 1 through 17). All subjects received at least one infusion of study medication.

Group 1: 32 patients, CTLA4Ig or L104EA29YIg matching placebo.
Group 2: 26 patients; dosage 0.5 mg/kg of CTLA4Ig.
Group 3: 32 patients; dosage 2.0 mg/kg of CTLA4Ig.
Group 4: 32 patients; dosage 10.0 mg/kg of CTLA4Ig.
Group 5: 32 patients; dosage 0.5 mg/kg of L104EA29YIg.
Group 6: 29 patients; dosage 2.0 mg/kg of L104EA29YIg.
Group 7: 31 patients; dosage 10.0 mg/kg of L104EA29YIg.

Clinical Monitoring

Patients were evaluated for baseline symptoms of disease activity prior to receiving any infusions. These baseline evaluations included: joint swelling, joint tenderness, inflammation, morning stiffness, disease activity evaluated by patient and physician as well as disability evaluated by Health Questionnaire Assessment (HAQ) (reported as a physical function score in FIG. 1C), and pain (FIGS. 1A to 1D). Additionally, the baseline evaluations included erythrocyte sedimentation rates (ESR), and serum levels of C-reactive protein (CRP) and soluble IL-2 receptor (IL-2r) (FIGS. 1C and 1D).

The clinical response studies were based on the criteria established by the American College of Rheumatology (ACR). A subject satisfied the ACR20 criterion if there was a 20 percent improvement in tender and swollen joint counts and 20 percent improvement in three of the five remaining symptoms measured, such as patient and physician global disease changes, pain, disability, and an acute phase reactant (Felson, D. T., et al., 1993 *Arthritis and Rheumatism* 36:729-740; Felson, D. T., et al., 1995 *Arthritis and Rheumatism* 38:1-9).

Biomarkers

Potential biomarkers of disease activity (rheumatoid factor, CRP, ESR, soluble IL-2R, soluble ICAM-1, soluble E-selectin, and MMP-3) were also assessed. Validated enzyme immunoassay (EIA) methods were used to determine the serum concentration of IL-2sRα, sICAM-1, sE-selectin and MMP-3. TNFα and IL-6 were assessed at infusion pre and 2 hours post, if necessary.

IL-2sRα, sICAM-1, and sE-selectin were measured using commercially available colorimetric EIA kits from R&D Systems, Inc. (Minneapolis, Minn.). The lower and upper limits of quantitation were 312-20,000 pg/mL, 40-907 ng/mL and 10-206 ng/mL, respectively. The inter-assay coefficient of variation ranged from 4.48-8.4%, 3.8-5.0% and 5.5-9.0% respectively. According to the kit manufacturer, normal serum values range from 676-2,132 pg/mL, respectively.

MMP-3 was measured using a commercially available calorimetric EIA kit from Amersham Pharmacia Biotech (Piscataway, N.J.). The lower and upper limits of quantitation were 30-7,680 ng/mL. The inter-assay coefficient of variation ranged from 6.3-10.6%. According to the kit manufacturer, normal serum values range from 28-99 ng/mL.

IL-6 and TNFα were measured using commercially available chemiluminescent EIA kits from R&D Systems, Inc. (Minneapolis, Minn.). The lower and upper limits of quantitation were 0.3-3,000 pg/mL and 0.7-7,000 pg/mL, respectively. The inter-assay coefficient of variation ranged from 3.1-5.7% and 6.4-20.7%, respectively. According to the kit manufacturer, normal serum values range from <0.3-12 pg/mL and <0.7-7.5 pg/mL.

Antibody testing

Serum samples were obtained for assessment of drug-specific antibodies prior to dosing on day 1, and approximately on days 15, 29, 57, 85 and 169. Due to high, preexisting titers directed to the immunoglobulin (Ig) portion of the molecule, specific antibody formation against CTLA4Ig and LEA29Y without Ig constant regions was also assessed.

Ninety-six well Immulon II ELISA plates (Dynex, Chantilly, Va.) were coated with CTLA4Ig, CTLA4Ig without the Ig constant regions, LEA29Y, or LEA29Y without the Ig constant regions at 2, 4, 2, or 1 µg/ml in phosphate buffered saline (PBS), respectively, and incubated overnight at 2-8° C. The plates were washed with PBS containing 0.05% Tween 20 and blocked for 1 hour at 37° C. with PBS containing 1% bovine serum albumin (BSA). The plates were then washed and serial dilutions of the test sera or quality control (QC) sera were added to the appropriate wells and incubated for 2 hours at 37° C. Sera was diluted threefold in PBS with 0.25% BSA and 0.05% Tween 20 starting at a 1:10 dilution. Plates were washed and an alkaline-phosphatase-conjugated goat anti-human kappa and lambda (Southern Biotechnology Associates, Inc., Birmingham, Ala.) antibody cocktail was added.

Following a 1-hour incubation at 37° C., the plates were washed and 1 mg/ml para-nitrophenyl phosphate in diethanolamine buffer was added to each well. After 30 minutes at 25° C., the reactions were stopped with 3N NaOH and the absorbance (dual wavelength: 405 nm and 550 nm) was recorded. Results were expressed as endpoint titer (EPT), defined as the reciprocal of the highest dilution that resulted in an absorbance reading fivefold greater than or equal to the mean plate-background absorbance. Plate background was determined as the absorbance measurement recorded in the absence of serum. Values were considered positive for seroconversion if they were at least two serial dilutions (ninefold) or greater relative to predose EPT values. Serum QC samples positive for either CTLA4Ig- or LEA29Y-specific antibodies were generated from immunized monkeys. An aliquot of the appropriate QC sample was assayed during each analytical run. Analytical runs were accepted only when the QC samples were within the assay acceptance criteria.

Results

CTLA4Ig and L104EA29YIg were generally well-tolerated at all dose-levels. Peri-infusional adverse events were similar across all dose groups, with the exception of headaches. Headache response of patients on day 85 increased dose-dependently 23%, 44%, and 53% in CTLA4Ig-treated patients, and 34%, 45%, and 61% in L104EA29YIg-treated patients, at 0.5, 2.0, and 10.0 mg/kg respectively. In contrast, 31% of the patients administered placebos experienced headaches.

The percent of patients that discontinued from the clinical study due to arthritis flares and other adverse events is summarized in FIG. 2. A much higher percentage of patients on placebo discontinued treatment due to arthritis flare. The CTLA4Ig treated patients discontinued treatment less with increasing doses. Very few patients treated with L104EA29YIg discontinued treatment. These results indicate a good inverse dose-dependent response for CTLA4Ig, and a stronger therapeutic response with L104EA29YIg therapy.

Figure 3A:
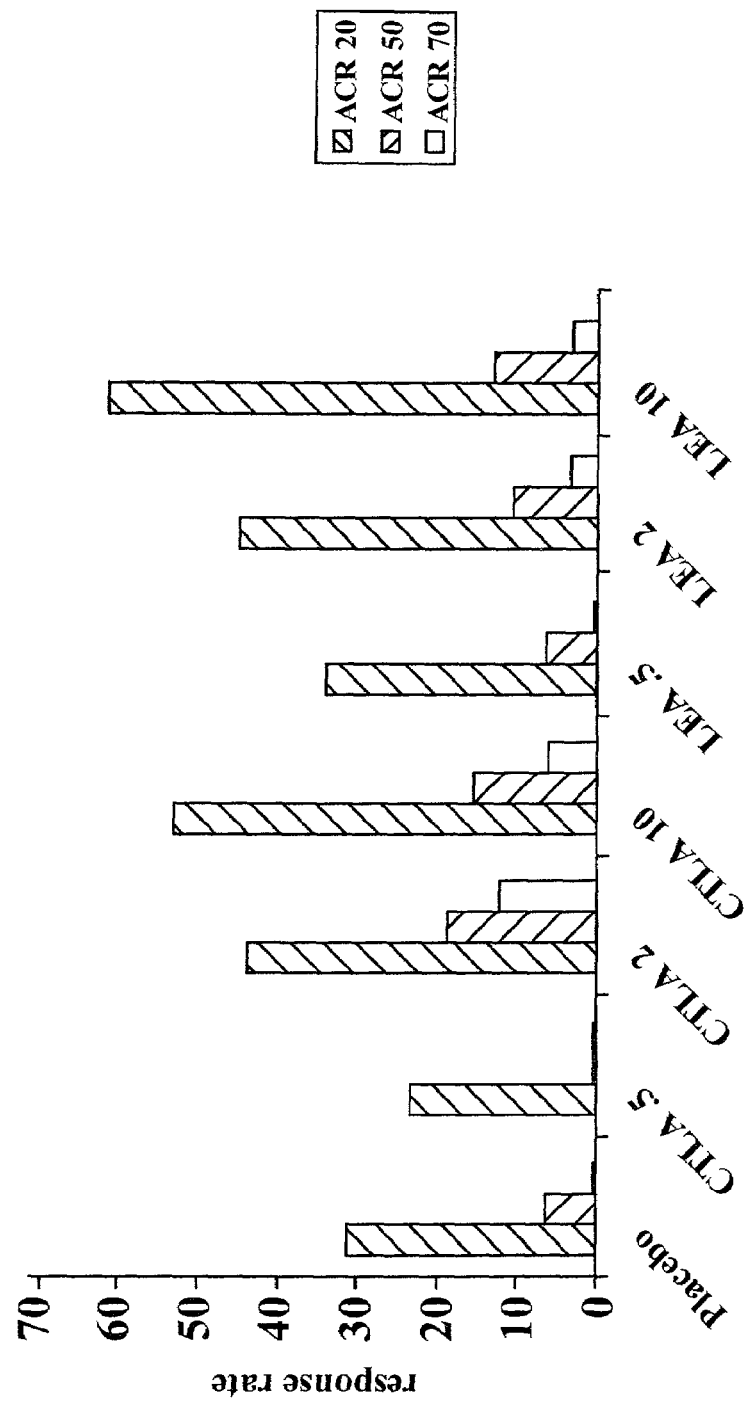
FIG. 3A: ACR responses at Day 85 as described in Example 3, infra: ACR-20, -50, and -70 responses.
Figure 3C:
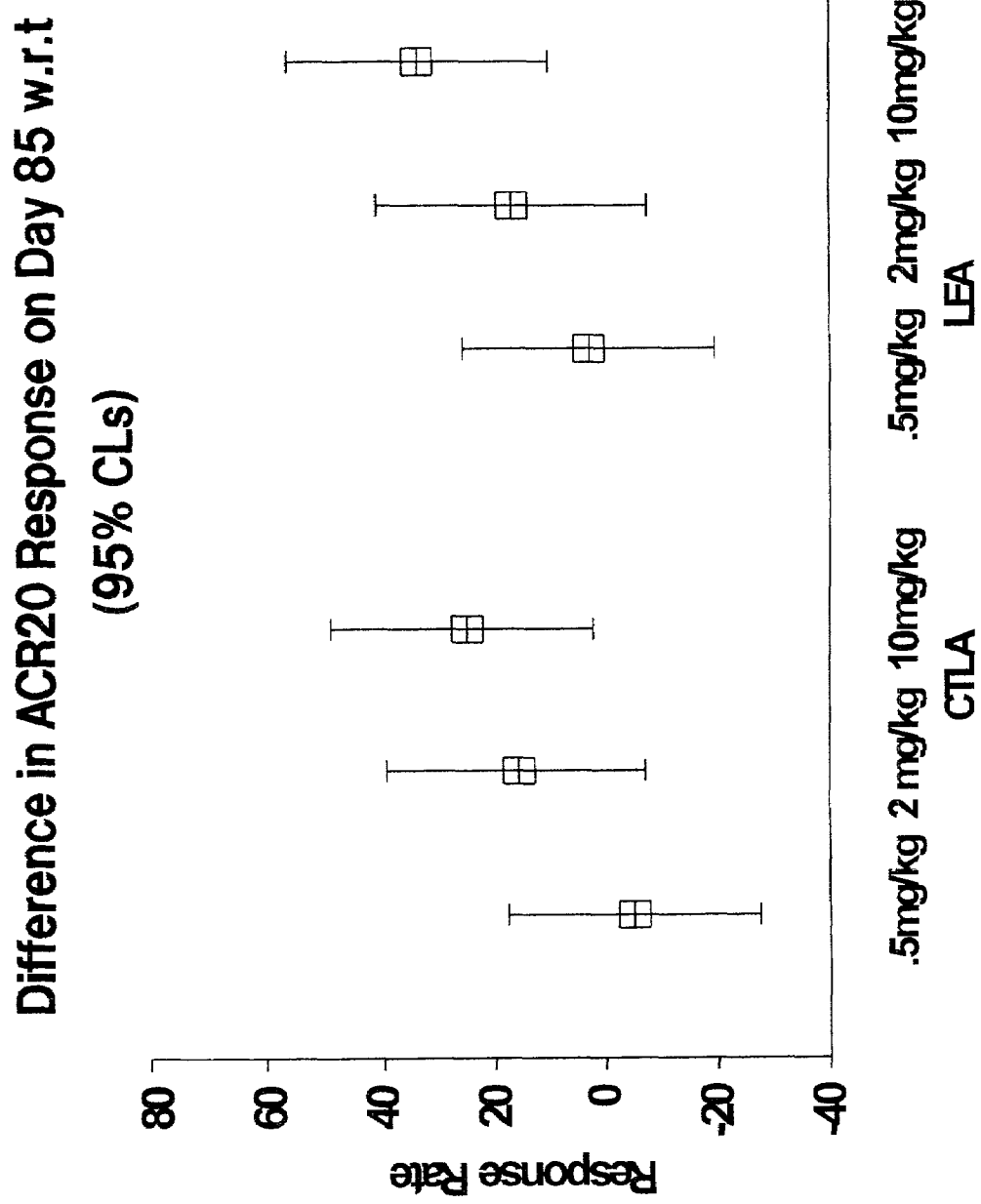
FIG. 3C: ACR-20 responses at Day 85 as described in Example 3, infra: Difference in ACR-20 response with respect to 95% confidence intervals.

The ACR-20, -50, and -70 responses of patients treated with CTLA4Ig, L104EA29YIg, or placebo at day 85 are summarized in FIG. 3A. Similarly, FIGS. 3B and C describe the ACR-20 responses with 95% confidence limits. The responses appear to be dose-dependent with a clear significant response at 10 mg/kg per body weight of the patient.

Figure 4A:
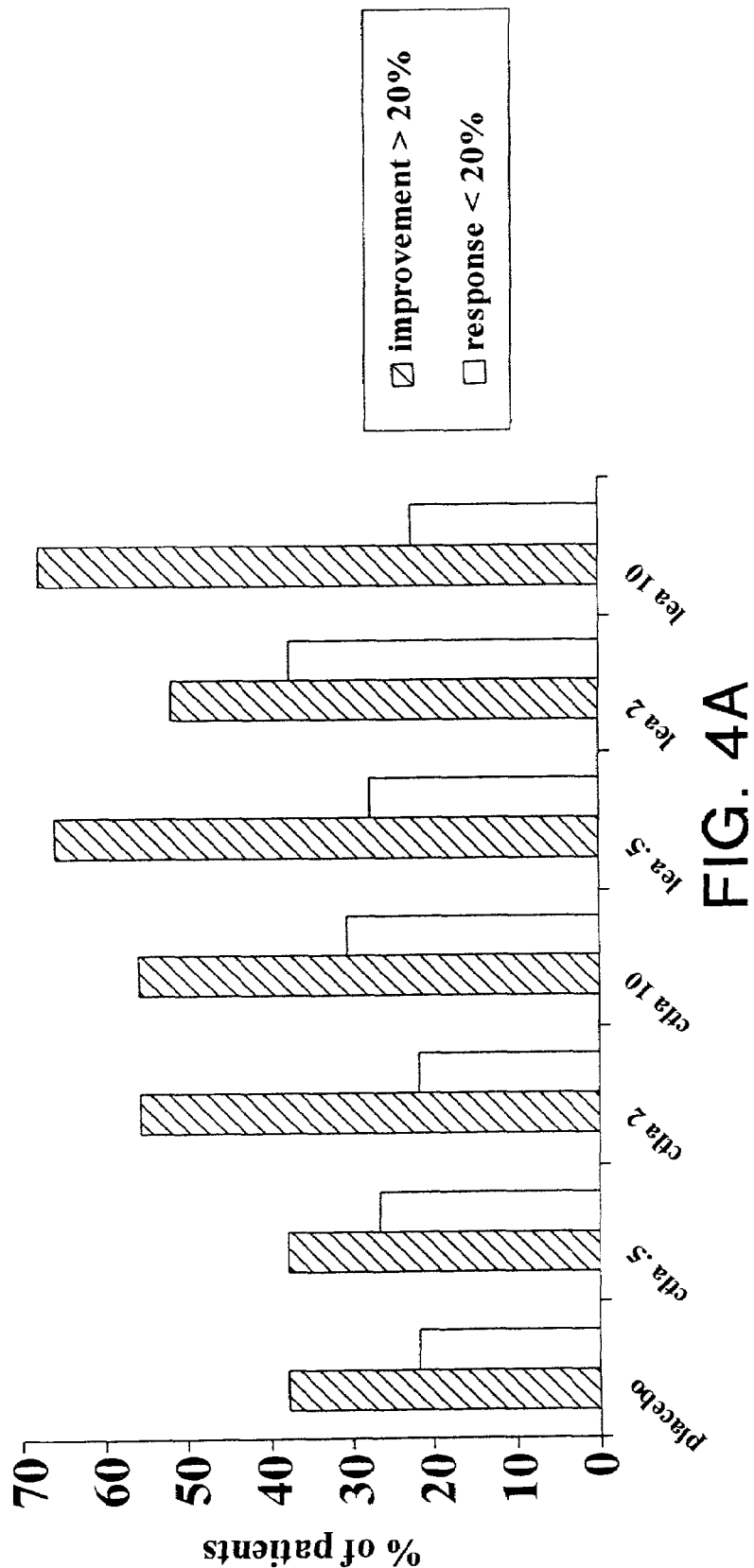
FIG. 4A: Basic (20% improvement) clinical responses in swollen and tender joint count in percentage of patients at Day 85 as described in Example 3, infra: basic clinical response, ACR-20.

The percent of patients having reduced swollen and tender joint counts compared to the patients having no response to treatment with CTLA4Ig, L104EA29YIg, or placebo, is shown in FIGS. 4A and B. The therapeutic responses appear to be dose-dependent. A larger percentage of patients show improvement of 20, 50, 70, and even 100% in the 2 and 10 mg/kg groups for both products.

Figure 5A:
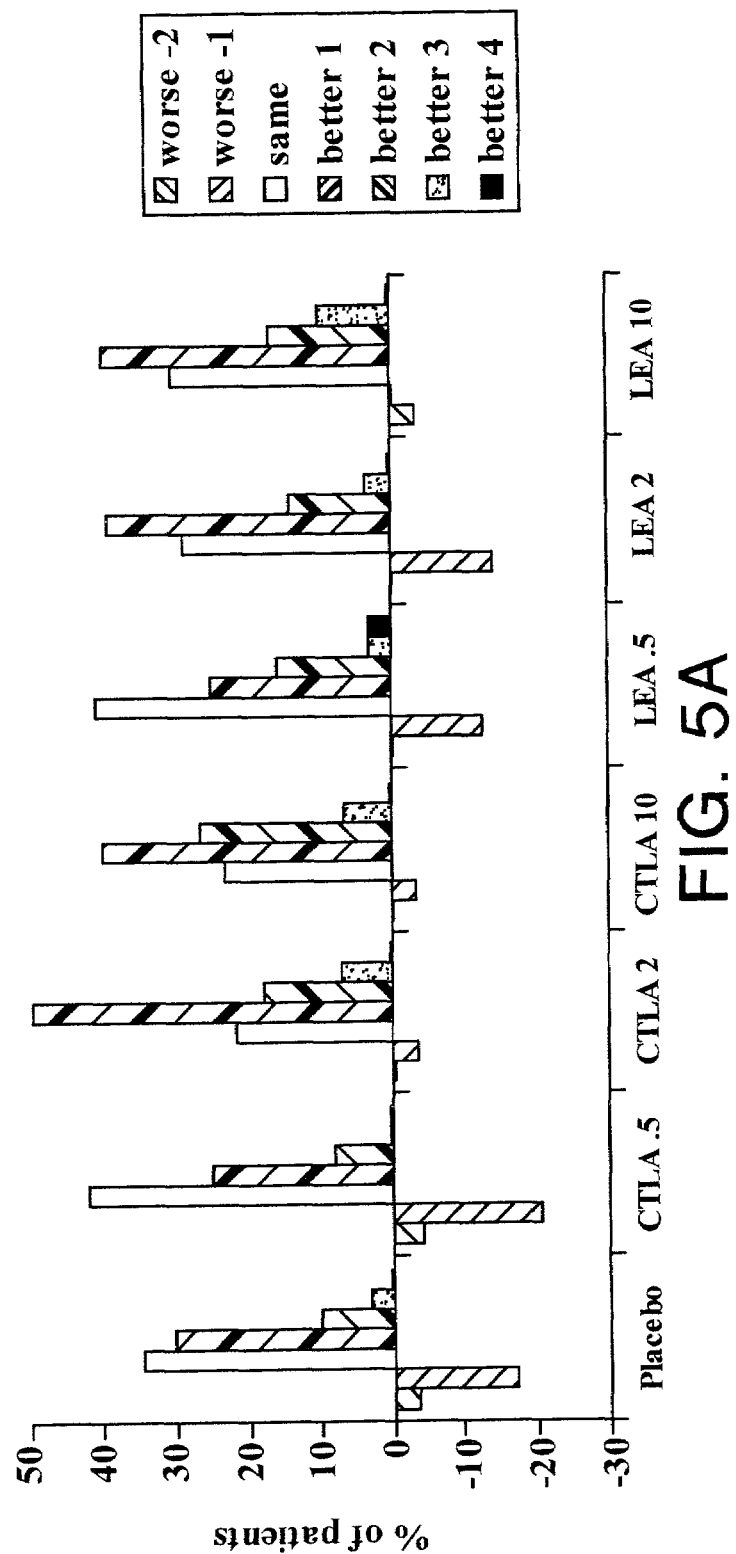
FIG. 5A: Pain response (by Likert scale by mean unit change from baseline) in percentage of patients at Day 85 as described in Example 3, infra: pain score changes from baseline.
Figure 5B:
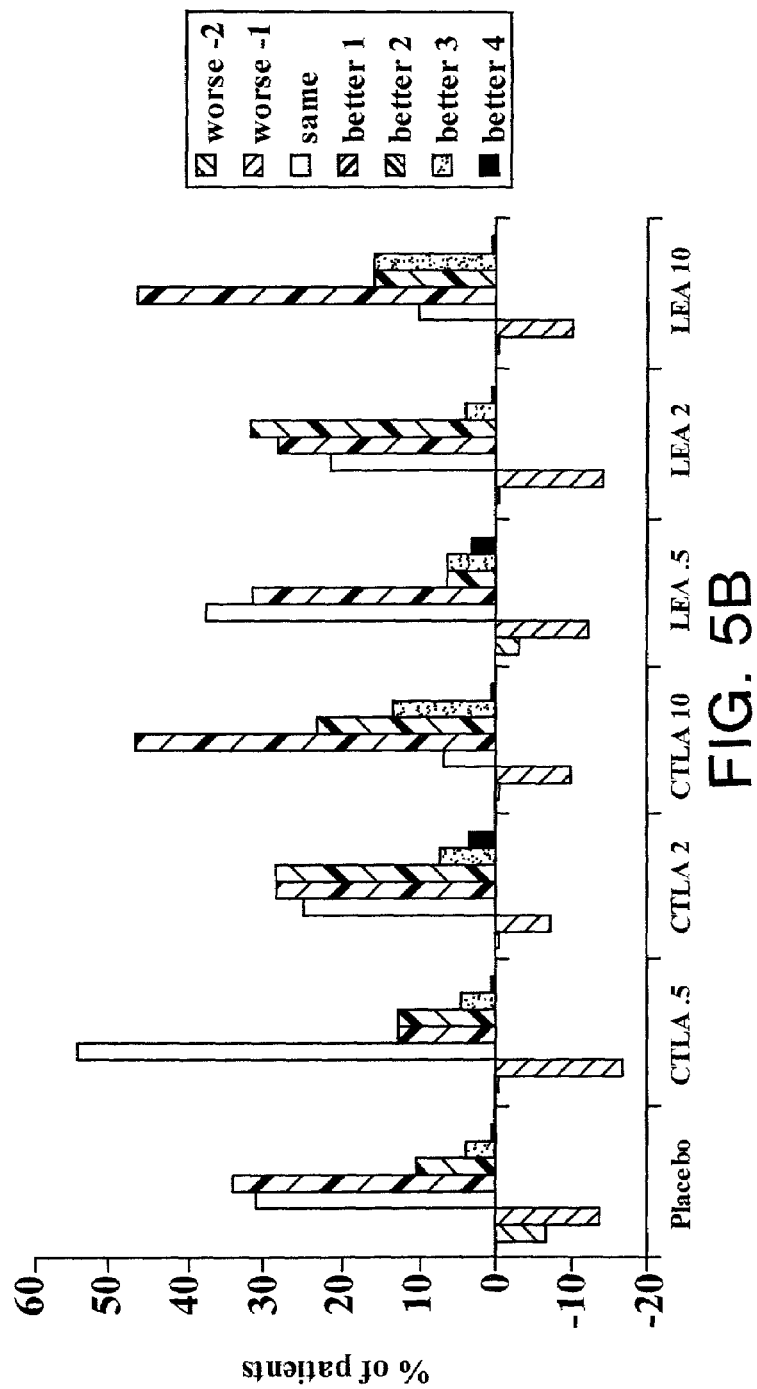
FIG. 5B: Patient global disease changes (by Likert scale by mean unit change from baseline) in percentage of patients at Day 85 as described in Example 3, infra: patient global disease activity changes.
Figure 5C:
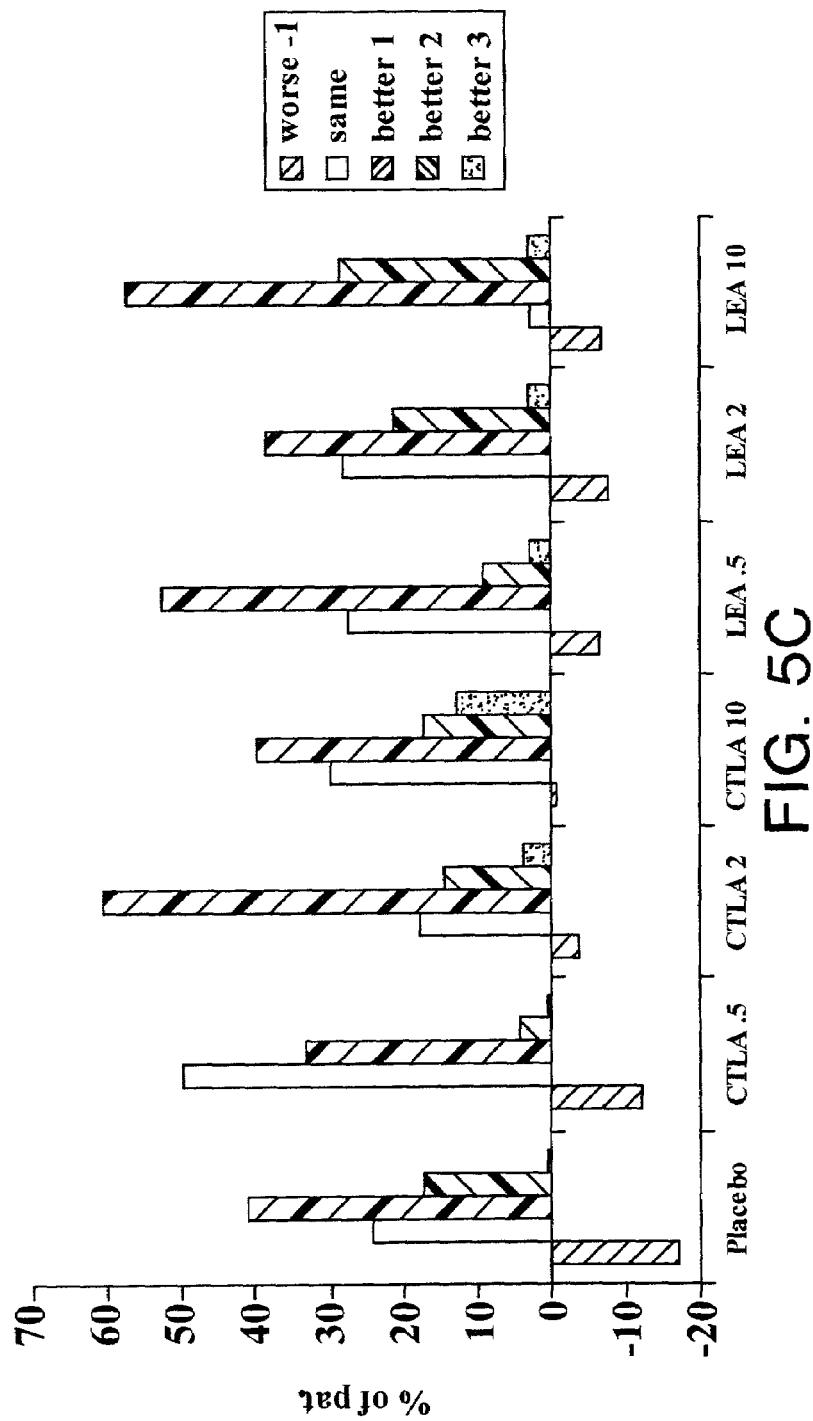
FIG. 5C: Physician global disease changes (by Likert scale by mean unit change from baseline) in percentage of patients at Day 85 as described in Example 3, infra: physician global disease activity changes.
Figure 5D:
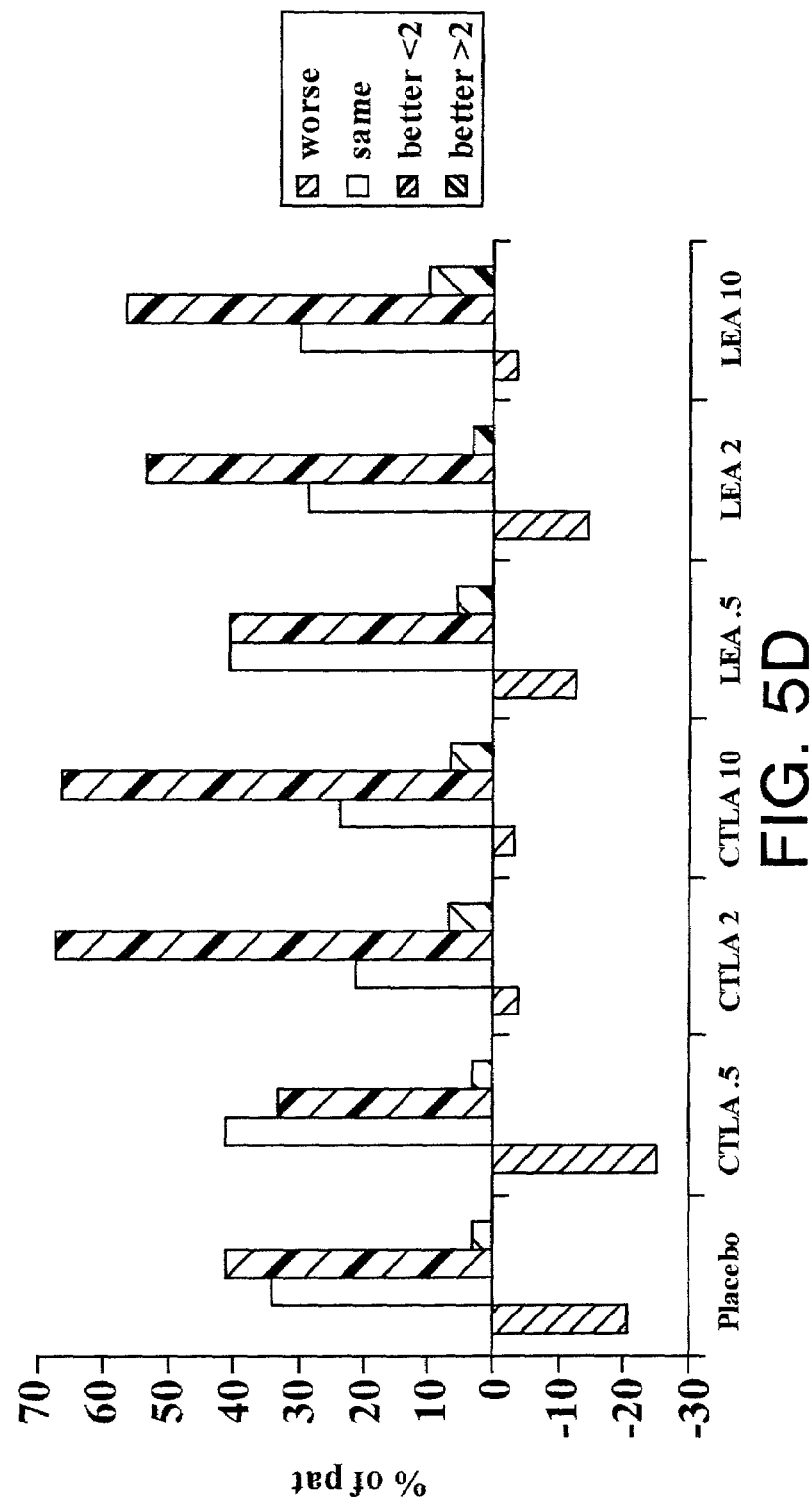
FIG. 5D: Pain (by Likert scale by mean unit change from baseline) in percentage of patients at Day 85 as described in Example 3, infra: pain changes from baseline.

The percent of patients having reduced pain, disease activity evaluated by patient and physician mean score units with CTLA4Ig, L104EA29YIg, or placebo, is shown in FIGS. 5A, B, C, and D. The therapeutic responses, as monitored by the Likert scale, appear to be dose-dependent in favor of the active treatment groups as compared to placebo on day 85. The Likert scale is a validated verbal rating scale using adjectives to rank the symptoms (The American College of Rheumatology Preliminary Core Set of Disease Activity Measures for Rheumatoid Arthritis Clinical Trials: Arthritis and Rheumatism, June 1993, 36(6):729-740).

Figure 6A:
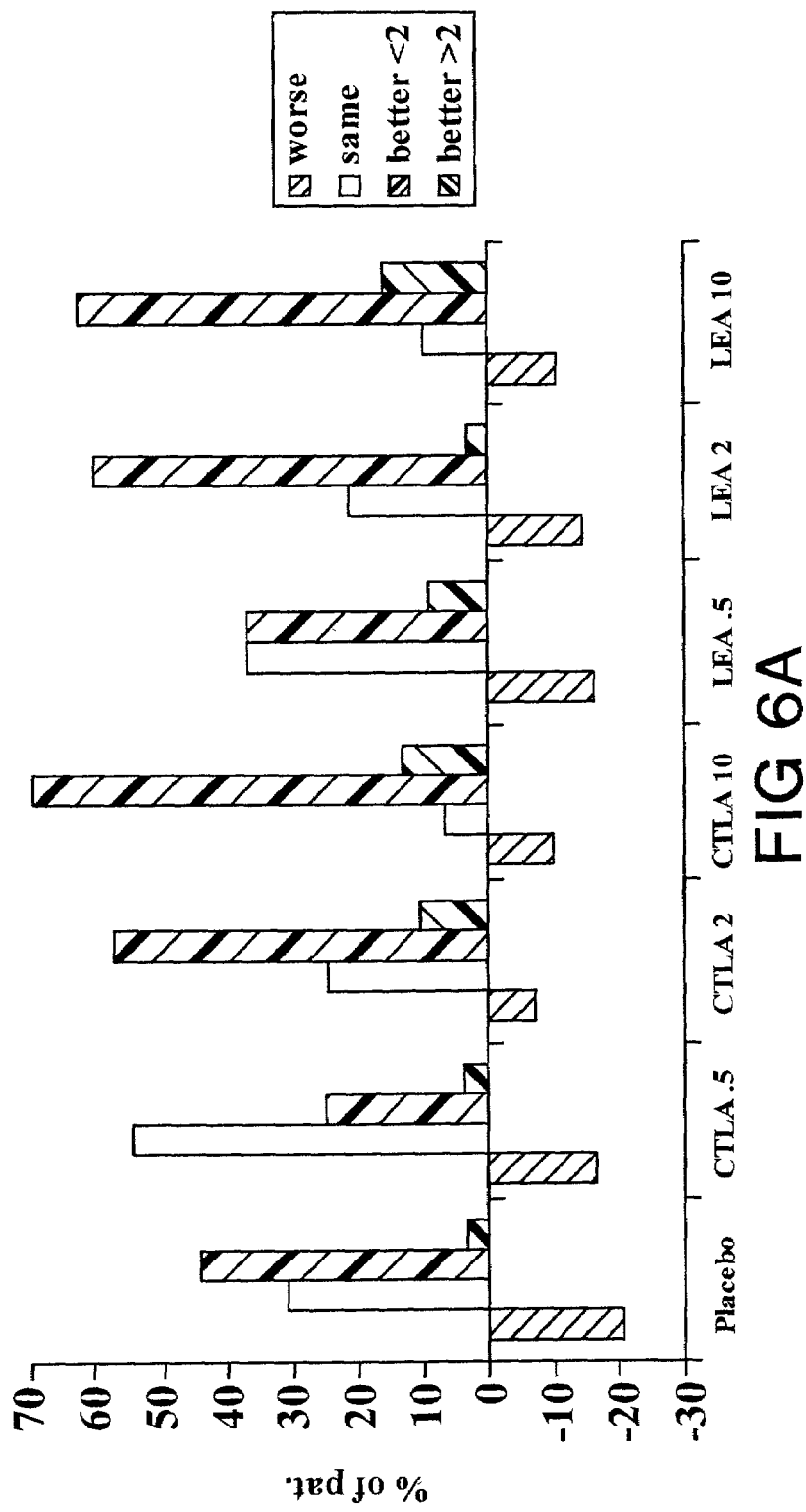
FIG. 6A: Patient global assessment of disease activity change from baseline by range of 2 units at Day 85 as described in Example 3, infra; disease activity improvement..
Figure 6B:
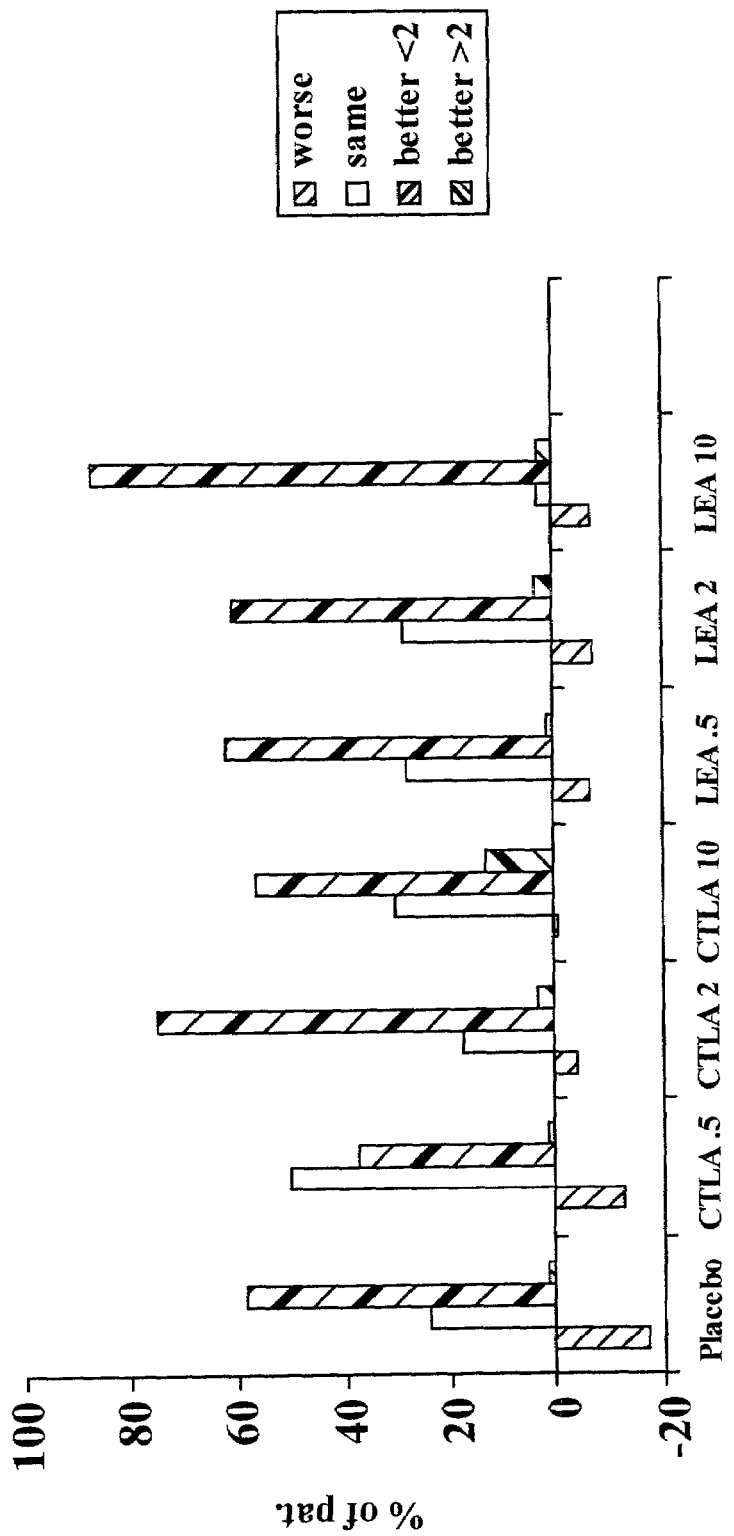
FIG. 6B: Physician global assessment of disease activity change from baseline by range of 2 units at Day 85 as described in Example 3, infra; disease activity improvement.

The patient and physician assessments of disease activity change from the baseline by at least 2 units, resulting from treatment with CTLA4Ig, L104EA29YIg, or placebo, are shown in FIGS. 6A and B. The responses appear to be dose-dependent with more marked improvement for the higher doses of active drugs.

Figure 7A:
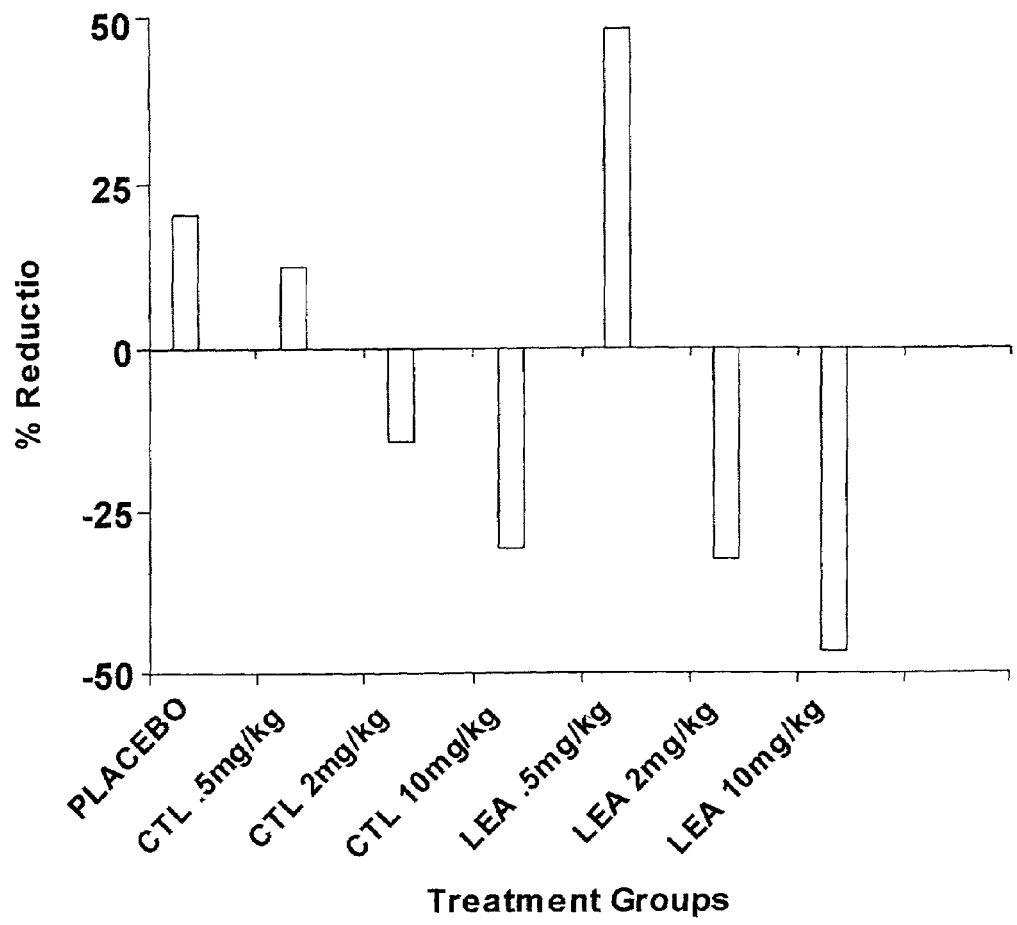
FIG. 7A: Percent reduction in C-reactive protein (CRP) levels at Day 85 as described in Example 3, infra: percentage reduction in CRP levels from baseline.
Figure 7B:
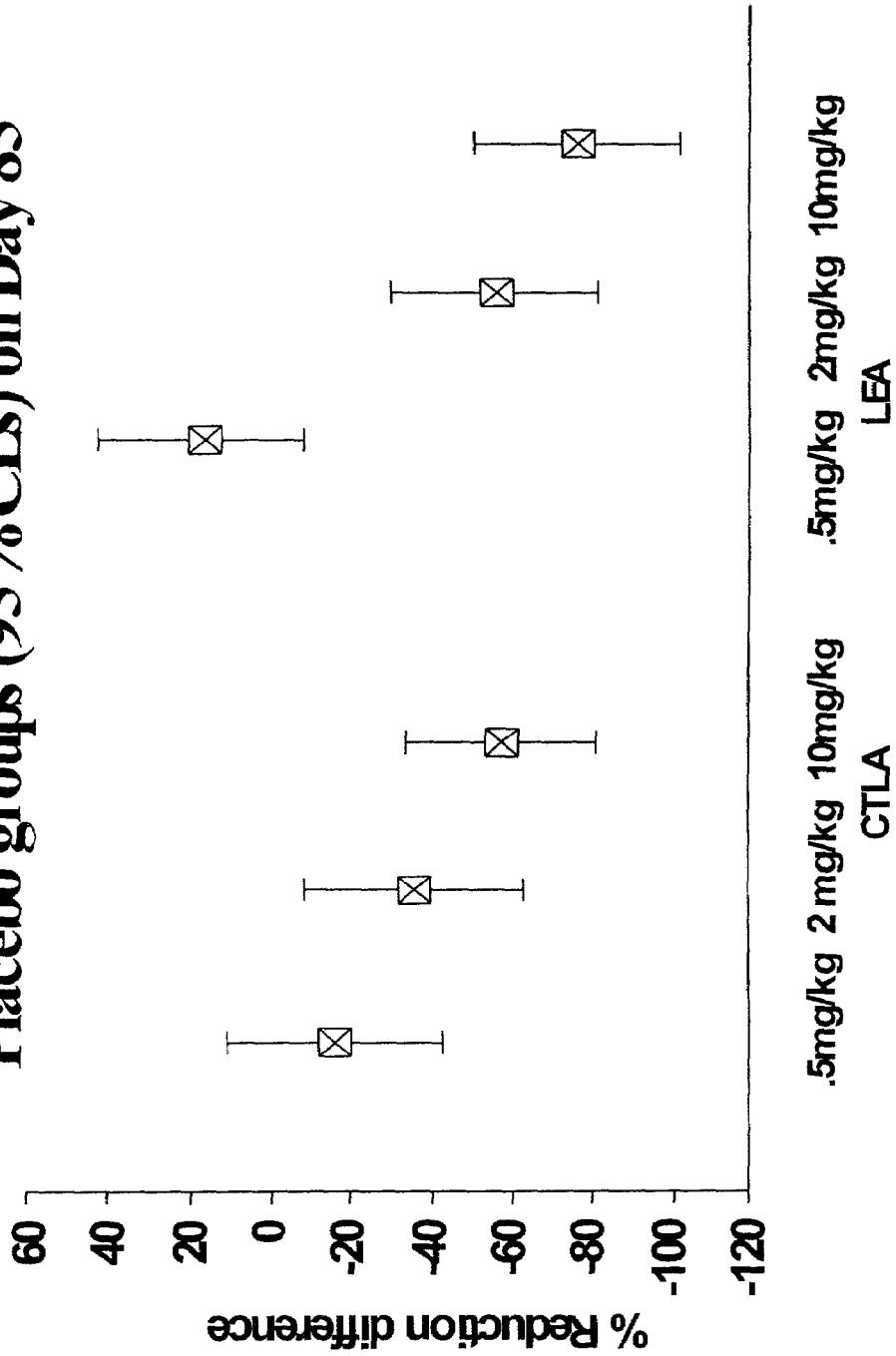
FIG. 7B: Difference in reduction in C-reactive protein (CRP) levels at Day 85 as described in Example 3, infra: percent reduction difference in CRP levels with 95% confidence intervals.

The percent reduction in C-reactive protein (CRP) levels in patients treated with CTLA4Ig, L104EA29YIg, or placebo, is shown in FIGS. 7A and B. The responses appear to be dose-dependent with a clear decrease for the 2 and 10 mg/kg active treatment groups. In addition, FIG. 7B showed that the difference is quite significant compared to placebo with 95% confidence intervals. FIG. 7C shows the changes in serum level changes from baseline at day 85.

Figure 8:
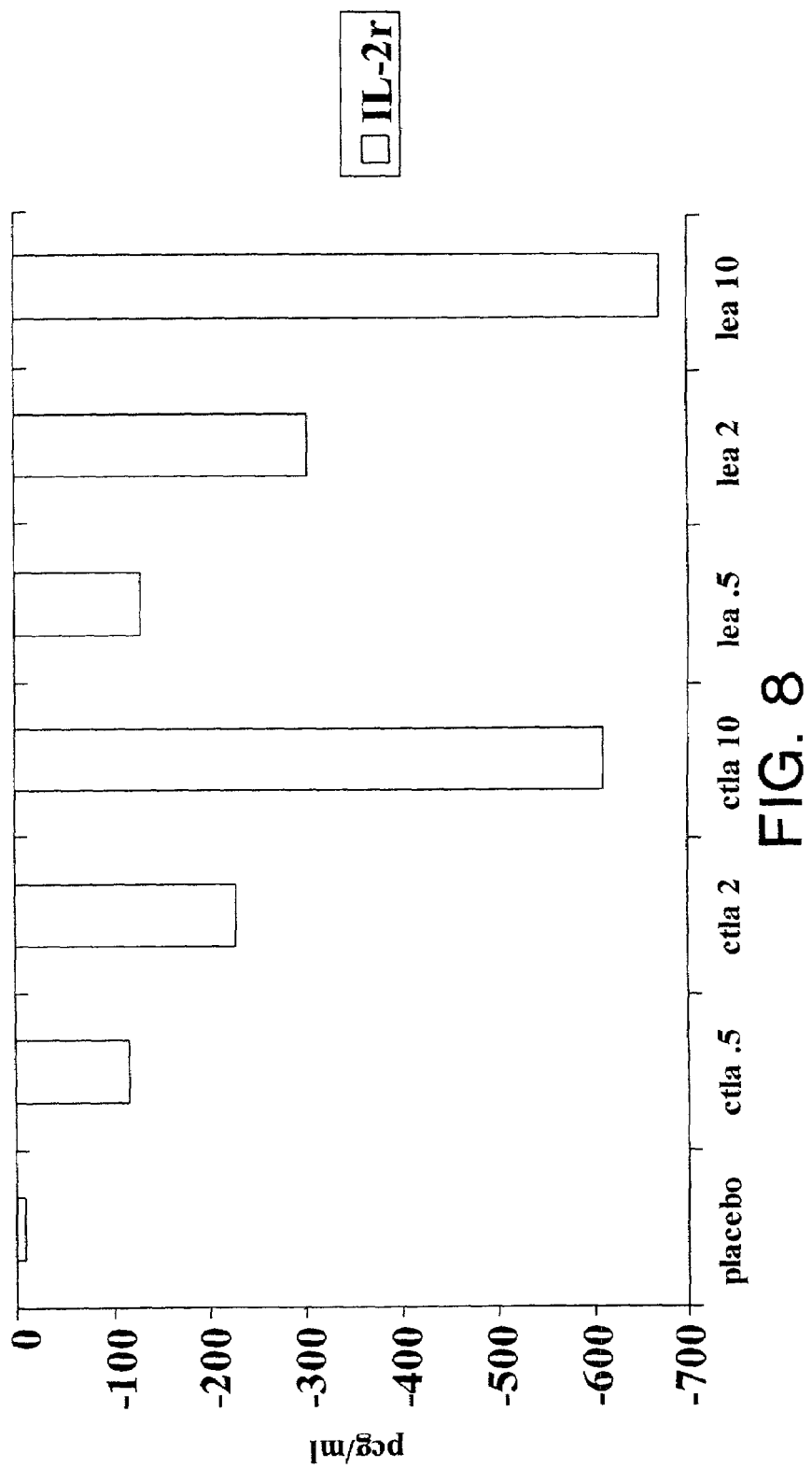
FIG. 8: Reduction in soluble IL-2 receptor levels mean change from baseline at Day 85 as described in Example 3, infra.

The amount of serum soluble IL-2 receptor in patients treated with CTLA4Ig, L104EA29YIg, or placebo, is shown in FIG. 8. The reduction in soluble IL-2 receptor levels appears to be dose-dependent.

The amount of serum soluble ICAM-1 and soluble E-selectin in patients treated with CTLA4Ig, L104EA29YIg, or placebo, is shown in FIG. 33. The reduction in soluble ICAM-1 and soluble E-selectin levels appears to be dose-dependent.

Figure 9A:
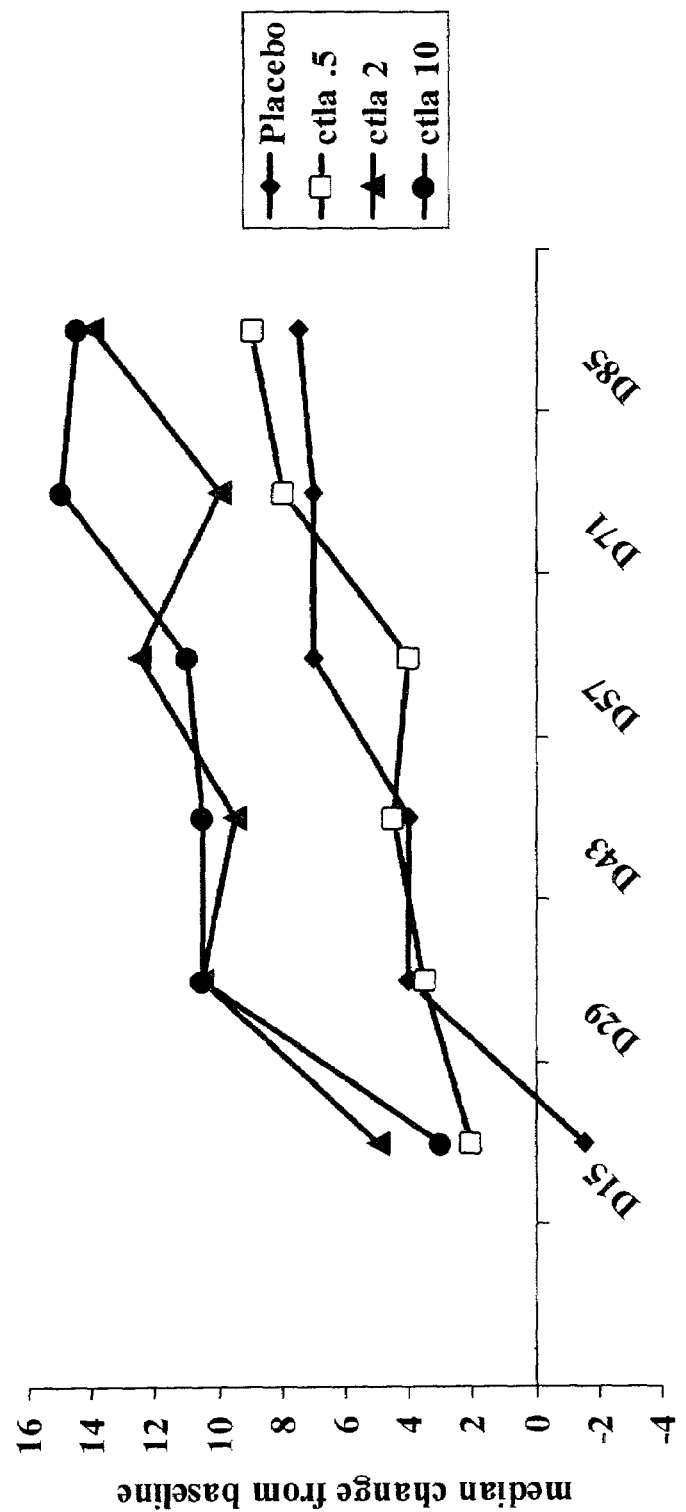
FIG. 9A: The effect of CTLA4Ig on tender joints over time as described in Example 3, infra: median difference from baseline.
Figure 9B:
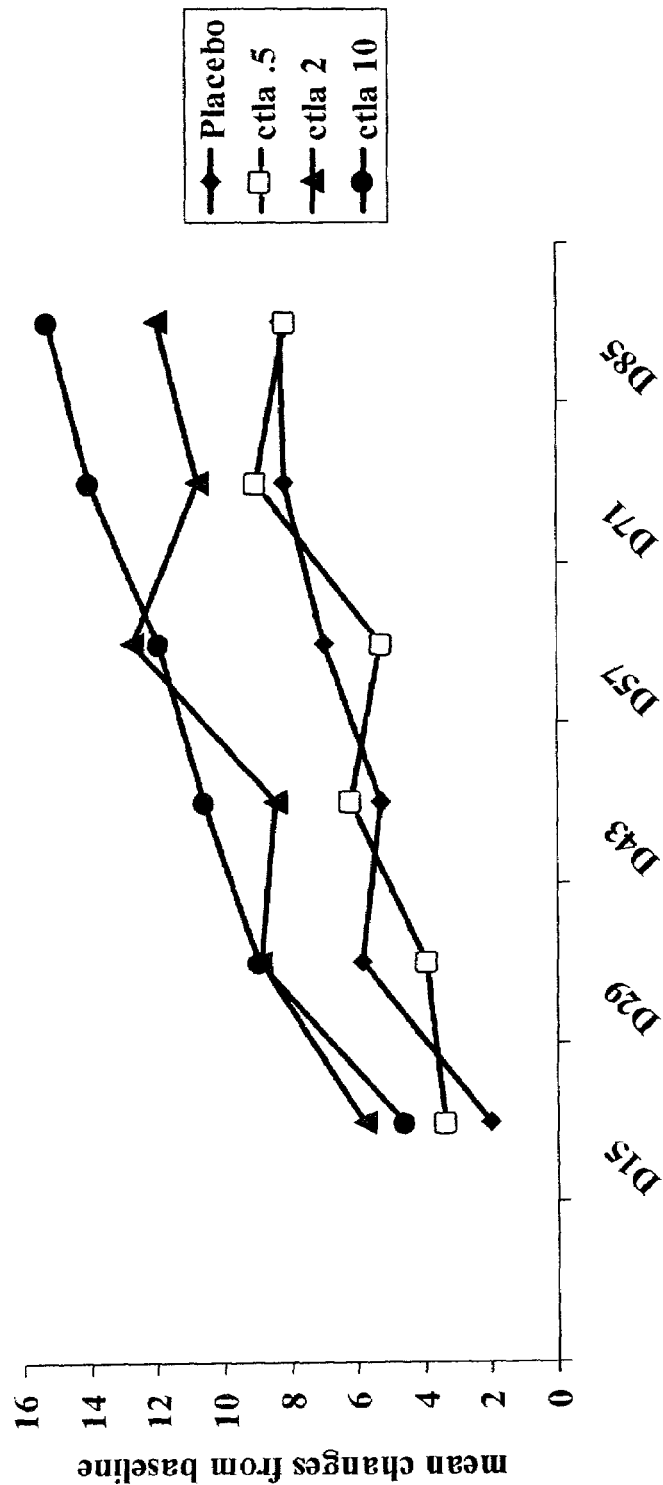
FIG. 9B: The effect of CTLA4Ig on tender joints over time as described in Example 3, infra: mean difference from baseline.

The median and mean tender joint counts in patients treated with CTLA4Ig or placebo over time are shown in FIGS. 9A and B. The change from baseline (e.g., reduction in tender joints) appears to be more important in the 2 and 10 mg/kg treated groups, than in the placebo or 0.5 mg/kg groups.

Figure 10A:
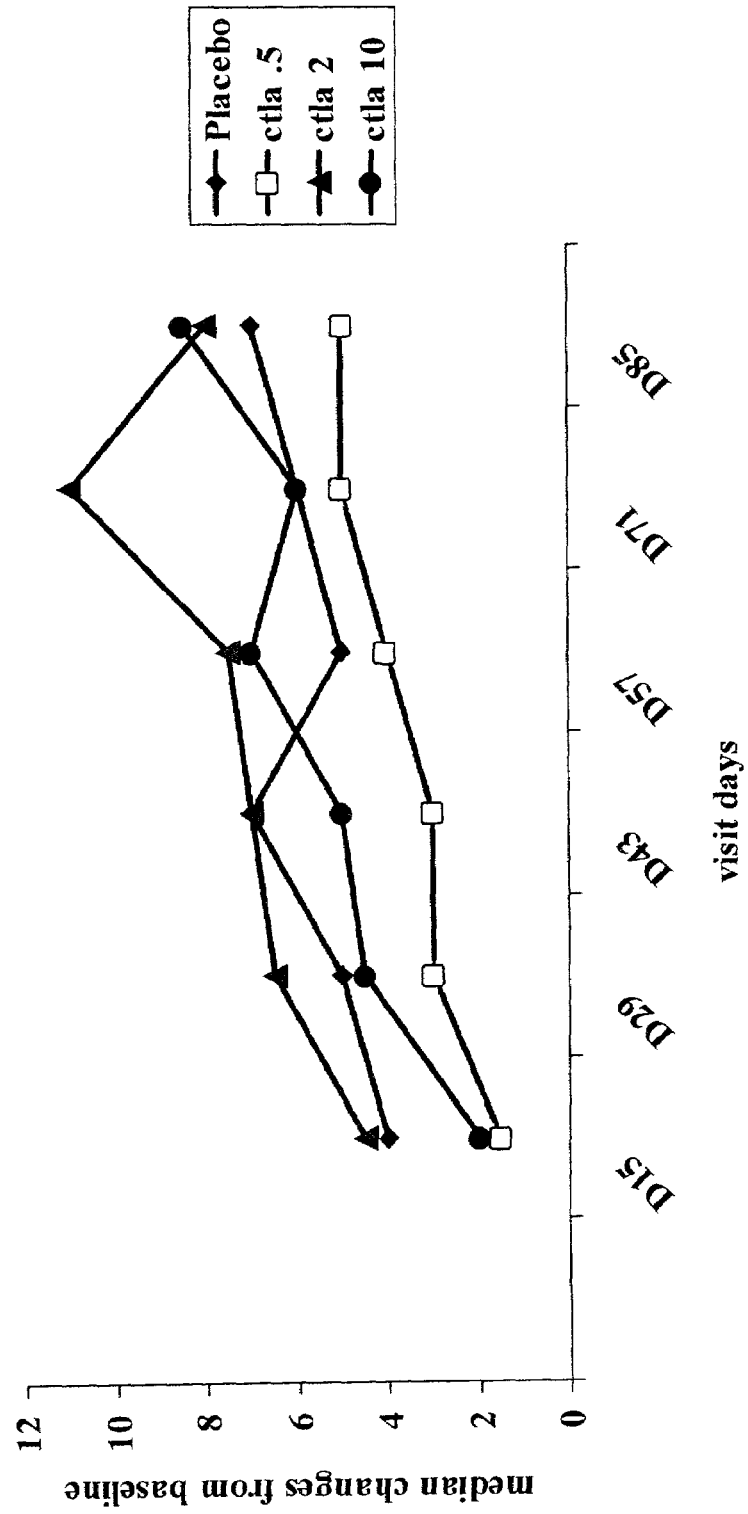
FIG. 10A: The effect of CTLA4Ig on swollen joints over time as described in Example 3, infra: median difference from baseline.
Figure 10B:
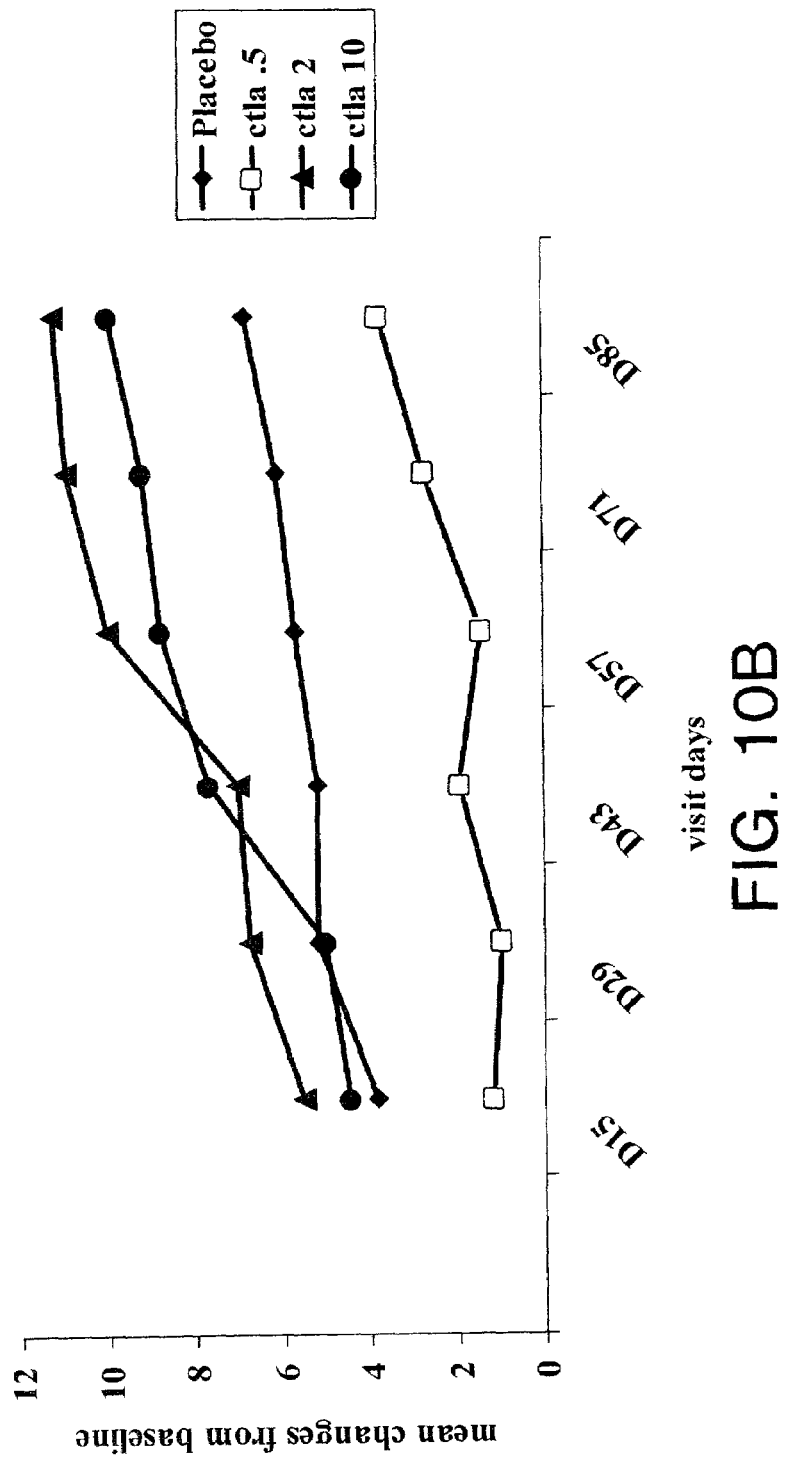
FIG. 10B: The effect of CTLA4Ig on swollen joints over time as described in Example 3, infra: mean difference from baseline.

The median and mean swollen joint counts in patients treated with CTLA4Ig or placebo over time are shown in FIGS. 10A and B. The change from baseline (e.g., reduction in swollen joints) appears to be more important in the 2 and 10 mg/kg treated groups than placebo or 0.5 mg/kg groups.

Figure 11:
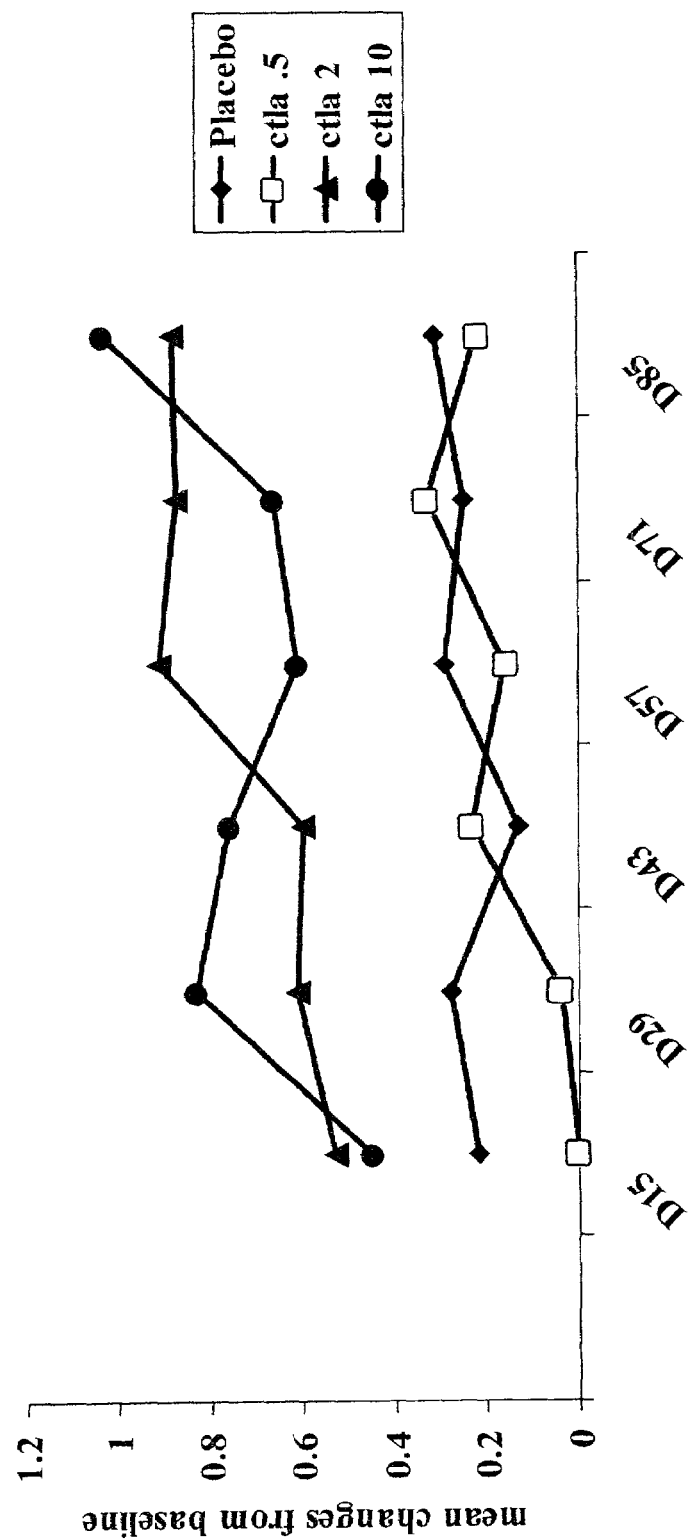
FIG. 11: The effect of CTLA4Ig on pain assessment mean difference from baseline over time as described in Example 3, infra.

The mean pain assessment scores over time in patients treated with CTLA4Ig or placebo are shown in FIG. 11. The change from baseline (e.g., reduction in pain) appears to be more important in the 2 and 10 mg/kg treated groups than placebo or 0.5 mg/kg groups.

Figure 12A:
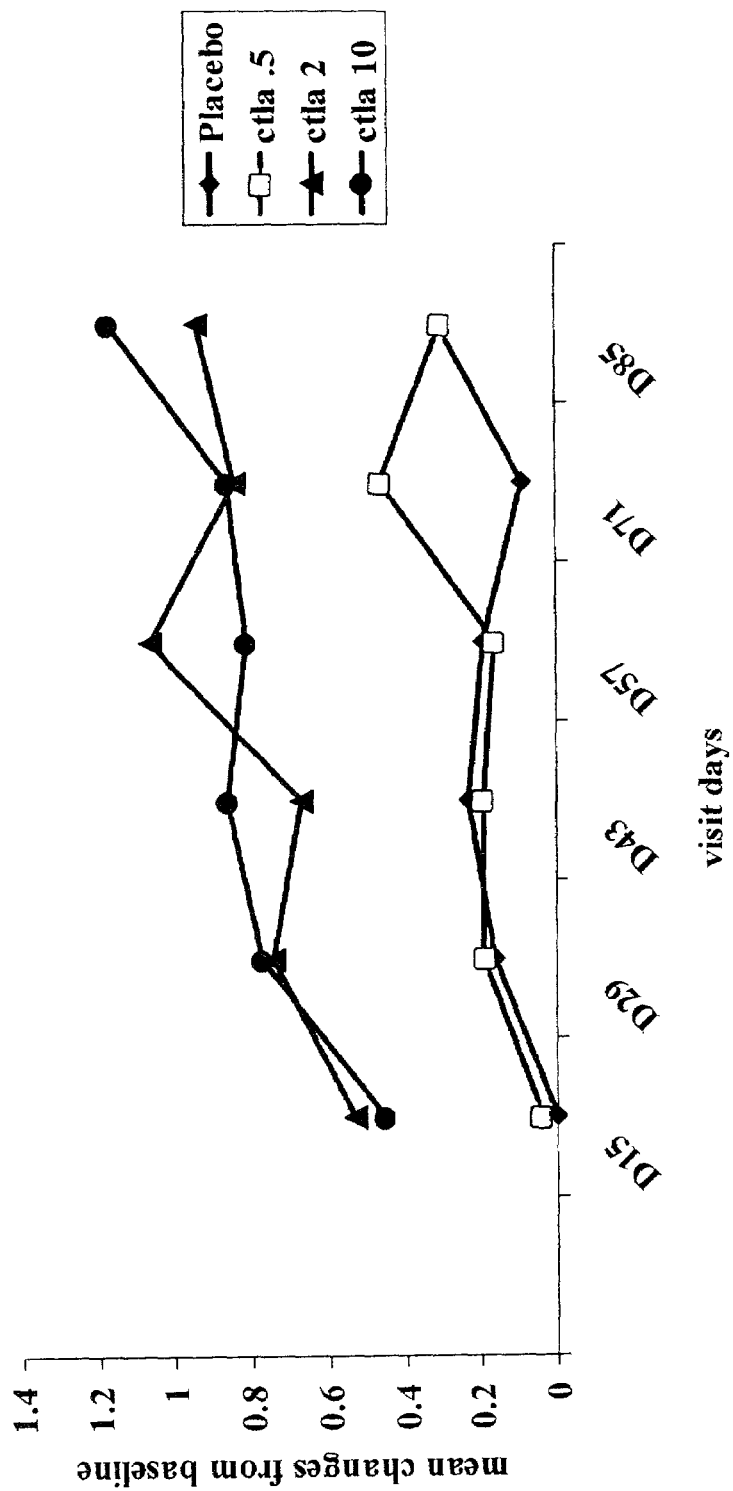
FIG. 12A: The effect of CTLA4Ig on patient assessment of disease activity mean difference from baseline over time as described in Example 3, infra.
Figure 12B:
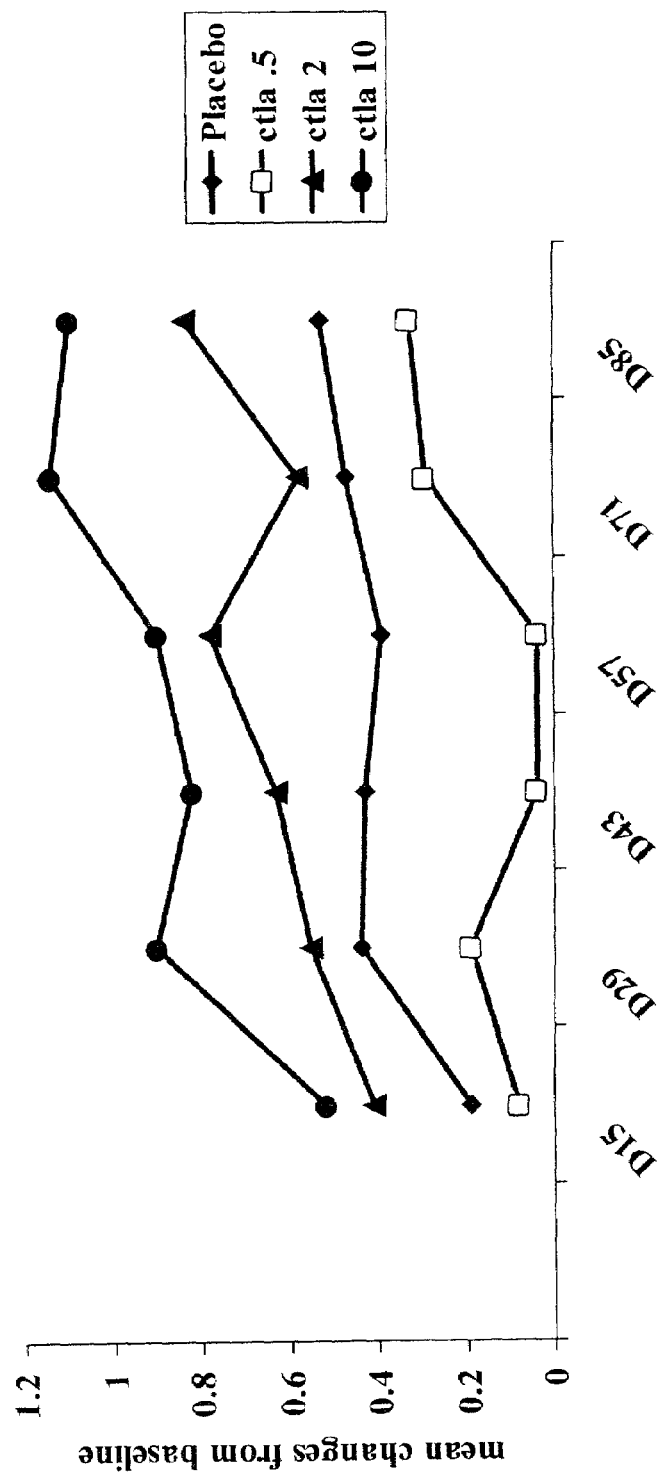
FIG. 12B: The effect of CTLA4Ig on physician assessment of disease activity mean difference from baseline over time as described in Example 3, infra.

The mean disease activity assessment scores assessed by patient or physician in patients treated with CTLA4Ig or placebo over time are shown in FIGS. 12A and B. The change from baseline (e.g., reduction in disease activity) appears to be more important in the 2 and 10 mg/kg treated groups than placebo or 0.5 mg/kg groups.

Figure 13A:
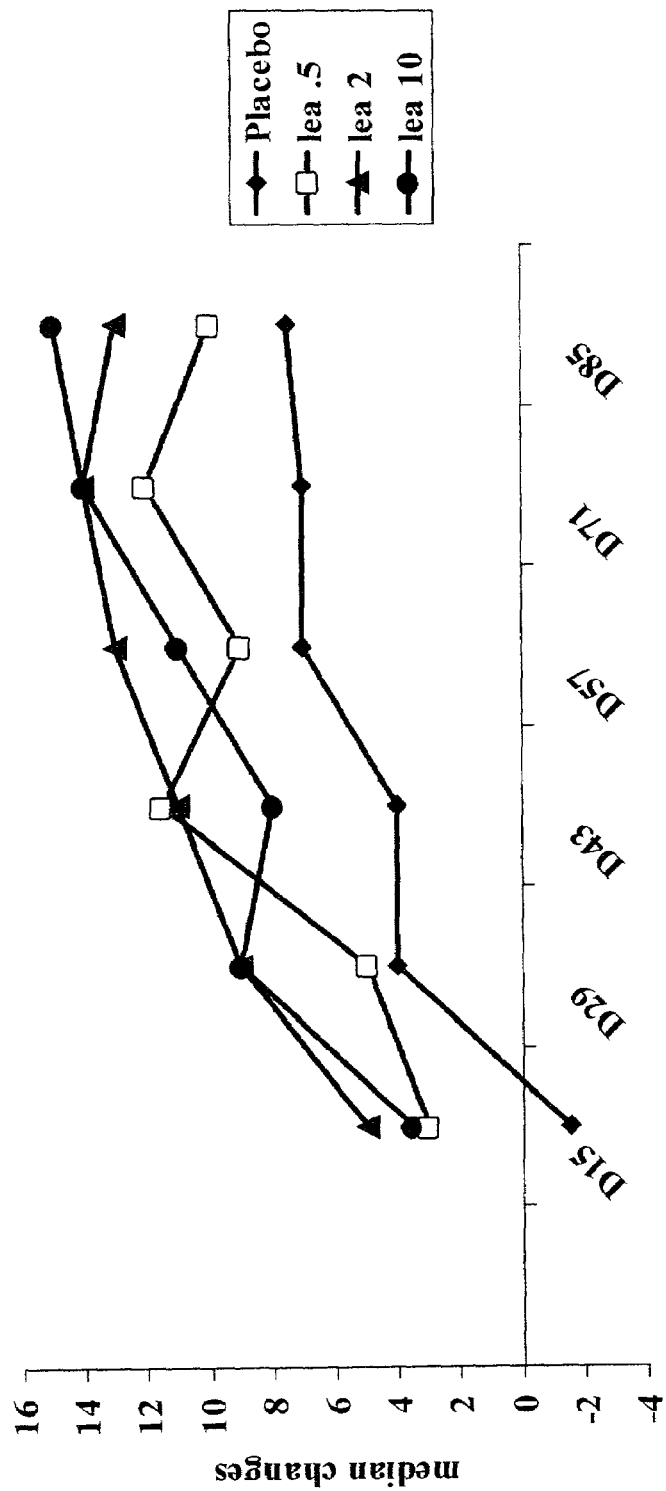
FIG. 13A: The effect of L104EA29YIg on tender joints over time as described in Example 3, infra: median difference from baseline.
Figure 13B:
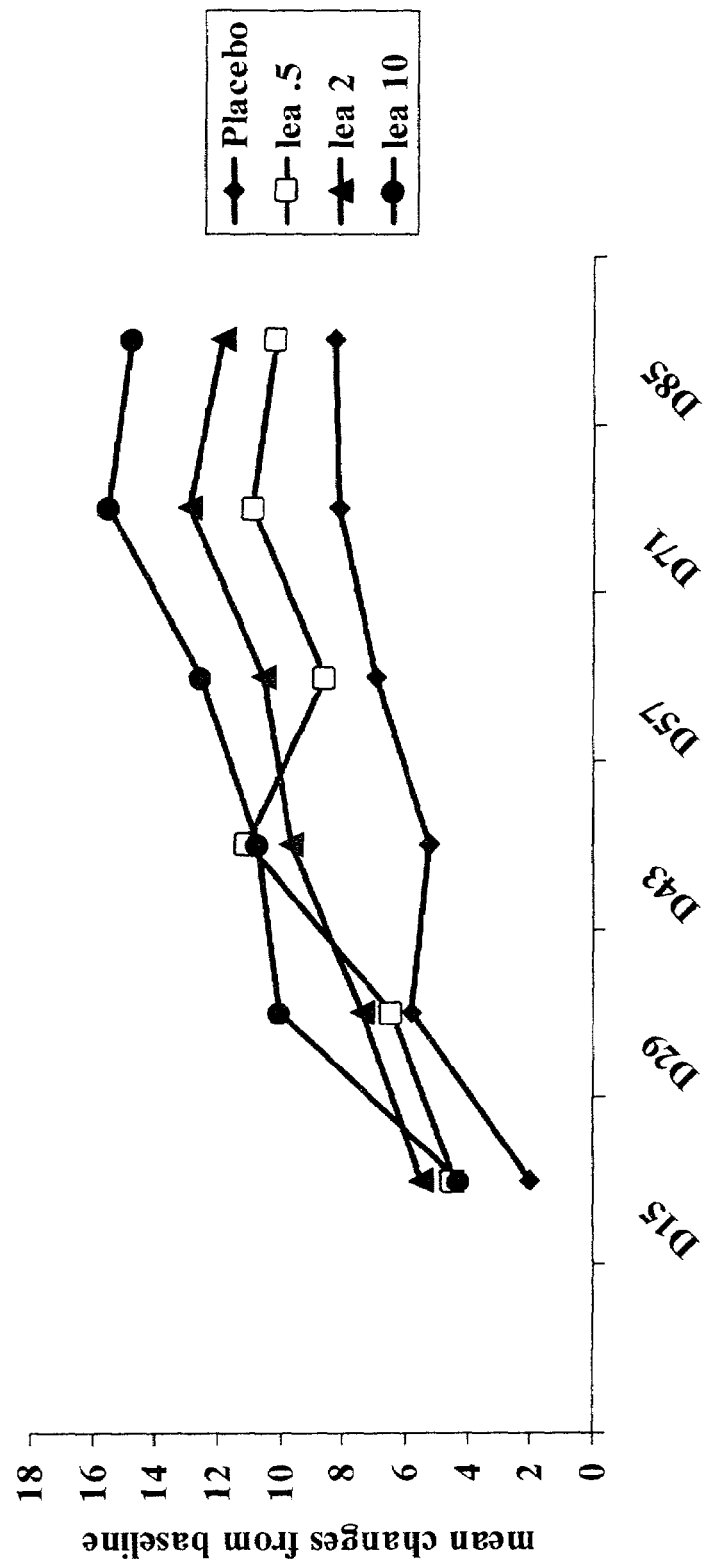
FIG. 13B: The effect of L104EA29YIg on tender joints over time as described in Example 3, infra: mean change from baseline.

The median and mean tender joint counts in patients treated with L104EA29YIg (denoted as LEA in the figures) or placebo over time are shown in FIGS. 13A and B. The change from baseline (e.g., reduction in tender joints) appears to be dose-dependent.

Figure 14A:
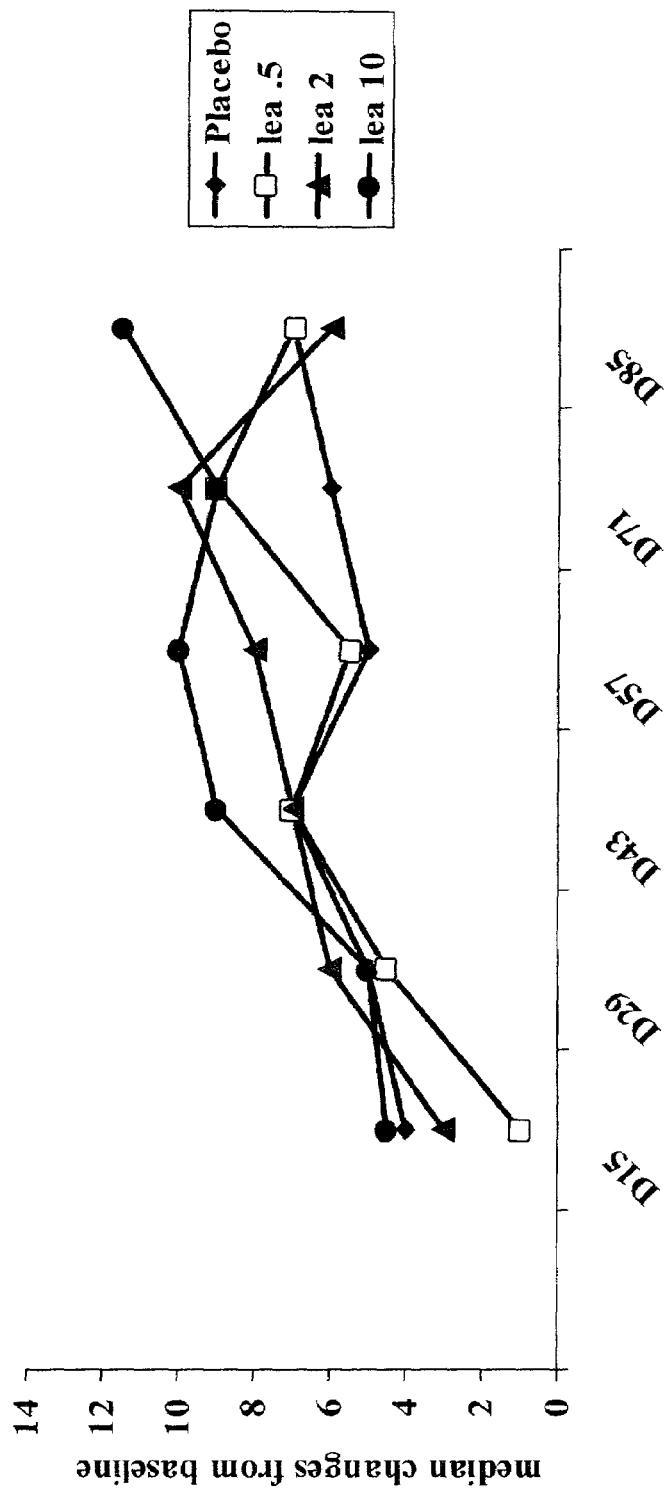
FIG. 14A: The effect of L104EA29YIg on swollen joints over time as described in Example 3, infra: median difference from baseline.
Figure 14B:
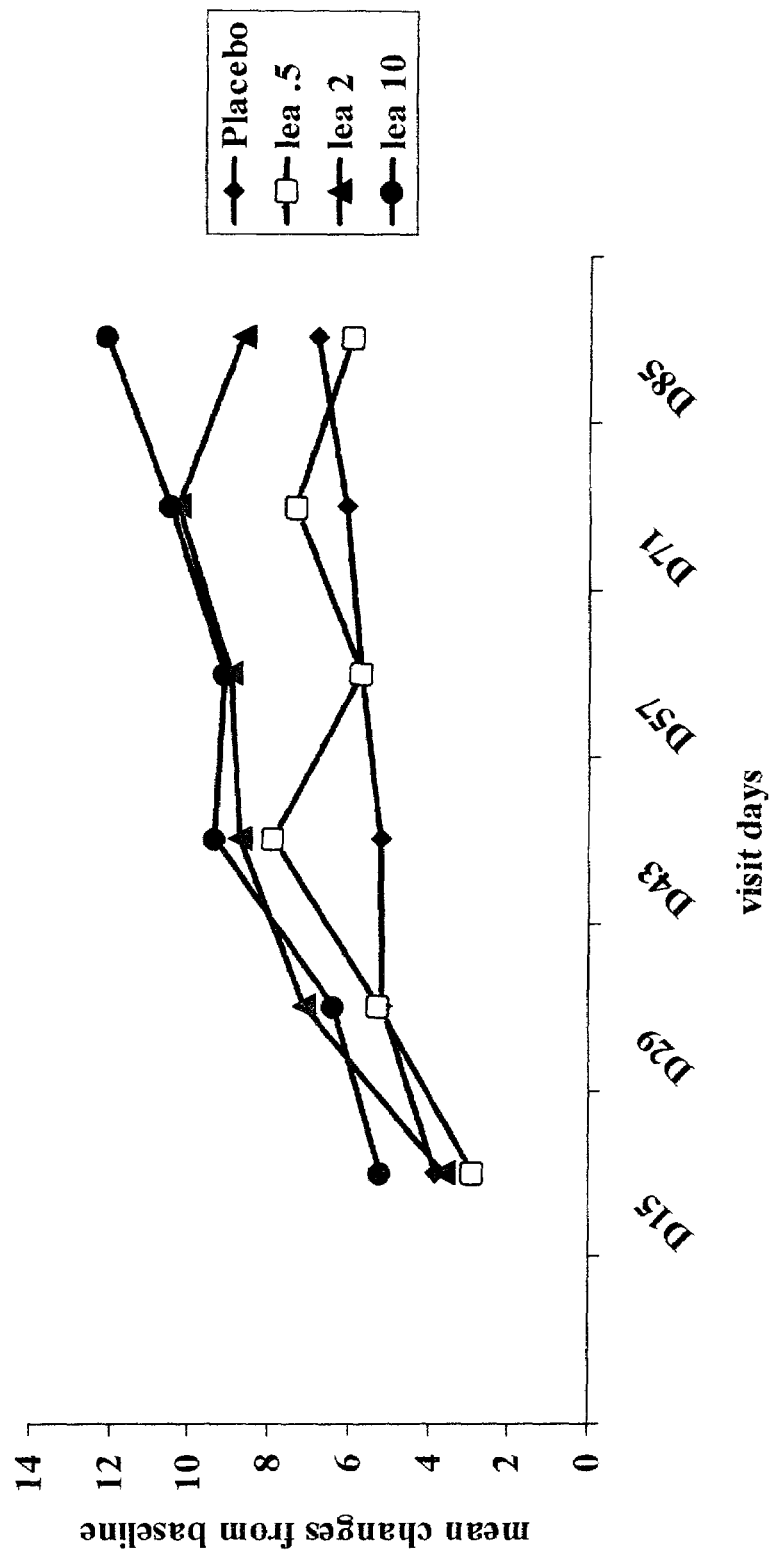
FIG. 14B: The effect of L104EA29YIg on swollen joints over time as described in Example 3, infra: mean change from baseline.

The median and mean swollen joint counts in patients treated with L104EA29YIg (denoted as LEA in the figures) or placebo over time are shown in FIGS. 14A and B. The change from baseline (e.g., reduction in swollen joints) appears to be more important in the 2 and 10 mg/kg treated groups than placebo or 0.5 mg/kg groups.

Figure 15:
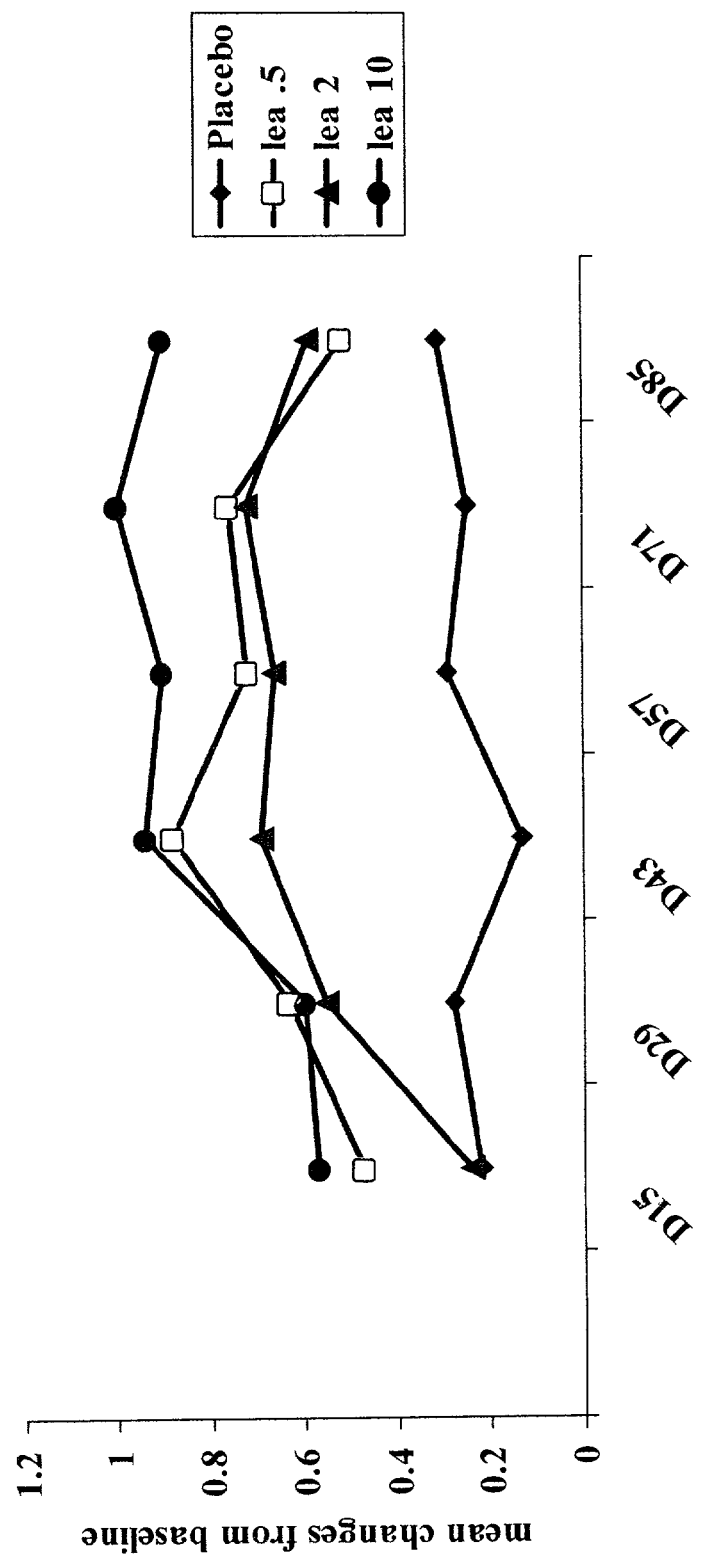
FIG. 15: The effect of L104EA29YIg on pain assessment over time as described in Example 3, infra: mean change from baseline over time.

The mean pain assessment scores in patients treated with L104EA29YIg (denoted as LEA in the figures) or placebo over time are shown in FIG. 15. The change from baseline (e.g., reduction in pain) appears to be dose-dependent.

Figure 16A:
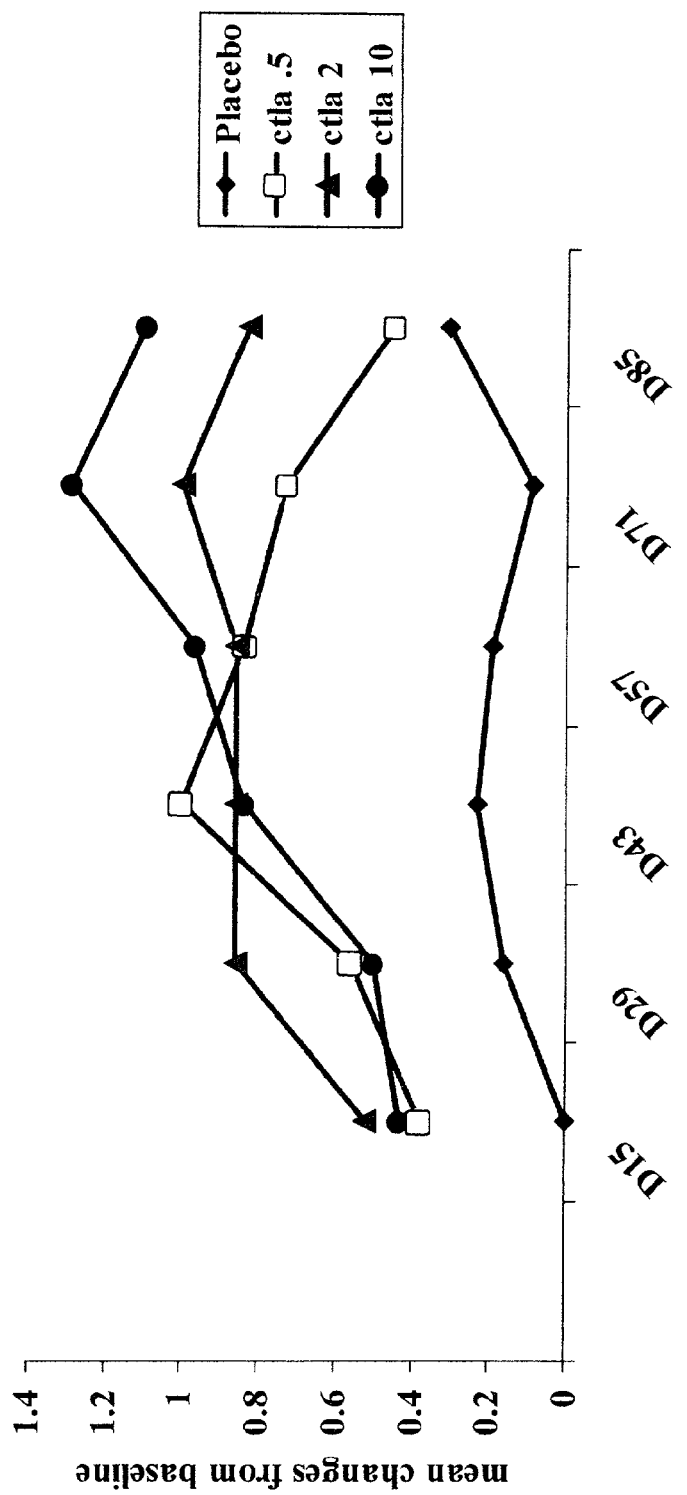
FIG. 16A: The effect of L104EA29YIg on patient assessment of disease activity mean difference from baseline over time as described in Example 3, infra.
Figure 16B:
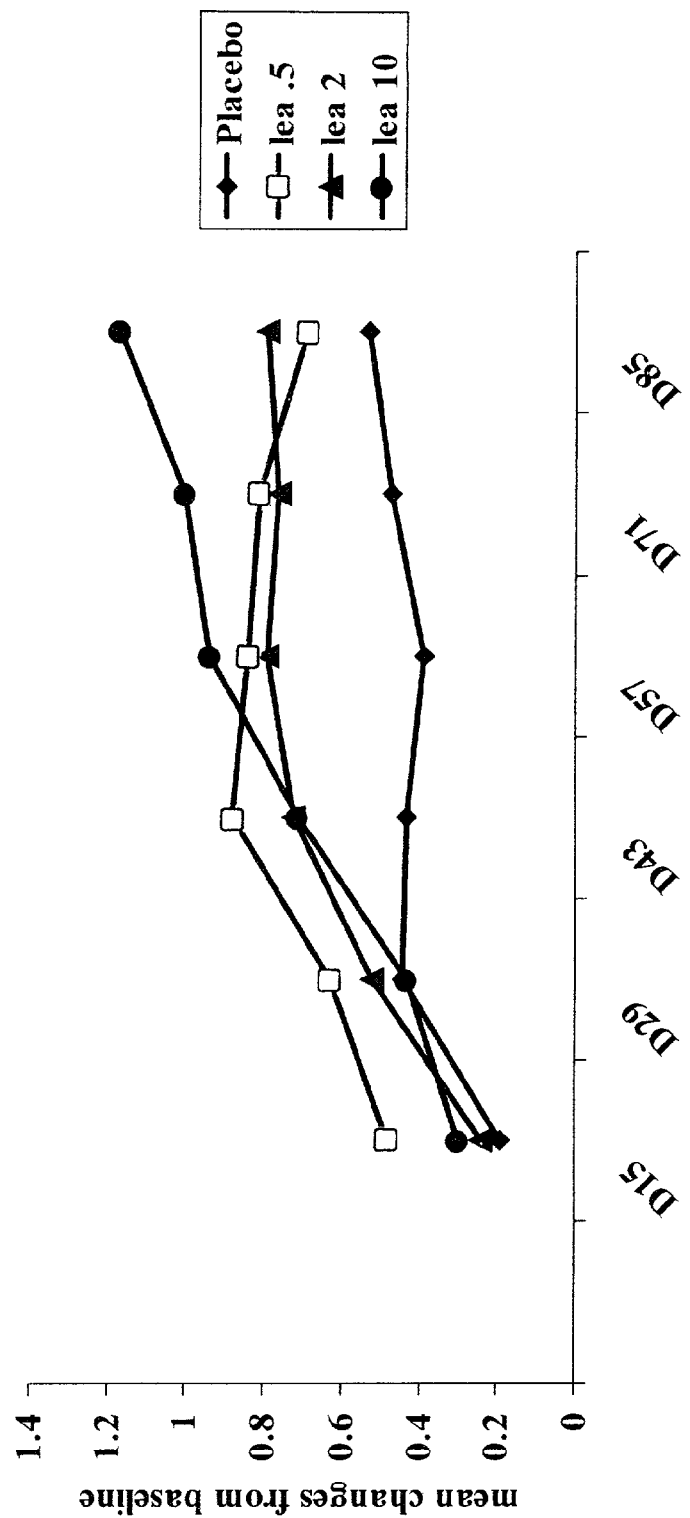
FIG. 16B: The effect of L104EA29YIg on physician assessment of disease activity mean difference from baseline over time as described in Example 3, infra.

The mean disease activity assessment scores evaluated by patient or physician in patients treated with L104EA29YIg (denoted as LEA in the figures) or placebo over time are shown in FIGS. 16A and B. The change from baseline (e.g., reduction in disease activity) appears to be dose-dependent.

Figure 17:
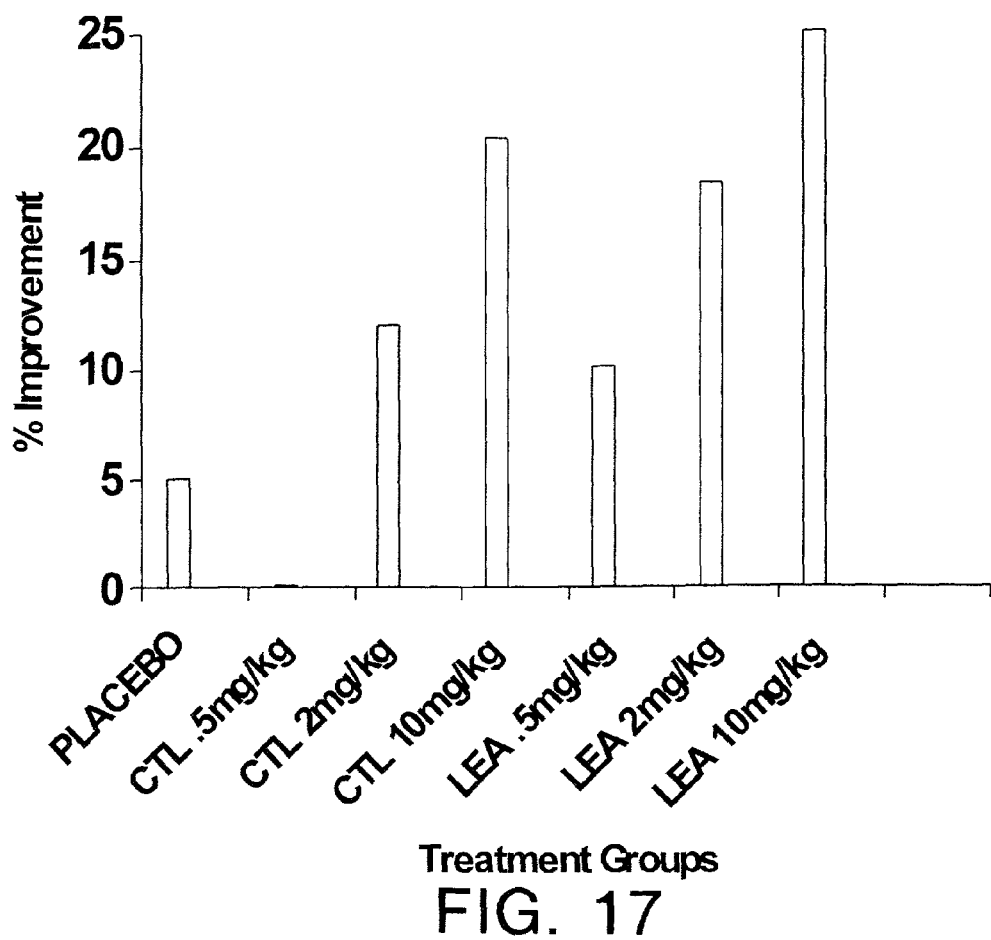
FIG. 17: Percent improvement in patient disability assessed by Health Assessment Questionnaire (HAQ) compared to the baseline at Day 85 with CTLA4Ig and L104EA29YIg treatment as described in Example 3, infra.

The percent improvement of physical disability assessed by HAQ at day 85 for patients treated with CTLA4Ig, L104EA29YIg, or placebo are shown in FIG. 17 (Health Assessment Questionnaire (HAQ); Fries, J. F., et al., 1982 *J.* of *Rheumatology* 9:789-793). There is a clear dose dependent improvement with this parameter.

The changes from baseline for soluble IL-2r and C-reactive protein levels were dose-dependent in both treatment groups. After treatment, soluble IL-2r levels were −2%, −10%, and −22% for CTLA4Ig and −4%, −18%, and −32% for L104EA29YIg at 0.5, 2.0, and 10.0 mg/kg respectively, compared to +3% for the placebo. C-reactive protein levels were +12%, −15%, and −32% for CTLA4Ig and +47%, −33%, and −47% for L104EA29YIg at 0.5, 2.0, and 10.0 mg/kg respectively, compared to +20% for the placebo (FIG. 7A).

No clinically remarkable findings with respect to routine hematology testing, chemistry laboratory testing with the exception of slight suppressions in IgA and IgG levels at the higher doses of both drugs, physical findings, or vital signs assessments were observed. Notably, neither medication induced drug-specific antibodies.

EXAMPLE 4

The following examples describe phase II clinical studies of human patients that will be administered L104EA29YIg, to reduce or prevent structural damage, including bone or joint erosion using validated radiographic scales. This improvement in reducing or preventing structural damage is parallel to the clinical improvement measured by the clinical parameters.

The status of the bone structure is monitored in some of the human patients prior to treatment with CTLA4Ig or L104EA29YIg. These patients are administered between 0.5 and 20 mg/kg of CTLA4Ig or L104EA29YIg chronically every two to twelve weeks (alone or in combination with other agents) to maintain their therapeutic improvement over time. Radiographs of patients' hands and feet are taken at predefined intervals: 6 months, and then yearly, as recommended by the FDA guidelines. These patients are monitored in long-term extension after 6 and 12 months to determine if treatment with CTLA4Ig or L104EA29YIg reduces the progression of bone deterioration, and then yearly. The patients are monitored by radiographic methods, including X-ray and/or magnetic resonance imaging (MRI), according to standard practice in the art (Larsen, A. K. and M. Eek 1977 *Acta. Radiol. Diag.* 18:481-491; Sharp, J. T., et al., 1985 *Arthritis and Rheumatism* 28:1326-1335). The results of the radiographic data are evaluated for prevention of structural damage, including slowing the progression of bone erosion and cartilage damage, with joint space narrowing and/or prevention of new erosions.

What is claimed:

1. A method of treating a subject having rheumatoid arthritis, wherein the subject has failed at least one Disease Modifying Antirheumatic Drug (DMARD), comprising administering an effective amount of a soluble CTLA4 fusion molecule comprising an extracellular domain of a CTLA4 molecule, wherein the extracellular domain of the CTLA4 molecule comprises the amino acids shown in SEQ ID NO: 17 beginning with methionine at position +27 or with alanine at position +26 and ending with aspartic acid at position +150.

2. The method of claim 1, wherein the DMARD is methotrexate, cyclophosphamide, azathioprine, cyclosporin A, or a tumor necrosis factor-alpha (TNFα) blocker or antagonist.

3. The method of claim 1 or 2, for reducing a symptom of rheumatoid arthritis.

4. The method of claim 3, wherein the symptom is selected from the group consisting of joint swelling, joint tenderness, inflammation, morning stiffness, pain, structural damage, an elevated level of serum C-reactive protein, an elevated level of soluble IL-2r, an elevated level of soluble ICAM-1, an elevated level of soluble E-selectin and an elevated erythrocyte sedimentation rate.

5. The method of claims 1 or 2, wherein an effective amount of the soluble CTLA4 fusion molecule is 10 mg/kg weight of the subject.

6. The method of claims 1 or 2, wherein the effective amount of the soluble CTLA4 fusion molecule is 0.5 mg/kg weight of the subject.

7. The method of claims 1 or 2, wherein the effective amount of the soluble CTLA4 fusion molecule is 2 mg/kg weight of the subject.

8. The method of claim 5, wherein the effective amount of the soluble CTLA4 fusion molecule is administered intravenously over 1 hour.

9. The method of claim 1, wherein the effective amount of the soluble CTLA4 fusion molecule is 0.5 to 10 mg/kg weight of a subject.

10. The method of claim 1, wherein the effective amount of the soluble CTLA4 fusion molecule is 0.1 to 20 mg/kg weight of a subject.

11. The method of claim 1, wherein administration is effected locally or systemically.

12. The method of claim 11, wherein administration is selected from the group consisting of intravenous, intramuscular, subcutaneous, implantable pump, continuous infusion, liposomal and oral administration.

13. The method of claim 1, wherein the extracellular domain of the CTLA4 molecule is joined to a non-CTLA4 molecule.

14. The method of claim 13, wherein the non-CTLA4 molecule comprises an amino acid sequence which alters the solubility or affinity of the soluble CTLA4 fusion molecule.

15. The method of claim 14, wherein the amino acid sequence which alters the solubility or affinity comprises an immunoglobulin moiety.

16. The method of claim 15, wherein the immunoglobulin moiety is an immunoglobulin constant region or portion thereof.

17. The method of claim 16, wherein the immunoglobulin constant region or portion thereof is mutated to reduce effector function.

18. The method of claim 16, wherein the immunoglobulin constant region or portion thereof is mutated to reduce effector function.

19. The method of claim 16, wherein the immunoglobulin constant region or portion thereof comprises a hinge, CH2 and CH3 regions of a human or monkey immunoglobulin molecule.

20. The method of claim 17, wherein the immunoglobulin constant region or portion thereof comprises a hinge, CH2 and CH3 regions of a human or monkey immunoglobulin molecule.

21. A method for reducing or preventing structural damage in a subject having a rheumatic disease comprising administering an effective amount of a soluble CTLA4 fusion molecule comprising an extracellular domain of a CTLA4 molecule, wherein the extracellular domain of the CTLA4 molecule comprises the amino acids shown in SEQ ID NO: 17 beginning with methionine at position +27 or with alanine at position +26 and ending with aspartic acid at position +150.

22. The method of claim 21, wherein the structural damage is bone or joint erosion.

23. The method of claim 21, wherein an effective amount of the soluble CTLA4 fusion molecule is 0.5 and 20 mg/kg weight of the subject.

24. The method of claim 5 comprising administering to a subject a soluble CTLA4 fusion molecule encoded by a nucleic acid molecule designated ATCC No. 68629.

25. The method of claim 9 or 10 comprising administering to a subject a soluble CTLA4 fusion molecule encoded by a nucleic acid molecule designated ATCC No. 68629.

26. The method of claim 5 comprising administering to a subject a soluble CTLA4 fusion molecule, wherein said soluble CTLA4 fusion molecule has the amino acid sequence of a CTLA4Ig fusion protein expressed by the cell deposited as ATCC CRL-10762.

27. The method of claims 1, wherein administration of the effective amount of the soluble CTLA4 fusion molecule comprises intravenous infusion on days 1, 15, 29 and 57.

28. The method of claim 1, wherein administration of the soluble CTLA4 fusion molecule improves ACR 20, 50 and/or 70 response rates.

29. The method of claim 1, wherein the soluble CTLA4 fusion molecule is CTLA4Ig shown in SEQ ID NO: 19 beginning with methionine at position +27 or with alanine at position +26 and ending with lysine at position +383.

30. The method of claim 1 wherein the subject is selected from the group consisting of human, monkey, ape, dog, cat, cow, horse, rabbit, mouse, and rat.

31. The method of claim 21 wherein the rheumatic disease is rheumatoid arthritis.

* * * * *

UNITED STATES PATENT AND TRADEMARK OFFICE
CERTIFICATE OF CORRECTION

PATENT NO. : 7,455,835 B2  
APPLICATION NO. : 09/898195  
DATED : November 25, 2008  
INVENTOR(S) : Robert Cohen et al.

Page 1 of 1

It is certified that error appears in the above-identified patent and that said Letters Patent is hereby corrected as shown below:

Title Pg, Item (56)
In Other Publications page 4
    in Exhibit 131 reference, Author is listed as Pearson, et al. should be "Larsen et al.,"

Signed and Sealed this

Twenty-fourth Day of February, 2009

JOHN DOLL  
*Acting Director of the United States Patent and Trademark Office*